US007897750B2

(12) United States Patent
Monforte

(10) Patent No.: US 7,897,750 B2
(45) Date of Patent: Mar. 1, 2011

(54) STRATEGIES FOR GENE EXPRESSION ANALYSIS

(75) Inventor: Joseph Monforte, Kensington, CA (US)

(73) Assignee: Althea Technologies, Inc., San Diego, CA (US)

( * ) Notice: Subject to any disclaimer, the term of this patent is extended or adjusted under 35 U.S.C. 154(b) by 0 days.

(21) Appl. No.: 12/315,115

(22) Filed: Nov. 26, 2008

(65) Prior Publication Data

US 2009/0149346 A1   Jun. 11, 2009

Related U.S. Application Data

(63) Continuation of application No. 10/622,010, filed on Jul. 16, 2003, now Pat. No. 7,476,519.

(60) Provisional application No. 60/397,393, filed on Jul. 19, 2002.

(51) Int. Cl.
*C07H 21/04* (2006.01)
*C12Q 1/68* (2006.01)
*C12P 19/34* (2006.01)

(52) U.S. Cl. ........ 536/24.33; 435/6; 435/91.1; 435/91.2; 536/24.3

(58) Field of Classification Search ...................... None
See application file for complete search history.

(56) References Cited

U.S. PATENT DOCUMENTS

| | | | |
|---|---|---|---|
| 5,143,854 | A | 9/1992 | Pirrung et al. |
| 5,545,522 | A | 8/1996 | Van Gelder et al. |
| 5,595,895 | A | 1/1997 | Miki et al. |
| 5,807,522 | A | 9/1998 | Brown et al. |
| 5,882,856 | A | 3/1999 | Shuber |
| 5,922,617 | A | 7/1999 | Wang et al. |
| 5,962,271 | A | 10/1999 | Chenchik et al. |
| 6,046,038 | A | 4/2000 | Nilsen |
| 6,087,102 | A | 7/2000 | Chenchik et al. |
| 6,207,372 | B1 | 3/2001 | Shuber |
| 6,251,639 | B1 | 6/2001 | Kurn |
| 6,287,768 | B1 | 9/2001 | Chenchik et al. |
| 6,406,840 | B1 | 6/2002 | Li et al. |
| 6,429,027 | B1 * | 8/2002 | Chee et al. ............ 436/518 |
| 6,458,566 | B2 | 10/2002 | Alland et al. |
| 6,489,159 | B1 | 12/2002 | Chenchik et al. |
| 6,500,938 | B1 | 12/2002 | Au-Young et al. |
| 6,635,423 | B2 | 10/2003 | Dooley et al. |

FOREIGN PATENT DOCUMENTS

| | | | |
|---|---|---|---|
| WO | WO 97/10365 | A1 | 3/1997 |
| WO | WO 9710365 | A1 * | 3/1997 |
| WO | WO 97/27317 | A1 | 7/1997 |
| WO | WO 99/27090 | | 6/1999 |
| WO | WO 99/35289 | | 7/1999 |
| WO | WO 01/55454 | | 8/2001 |
| WO | WO 02/08466 | | 1/2002 |
| WO | WO 02/40717 | A2 | 5/2002 |

OTHER PUBLICATIONS

Shuber et al., "High throughput parallel analysis of hundreds of patient samples for more than 100 mutations in multiple disease genes," Huma Molecular Genetics, 1997, vol. 6, No. 3, pp. 337-347.*

White et al., "Cytoplasmic Dot hybridization," The Journal of Biological Chemistry, Aug. 1982, vol. 257, No. 15, pp. 8569-8572.*
Walker et al., "Effects of Prolactin in Stimulating Disease Activity in Systemic Lupus Erythematosus," Annals of New York Academy of Sciences, May 1998, vol. 840, pp. 762-772.*
Eberwine, Amplifications of mRNA Populations Using aRNA Generated from Immobilized Oligo (dT)-T7 Primed cDNA, Biotechniques 20: 584-591 (1996).
Fodor et al., Light-Directed Spatially Addressable Parallel Chemical Synthesis, Science 251:767-773 (1991).
Hoffman. (2001) "Microarray applications using promega products," *Promega Notes*.
Puskas et al., RNA Amplification Results in Reproducible Microarray Data with Slight Ratio Bias, Biotechniques 32:6; 1330-1334 (2002).
Schena et al., Quantitative Monitoring of Gene Expression Patterns with a Complementary DNA Microarray, Science 270:467-470 (1995).
Shepard and Cooper (2000) "Assessing the Expression of Two Genes Simultaneously in Surgical Specimens Using Polymerase Chain Reaction." *Modern Pathology* 13(4): 401-406.
Thomas et al., Identification of Toxicologically Predictive Gene Sets Using cDNA Microarrays, Molecular Pharmacology 60: 1189-1194 (2001).
Tsuruoka & Fujii. (1999) "Rapid and specific detection of RNA base sequence using fluorescence polarization," *Nucleic Acids Symposium Series*, 42:239-240.
Van Gelder et al., Amplified RNA Synthesized from Limited Quantities of Heterogeneous cDNA, Proc. Natl. Acad. Sci. USA 87:5; 1663-1667 (1990).
Van'T Veer et.al., Gene Expression Profiling Predicts Clinical Outcome of Breast Cancer, Nature 415: 530-536 (2002).
Yadetie et al. (2004) "Miniaturized fluorescent RNA dot blot method for rapid quantitation of gene expression," *BMC Biotechnology*, 4:12.
Cho et al. (2001) "Antisense DNAs multisite genomic modulators identified by DNA microarray," *PNAS*, 98(17):9819-9823.
Porkka and Visakorpi (2001) "Detection of differentially expressed genes in prostate cancer by combining suppression subtractive hybridization and cDNA library array," *J. Pathology*, 193:73-79.
Clavel et al. (1998) "DNA-EIA to detect high and low risk HPV genotypes in cervical leasions with E6/E7 primer mediated multiplex PCR." *Journal of Clinical Pathology*, 51: 38-43.
Fan and Henrickson (1996) "Rapid Diagnosis of Human Parainfluenza Virus Type 1 Infection of Quantitative Reverse Transcription-PCR-Enzyme Hybridization Assay." *Journal of Cilincal Microbiology*, 34(8): 1914-1917.
Neilan et al. (1997) "A universal procedure for primer labeling of amplicons." *Nucleic Acids Research*, 25(14): 2938-2939.
Osiowy et al. (1998) "Direct Detection of Respiratory Syncytial Virus, Parainfluenza Virus, and Adenovirus in Clinical Respiratory Specimens by a Mutliplex Reverse Transcription-PCR Assay." *Journal of Clilnical Microbiology*, 36(11): 3149-3454.
Peng et al. (1996) "Replication Error Phenotype and p53 Gene Mutation in Lymphomas of Musoca-Associated Lymphoid Tissue." *American Journal of Pathology*, 148(2): 643-648.

(Continued)

*Primary Examiner* — Young J Kim
(74) *Attorney, Agent, or Firm* — Stacy Landry; Christina Onufryk; Quine Intellectual Property Law Group, P.C.

(57) ABSTRACT

The invention provides methods for screening compound or chemical libraries by analyzing expressed RNA samples from biological samples treated with members of a compound library in a high throughput format.

7 Claims, 12 Drawing Sheets

OTHER PUBLICATIONS

Recchi et al. (1998) "Mutiplex RR-PR method for the analysis of the expression of human sialyltransferases: application to breast cancer cells." *Glycoconjugate Journal*, 15: 19-27.

Yu et al. (1996) Specific Inhibitionof PCR by Non-Extendable Oligonucleotides Using a 5' to 3' Exonuclease-Deficient DNA Polymerase. *BioTechnoques*, 23: 714-730.

* cited by examiner

Compound Library Screen x 100 — Compound treatment x 7 — Arraying & RNA isolation x 7 — Probing & signal amplification

```
                        SEQUENCE LISTING

<160> NUMBER OF SEQ ID NOS: 114

<210> SEQ ID NO 1
<211> LENGTH: 38
<212> TYPE: DNA
<213> ORGANISM: artificial
<220> FEATURE:
<223> OTHER INFORMATION: amplification primer

<400> SEQUENCE: 1
aggtgacact atagaatatt tcccctccaa actcctttt                              38

<210> SEQ ID NO 2
<211> LENGTH: 39
<212> TYPE: DNA
<213> ORGANISM: artificial
<220> FEATURE:
<223> OTHER INFORMATION: amplification primer

<400> SEQUENCE: 2
gtacgactca ctatagggaa agatcaccgt tcccaactg                              39

<210> SEQ ID NO 3
<211> LENGTH: 38
<212> TYPE: DNA
<213> ORGANISM: artificial
<220> FEATURE:
<223> OTHER INFORMATION: amplification primer

<400> SEQUENCE: 3
aggtgacact atagaatatt tcctggtgag tgggattc                               38

<210> SEQ ID NO 4
<211> LENGTH: 39
<212> TYPE: DNA
<213> ORGANISM: artificial
<220> FEATURE:
<223> OTHER INFORMATION: amplification primer

<400> SEQUENCE: 4
gtacgactca ctatagggat ctccagtcgt tccatctcc                              39

<210> SEQ ID NO 5
<211> LENGTH: 38
<212> TYPE: DNA
<213> ORGANISM: artificial
<220> FEATURE:
<223> OTHER INFORMATION: amplification primer

<400> SEQUENCE: 5
aggtgacact atagaataga cccagatcat gccagtct                               38
```

```
<210> SEQ ID NO 6
<211> LENGTH: 39
<212> TYPE: DNA
<213> ORGANISM: artificial
<220> FEATURE:
<223> OTHER INFORMATION: amplification primer

<400> SEQUENCE: 6
gtacgactca ctatagggaa aaatcccatt gtggctgag                              39

<210> SEQ ID NO 7
<211> LENGTH: 38
<212> TYPE: DNA
<213> ORGANISM: artificial
<220> FEATURE:
<223> OTHER INFORMATION: amplification primer

<400> SEQUENCE: 7
aggtgacact atagaatagt tcctatcctc ctgtggca                               38

<210> SEQ ID NO 8
<211> LENGTH: 39
<212> TYPE: DNA
<213> ORGANISM: artificial
<220> FEATURE:
<223> OTHER INFORMATION: amplification primer

<400> SEQUENCE: 8
gtacgactca ctatagggaa caaatcggta accagcagc                              39

<210> SEQ ID NO 9
<211> LENGTH: 38
<212> TYPE: DNA
<213> ORGANISM: artificial
<220> FEATURE:
<223> OTHER INFORMATION: amplification primer

<400> SEQUENCE: 9
aggtgacact atagaatatt catctctttg aggacgcc                               38

<210> SEQ ID NO 10
<211> LENGTH: 39
<212> TYPE: DNA
<213> ORGANISM: artificial
<220> FEATURE:
<223> OTHER INFORMATION: amplification primer

<400> SEQUENCE: 10
gtacgactca ctatagggaa gaaacactgg gtgcaggag                              39

<210> SEQ ID NO 11
<211> LENGTH: 38
<212> TYPE: DNA
<213> ORGANISM: artificial
<220> FEATURE:
<223> OTHER INFORMATION: amplification primer

<400> SEQUENCE: 11
aggtgacact atagaatagg ttggatttgc tcattgct                               38

<210> SEQ ID NO 12
<211> LENGTH: 39
<212> TYPE: DNA
<213> ORGANISM: artificial
<220> FEATURE:
<223> OTHER INFORMATION: amplification primer
```

<400> SEQUENCE: 12
gtacgactca ctatagggat tgcccttaat cccagacag                                    39

<210> SEQ ID NO 13
<211> LENGTH: 38
<212> TYPE: DNA
<213> ORGANISM: artificial
<220> FEATURE:
<223> OTHER INFORMATION: amplification primer

<400> SEQUENCE: 13
aggtgacact atagaatacc gaagagcact gaaaaacc                                     38

<210> SEQ ID NO 14
<211> LENGTH: 39
<212> TYPE: DNA
<213> ORGANISM: artificial
<220> FEATURE:
<223> OTHER INFORMATION: amplification primer

<400> SEQUENCE: 14
gtacgactca ctatagggag aattggctag ggcaatcaa                                    39

<210> SEQ ID NO 15
<211> LENGTH: 38
<212> TYPE: DNA
<213> ORGANISM: artificial
<220> FEATURE:
<223> OTHER INFORMATION: amplification primer

<400> SEQUENCE: 15
aggtgacact atagaatagt cctgcttggt gacaagtt                                     38

<210> SEQ ID NO 16
<211> LENGTH: 39
<212> TYPE: DNA
<213> ORGANISM: artificial
<220> FEATURE:
<223> OTHER INFORMATION: amplification primer

<400> SEQUENCE: 16
gtacgactca ctatagggat gcttgccaga caggtctta                                    39

<210> SEQ ID NO 17
<211> LENGTH: 38
<212> TYPE: DNA
<213> ORGANISM: artificial
<220> FEATURE:
<223> OTHER INFORMATION: amplification primer

<400> SEQUENCE: 17
aggtgacact atagaatatt cctgttgatg ggaaaagc                                     38

<210> SEQ ID NO 18
<211> LENGTH: 39
<212> TYPE: DNA
<213> ORGANISM: artificial
<220> FEATURE:
<223> OTHER INFORMATION: amplification primer

<400> SEQUENCE: 18
gtacgactca ctatagggac aagcaggaca agggagaag                                    39

<210> SEQ ID NO 19
<211> LENGTH: 38
<212> TYPE: DNA

-continued

<213> ORGANISM: artificial
<220> FEATURE:
<223> OTHER INFORMATION: amplification primer

<400> SEQUENCE: 19
aggtgacact atagaatatt tcatcctgtc cgtaaggg                    38

<210> SEQ ID NO 20
<211> LENGTH: 39
<212> TYPE: DNA
<213> ORGANISM: artificial
<220> FEATURE:
<223> OTHER INFORMATION: amplification primer

<400> SEQUENCE: 20
gtacgactca ctatagggat agggaaatgc cagtatcgc                   39

<210> SEQ ID NO 21
<211> LENGTH: 38
<212> TYPE: DNA
<213> ORGANISM: artificial
<220> FEATURE:
<223> OTHER INFORMATION: amplification primer

<400> SEQUENCE: 21
aggtgacact atagaatatg aagagcaaat gagccaaa                    38

<210> SEQ ID NO 22
<211> LENGTH: 39
<212> TYPE: DNA
<213> ORGANISM: artificial
<220> FEATURE:
<223> OTHER INFORMATION: amplification primer

<400> SEQUENCE: 22
gtacgactca ctatagggaa caggattcac agtctgggc                   39

<210> SEQ ID NO 23
<211> LENGTH: 38
<212> TYPE: DNA
<213> ORGANISM: artificial
<220> FEATURE:
<223> OTHER INFORMATION: amplification primer

<400> SEQUENCE: 23
aggtgacact atagaataca gctcagggag aagtgacc                    38

<210> SEQ ID NO 24
<211> LENGTH: 39
<212> TYPE: DNA
<213> ORGANISM: artificial
<220> FEATURE:
<223> OTHER INFORMATION: amplification primer

<400> SEQUENCE: 24
gtacgactca ctatagggag caggtctcaa aggaagtgg                   39

<210> SEQ ID NO 25
<211> LENGTH: 38
<212> TYPE: DNA
<213> ORGANISM: artificial
<220> FEATURE:
<223> OTHER INFORMATION: amplification primer

<400> SEQUENCE: 25
aggtgacact atagaataca gaggagcttg tacccacc                    38

<210> SEQ ID NO 26
<211> LENGTH: 39
<212> TYPE: DNA
<213> ORGANISM: artificial
<220> FEATURE:
<223> OTHER INFORMATION: amplification primer

<400> SEQUENCE: 26
gtacgactca ctatagggac acttctgcat cacggaaga      39

<210> SEQ ID NO 27
<211> LENGTH: 38
<212> TYPE: DNA
<213> ORGANISM: artificial
<220> FEATURE:
<223> OTHER INFORMATION: amplification primer

<400> SEQUENCE: 27
aggtgacact atagaatatc tctgcagtga ttgatgcc       38

<210> SEQ ID NO 28
<211> LENGTH: 39
<212> TYPE: DNA
<213> ORGANISM: artificial
<220> FEATURE:
<223> OTHER INFORMATION: amplification primer

<400> SEQUENCE: 28
gtacgactca ctatagggaa gacagtacag gcccgaaga      39

<210> SEQ ID NO 29
<211> LENGTH: 38
<212> TYPE: DNA
<213> ORGANISM: artificial
<220> FEATURE:
<223> OTHER INFORMATION: amplification primer

<400> SEQUENCE: 29
aggtgacact atagaatatc tgctataggg ttggtggg       38

<210> SEQ ID NO 30
<211> LENGTH: 39
<212> TYPE: DNA
<213> ORGANISM: artificial
<220> FEATURE:
<223> OTHER INFORMATION: amplification primer

<400> SEQUENCE: 30
gtacgactca ctatagggac agcagtgaga agctgatgc      39

<210> SEQ ID NO 31
<211> LENGTH: 38
<212> TYPE: DNA
<213> ORGANISM: artificial
<220> FEATURE:
<223> OTHER INFORMATION: amplification primer

<400> SEQUENCE: 31
aggtgacact atagaatagt ccgagttctc tgcaggtc       38

<210> SEQ ID NO 32
<211> LENGTH: 39
<212> TYPE: DNA
<213> ORGANISM: artificial
<220> FEATURE:
<223> OTHER INFORMATION: amplification primer

<400> SEQUENCE: 32
gtacgactca ctatagggaa aatacacctg gtttgggca                                  39

<210> SEQ ID NO 33
<211> LENGTH: 38
<212> TYPE: DNA
<213> ORGANISM: artificial
<220> FEATURE:
<223> OTHER INFORMATION: amplification primer

<400> SEQUENCE: 33
aggtgacact atagaatagg agaaacttgc taccgcac                                   38

<210> SEQ ID NO 34
<211> LENGTH: 39
<212> TYPE: DNA
<213> ORGANISM: artificial
<220> FEATURE:
<223> OTHER INFORMATION: amplification primer

<400> SEQUENCE: 34
gtacgactca ctatagggaa agggaattt caggcattt                                   39

<210> SEQ ID NO 35
<211> LENGTH: 38
<212> TYPE: DNA
<213> ORGANISM: artificial
<220> FEATURE:
<223> OTHER INFORMATION: amplification primer

<400> SEQUENCE: 35
aggtgacact atagaatatt tttccctgtg ttcttggg                                   38

<210> SEQ ID NO 36
<211> LENGTH: 39
<212> TYPE: DNA
<213> ORGANISM: artificial
<220> FEATURE:
<223> OTHER INFORMATION: amplification primer

<400> SEQUENCE: 36
gtacgactca ctatagggaa aggaggtgca accacacat                                  39

<210> SEQ ID NO 37
<211> LENGTH: 38
<212> TYPE: DNA
<213> ORGANISM: artificial
<220> FEATURE:
<223> OTHER INFORMATION: amplification primer

<400> SEQUENCE: 37
aggtgacact atagaatacc aacagaaacc accgttct                                   38

<210> SEQ ID NO 38
<211> LENGTH: 39
<212> TYPE: DNA
<213> ORGANISM: artificial
<220> FEATURE:
<223> OTHER INFORMATION: amplification primer

<400> SEQUENCE: 38
gtacgactca ctatagggag aggtcaagct gctcaggtc                                  39

<210> SEQ ID NO 39
<211> LENGTH: 38
<212> TYPE: DNA

```
<213> ORGANISM: artificial
<220> FEATURE:
<223> OTHER INFORMATION: amplification primer

<400> SEQUENCE: 39
aggtgacact atagaatacc aaagcctcag gaacaaga                              38

<210> SEQ ID NO 40
<211> LENGTH: 39
<212> TYPE: DNA
<213> ORGANISM: artificial
<220> FEATURE:
<223> OTHER INFORMATION: amplification primer

<400> SEQUENCE: 40
gtacgactca ctagggat gctgaccttc ttccattcc                               39

<210> SEQ ID NO 41
<211> LENGTH: 38
<212> TYPE: DNA
<213> ORGANISM: artificial
<220> FEATURE:
<223> OTHER INFORMATION: amplification primer

<400> SEQUENCE: 41
aggtgacact atagaatagg gctgtccatg tcatctct                              38

<210> SEQ ID NO 42
<211> LENGTH: 39
<212> TYPE: DNA
<213> ORGANISM: artificial
<220> FEATURE:
<223> OTHER INFORMATION: amplification primer

<400> SEQUENCE: 42
gtacgactca ctagggac cagggtcaca gtagggaga                               39

<210> SEQ ID NO 43
<211> LENGTH: 38
<212> TYPE: DNA
<213> ORGANISM: artificial
<220> FEATURE:
<223> OTHER INFORMATION: amplification primer

<400> SEQUENCE: 43
aggtgacact atagaatatc ttgcccctga tatcacaa                              38

<210> SEQ ID NO 44
<211> LENGTH: 39
<212> TYPE: DNA
<213> ORGANISM: artificial
<220> FEATURE:
<223> OTHER INFORMATION: amplification primer

<400> SEQUENCE: 44
gtacgactca ctagggaa cctcttgtgc attctgcaa                               39

<210> SEQ ID NO 45
<211> LENGTH: 38
<212> TYPE: DNA
<213> ORGANISM: artificial
<220> FEATURE:
<223> OTHER INFORMATION: amplification primer

<400> SEQUENCE: 45
aggtgacact atagaatagc cctgatgtcg gctaagta                              38
```

```
<210> SEQ ID NO 46
<211> LENGTH: 39
<212> TYPE: DNA
<213> ORGANISM: artificial
<220> FEATURE:
<223> OTHER INFORMATION: amplification primer

<400> SEQUENCE: 46
gtacgactca ctatagggat gcagttttct gggagtgtg                              39

<210> SEQ ID NO 47
<211> LENGTH: 38
<212> TYPE: DNA
<213> ORGANISM: artificial
<220> FEATURE:
<223> OTHER INFORMATION: amplification primer

<400> SEQUENCE: 47
aggtgacact atagaataat ggatgaaaca gctgagca                               38

<210> SEQ ID NO 48
<211> LENGTH: 39
<212> TYPE: DNA
<213> ORGANISM: artificial
<220> FEATURE:
<223> OTHER INFORMATION: amplification primer

<400> SEQUENCE: 48
gtacgactca ctatagggag cgctctacgc aaagtgaat                              39

<210> SEQ ID NO 49
<211> LENGTH: 38
<212> TYPE: DNA
<213> ORGANISM: artificial
<220> FEATURE:
<223> OTHER INFORMATION: amplification primer

<400> SEQUENCE: 49
aggtgacact atagaatatg tgggaacagg aacattca                               38

<210> SEQ ID NO 50
<211> LENGTH: 39
<212> TYPE: DNA
<213> ORGANISM: artificial
<220> FEATURE:
<223> OTHER INFORMATION: amplification primer

<400> SEQUENCE: 50
gtacgactca ctatagggat gtctttcctg cttggctct                              39

<210> SEQ ID NO 51
<211> LENGTH: 38
<212> TYPE: DNA
<213> ORGANISM: artificial
<220> FEATURE:
<223> OTHER INFORMATION: amplification primer

<400> SEQUENCE: 51
aggtgacact atagaatatt ctacatttga gggcccag                               38

<210> SEQ ID NO 52
<211> LENGTH: 39
<212> TYPE: DNA
<213> ORGANISM: artificial
<220> FEATURE:
<223> OTHER INFORMATION: amplification primer
```

<400> SEQUENCE: 52
gtacgactca ctatagggac aaaacatgcc acgaatgag          39

<210> SEQ ID NO 53
<211> LENGTH: 38
<212> TYPE: DNA
<213> ORGANISM: artificial
<220> FEATURE:
<223> OTHER INFORMATION: amplification primer

<400> SEQUENCE: 53
aggtgacact atagaatagc aatctaagca ggggtctg           38

<210> SEQ ID NO 54
<211> LENGTH: 39
<212> TYPE: DNA
<213> ORGANISM: artificial
<220> FEATURE:
<223> OTHER INFORMATION: amplification primer

<400> SEQUENCE: 54
gtacgactca ctatagggac agcacttaga ttcggagcc          39

<210> SEQ ID NO 55
<211> LENGTH: 38
<212> TYPE: DNA
<213> ORGANISM: artificial
<220> FEATURE:
<223> OTHER INFORMATION: amplification primer

<400> SEQUENCE: 55
aggtgacact atagaatata acatggagga gaccaggc           38

<210> SEQ ID NO 56
<211> LENGTH: 39
<212> TYPE: DNA
<213> ORGANISM: artificial
<220> FEATURE:
<223> OTHER INFORMATION: amplification primer

<400> SEQUENCE: 56
gtacgactca ctatagggac cctggagcag ttttgtagc          39

<210> SEQ ID NO 57
<211> LENGTH: 38
<212> TYPE: DNA
<213> ORGANISM: artificial
<220> FEATURE:
<223> OTHER INFORMATION: amplification primer

<400> SEQUENCE: 57
aggtgacact atagaatagg gaatcggaag ggttcata           38

<210> SEQ ID NO 58
<211> LENGTH: 39
<212> TYPE: DNA
<213> ORGANISM: artificial
<220> FEATURE:
<223> OTHER INFORMATION: amplification primer

<400> SEQUENCE: 58
gtacgactca ctatagggag gagggaccaa ccttgaaat          39

<210> SEQ ID NO 59
<211> LENGTH: 38
<212> TYPE: DNA

-continued

<213> ORGANISM: artificial
<220> FEATURE:
<223> OTHER INFORMATION: amplification primer

<400> SEQUENCE: 59
aggtgacact atagaatact gtcagaagag gagacccg                                    38

<210> SEQ ID NO 60
<211> LENGTH: 39
<212> TYPE: DNA
<213> ORGANISM: artificial
<220> FEATURE:
<223> OTHER INFORMATION: amplification primer

<400> SEQUENCE: 60
gtacgactca ctatagggag caaattttct ggcttgagg                                   39

<210> SEQ ID NO 61
<211> LENGTH: 38
<212> TYPE: DNA
<213> ORGANISM: artificial
<220> FEATURE:
<223> OTHER INFORMATION: amplification primer

<400> SEQUENCE: 61
aggtgacact atagaatatc agtactaaac ccccgctg                                    38

<210> SEQ ID NO 62
<211> LENGTH: 39
<212> TYPE: DNA
<213> ORGANISM: artificial
<220> FEATURE:
<223> OTHER INFORMATION: amplification primer

<400> SEQUENCE: 62
gtacgactca ctatagggat ttgggcgata ttttccac                                    39

<210> SEQ ID NO 63
<211> LENGTH: 38
<212> TYPE: DNA
<213> ORGANISM: artificial
<220> FEATURE:
<223> OTHER INFORMATION: amplification primer

<400> SEQUENCE: 63
aggtgacact atagaataga agtgttccgt cctggcta                                    38

<210> SEQ ID NO 64
<211> LENGTH: 39
<212> TYPE: DNA
<213> ORGANISM: artificial
<220> FEATURE:
<223> OTHER INFORMATION: amplification primer

<400> SEQUENCE: 64
gtacgactca ctatagggat gctgaataca gacttggcg                                   39

<210> SEQ ID NO 65
<211> LENGTH: 38
<212> TYPE: DNA
<213> ORGANISM: artificial
<220> FEATURE:
<223> OTHER INFORMATION: amplification primer

<400> SEQUENCE: 65
aggtgacact atagaatagg gggtttatga gccacatt                                    38

<210> SEQ ID NO 66
<211> LENGTH: 39
<212> TYPE: DNA
<213> ORGANISM: artificial
<220> FEATURE:
<223> OTHER INFORMATION: amplification primer

<400> SEQUENCE: 66
gtacgactca ctatagggat ttagggaacc tccgtgaga					39

<210> SEQ ID NO 67
<211> LENGTH: 38
<212> TYPE: DNA
<213> ORGANISM: artificial
<220> FEATURE:
<223> OTHER INFORMATION: amplification primer

<400> SEQUENCE: 67
aggtgacact atagaatatg ggtgtggatt ctgttctg					38

<210> SEQ ID NO 68
<211> LENGTH: 39
<212> TYPE: DNA
<213> ORGANISM: artificial
<220> FEATURE:
<223> OTHER INFORMATION: amplification primer

<400> SEQUENCE: 68
gtacgactca ctatagggat ggggtttgaa gttggaatc					39

<210> SEQ ID NO 69
<211> LENGTH: 38
<212> TYPE: DNA
<213> ORGANISM: artificial
<220> FEATURE:
<223> OTHER INFORMATION: amplification primer

<400> SEQUENCE: 69
aggtgacact atagaatatg caaagggaaa tgcacata					38

<210> SEQ ID NO 70
<211> LENGTH: 39
<212> TYPE: DNA
<213> ORGANISM: artificial
<220> FEATURE:
<223> OTHER INFORMATION: amplification primer

<400> SEQUENCE: 70
gtacgactca ctatagggac cttcccagag ctcaatcag					39

<210> SEQ ID NO 71
<211> LENGTH: 38
<212> TYPE: DNA
<213> ORGANISM: artificial
<220> FEATURE:
<223> OTHER INFORMATION: amplification primer

<400> SEQUENCE: 71
aggtgacact atagaatacg aactttgaca gcgacaag					38

<210> SEQ ID NO 72
<211> LENGTH: 39
<212> TYPE: DNA
<213> ORGANISM: artificial
<220> FEATURE:
<223> OTHER INFORMATION: amplification primer -continued

<400> SEQUENCE: 72
gtacgactca ctatagggac cctcagtgaa gcggtacat                              39

<210> SEQ ID NO 73
<211> LENGTH: 38
<212> TYPE: DNA
<213> ORGANISM: artificial
<220> FEATURE:
<223> OTHER INFORMATION: amplification primer

<400> SEQUENCE: 73
aggtgacact atagaatacg caaagaaagc tcaggaaa                               38

<210> SEQ ID NO 74
<211> LENGTH: 39
<212> TYPE: DNA
<213> ORGANISM: artificial
<220> FEATURE:
<223> OTHER INFORMATION: amplification primer

<400> SEQUENCE: 74
gtacgactca ctatagggaa gacaagacag gctggcact                              39

<210> SEQ ID NO 75
<211> LENGTH: 38
<212> TYPE: DNA
<213> ORGANISM: artificial
<220> FEATURE:
<223> OTHER INFORMATION: amplification primer

<400> SEQUENCE: 75
aggtgacact atagaatatc tccatctcct gacctcgt                               38

<210> SEQ ID NO 76
<211> LENGTH: 39
<212> TYPE: DNA
<213> ORGANISM: artificial
<220> FEATURE:
<223> OTHER INFORMATION: amplification primer

<400> SEQUENCE: 76
gtacgactca ctatagggac ttggtctccc aaagtgctc                              39

<210> SEQ ID NO 77
<211> LENGTH: 38
<212> TYPE: DNA
<213> ORGANISM: artificial
<220> FEATURE:
<223> OTHER INFORMATION: amplification primer

<400> SEQUENCE: 77
aggtgacact atagaatagg tggagcagtt cctgtgtt                               38

<210> SEQ ID NO 78
<211> LENGTH: 39
<212> TYPE: DNA
<213> ORGANISM: artificial
<220> FEATURE:
<223> OTHER INFORMATION: amplification primer

<400> SEQUENCE: 78
gtacgactca ctatagggat tcacattgca ctggaaagc                              39

<210> SEQ ID NO 79
<211> LENGTH: 38
<212> TYPE: DNA

```
<213> ORGANISM: artificial
<220> FEATURE:
<223> OTHER INFORMATION: amplification primer

<400> SEQUENCE: 79
aggtgacact atagaataac cggcttcctc attacctt                              38

<210> SEQ ID NO 80
<211> LENGTH: 39
<212> TYPE: DNA
<213> ORGANISM: artificial
<220> FEATURE:
<223> OTHER INFORMATION: amplification primer

<400> SEQUENCE: 80
gtacgactca ctatagggag acattggtgg tggtctcct                             39

<210> SEQ ID NO 81
<211> LENGTH: 38
<212> TYPE: DNA
<213> ORGANISM: artificial
<220> FEATURE:
<223> OTHER INFORMATION: amplification primer

<400> SEQUENCE: 81
aggtgacact atagaatatc caggccactt ttcacttc                              38

<210> SEQ ID NO 82
<211> LENGTH: 39
<212> TYPE: DNA
<213> ORGANISM: artificial
<220> FEATURE:
<223> OTHER INFORMATION: amplification primer

<400> SEQUENCE: 82
gtacgactca ctatagggac tcttccgtgg tggagtagc                             39

<210> SEQ ID NO 83
<211> LENGTH: 38
<212> TYPE: DNA
<213> ORGANISM: artificial
<220> FEATURE:
<223> OTHER INFORMATION: amplification primer

<400> SEQUENCE: 83
aggtgacact atagaatagt ggttcctgaa cctgttgc                              38

<210> SEQ ID NO 84
<211> LENGTH: 39
<212> TYPE: DNA
<213> ORGANISM: artificial
<220> FEATURE:
<223> OTHER INFORMATION: amplification primer

<400> SEQUENCE: 84
gtacgactca ctatagggag agcttgccat tcagagagg                             39

<210> SEQ ID NO 85
<211> LENGTH: 38
<212> TYPE: DNA
<213> ORGANISM: artificial
<220> FEATURE:
<223> OTHER INFORMATION: amplification primer

<400> SEQUENCE: 85
aggtgacact atagaataga agggagagga agggagtg                              38
```

```
<210> SEQ ID NO 86
<211> LENGTH: 39
<212> TYPE: DNA
<213> ORGANISM: artificial
<220> FEATURE:
<223> OTHER INFORMATION: amplification primer

<400> SEQUENCE: 86
gtacgactca ctagggat caaaggacac aacgagcag                              39

<210> SEQ ID NO 87
<211> LENGTH: 38
<212> TYPE: DNA
<213> ORGANISM: artificial
<220> FEATURE:
<223> OTHER INFORMATION: amplification primer

<400> SEQUENCE: 87
aggtgacact atagaatagg acgagatcaa gccctaca                             38

<210> SEQ ID NO 88
<211> LENGTH: 39
<212> TYPE: DNA
<213> ORGANISM: artificial
<220> FEATURE:
<223> OTHER INFORMATION: amplification primer

<400> SEQUENCE: 88
gtacgactca ctagggac gcggaagtcc tctagacag                              39

<210> SEQ ID NO 89
<211> LENGTH: 38
<212> TYPE: DNA
<213> ORGANISM: artificial
<220> FEATURE:
<223> OTHER INFORMATION: amplification primer

<400> SEQUENCE: 89
aggtgacact atagaatatg gatcccggaa tagtcaac                             38

<210> SEQ ID NO 90
<211> LENGTH: 39
<212> TYPE: DNA
<213> ORGANISM: artificial
<220> FEATURE:
<223> OTHER INFORMATION: amplification primer

<400> SEQUENCE: 90
gtacgactca ctagggag gcacaggaag ccataaaga                              39

<210> SEQ ID NO 91
<211> LENGTH: 38
<212> TYPE: DNA
<213> ORGANISM: artificial
<220> FEATURE:
<223> OTHER INFORMATION: amplification primer

<400> SEQUENCE: 91
aggtgacact atagaatatt ttgggacgta aaagctgg                             38

<210> SEQ ID NO 92
<211> LENGTH: 39
<212> TYPE: DNA
<213> ORGANISM: artificial
<220> FEATURE:
<223> OTHER INFORMATION: amplification primer
```

<400> SEQUENCE: 92
gtacgactca ctatagggat ttgaaggggt ttgcttgtc          39

<210> SEQ ID NO 93
<211> LENGTH: 38
<212> TYPE: DNA
<213> ORGANISM: artificial
<220> FEATURE:
<223> OTHER INFORMATION: amplification primer

<400> SEQUENCE: 93
aggtgacact atagaatact tcctgcagag agaggagc           38

<210> SEQ ID NO 94
<211> LENGTH: 39
<212> TYPE: DNA
<213> ORGANISM: artificial
<220> FEATURE:
<223> OTHER INFORMATION: amplification primer

<400> SEQUENCE: 94
gtacgactca ctatagggaa caccaaaata ccccatcca          39

<210> SEQ ID NO 95
<211> LENGTH: 38
<212> TYPE: DNA
<213> ORGANISM: artificial
<220> FEATURE:
<223> OTHER INFORMATION: amplification primer

<400> SEQUENCE: 95
aggtgacact atagaataat gtacttggag gaccgcac           38

<210> SEQ ID NO 96
<211> LENGTH: 39
<212> TYPE: DNA
<213> ORGANISM: artificial
<220> FEATURE:
<223> OTHER INFORMATION: amplification primer

<400> SEQUENCE: 96
gtacgactca ctatagggat gcctcttatc agccaggtc          39

<210> SEQ ID NO 97
<211> LENGTH: 38
<212> TYPE: DNA
<213> ORGANISM: artificial
<220> FEATURE:
<223> OTHER INFORMATION: amplification primer

<400> SEQUENCE: 97
aggtgacact atagaataaa cattgaatgg cacagcaa           38

<210> SEQ ID NO 98
<211> LENGTH: 39
<212> TYPE: DNA
<213> ORGANISM: artificial
<220> FEATURE:
<223> OTHER INFORMATION: amplification primer

<400> SEQUENCE: 98
gtacgactca ctatagggaa accaggcaca aggttcaag          39

<210> SEQ ID NO 99
<211> LENGTH: 38
<212> TYPE: DNA

-continued

<213> ORGANISM: artificial
<220> FEATURE:
<223> OTHER INFORMATION: amplification primer

<400> SEQUENCE: 99
aggtgacact atagaataat tctggcaaag ccaatctg                38

<210> SEQ ID NO 100
<211> LENGTH: 39
<212> TYPE: DNA
<213> ORGANISM: artificial
<220> FEATURE:
<223> OTHER INFORMATION: amplification primer

<400> SEQUENCE: 100
gtacgactca ctagggag atggtgttgc aggatgttg                39

<210> SEQ ID NO 101
<211> LENGTH: 38
<212> TYPE: DNA
<213> ORGANISM: artificial
<220> FEATURE:
<223> OTHER INFORMATION: amplification primer

<400> SEQUENCE: 101
aggtgacact atagaataat cagcatttcc aaccacaa                38

<210> SEQ ID NO 102
<211> LENGTH: 39
<212> TYPE: DNA
<213> ORGANISM: artificial
<220> FEATURE:
<223> OTHER INFORMATION: amplification primer

<400> SEQUENCE: 102
gtacgactca ctagggag tctcgctaat aaccccagc                39

<210> SEQ ID NO 103
<211> LENGTH: 38
<212> TYPE: DNA
<213> ORGANISM: artificial
<220> FEATURE:
<223> OTHER INFORMATION: amplification primer

<400> SEQUENCE: 103
aggtgacact atagaatatt gtacaataca acgggcga                38

<210> SEQ ID NO 104
<211> LENGTH: 40
<212> TYPE: DNA
<213> ORGANISM: artificial
<220> FEATURE:
<223> OTHER INFORMATION: amplification primer

<400> SEQUENCE: 104
gtacgactca ctagggat tggttcaaga agctggaaaa                40

<210> SEQ ID NO 105
<211> LENGTH: 38
<212> TYPE: DNA
<213> ORGANISM: artificial
<220> FEATURE:
<223> OTHER INFORMATION: amplification primer

<400> SEQUENCE: 105
aggtgacact atagaatagg acacatggaa caaaccaa                38

<210> SEQ ID NO 106
<211> LENGTH: 39
<212> TYPE: DNA
<213> ORGANISM: artificial
<220> FEATURE:
<223> OTHER INFORMATION: amplification primer

<400> SEQUENCE: 106
gtacgactca ctatagggaa atgtttctcc tggttggga                                 39

<210> SEQ ID NO 107
<211> LENGTH: 37
<212> TYPE: DNA
<213> ORGANISM: artificial
<220> FEATURE:
<223> OTHER INFORMATION: amplification primer

<400> SEQUENCE: 107
aggtgacact atagaatact gacatgctca cgctctg                                   37

<210> SEQ ID NO 108
<211> LENGTH: 39
<212> TYPE: DNA
<213> ORGANISM: artificial
<220> FEATURE:
<223> OTHER INFORMATION: amplification primer

<400> SEQUENCE: 108
gtacgactca ctatagggac cccatacctt gatggagaa                                 39

<210> SEQ ID NO 109
<211> LENGTH: 38
<212> TYPE: DNA
<213> ORGANISM: artificial
<220> FEATURE:
<223> OTHER INFORMATION: amplification primer

<400> SEQUENCE: 109
aggtgacact atagaatagg gtgaacaatt ttgtggct                                  38

<210> SEQ ID NO 110
<211> LENGTH: 39
<212> TYPE: DNA
<213> ORGANISM: artificial
<220> FEATURE:
<223> OTHER INFORMATION: amplification primer

<400> SEQUENCE: 110
gtacgactca ctatagggac gagagtgcag ggataaagg                                 39

<210> SEQ ID NO 111
<211> LENGTH: 39
<212> TYPE: DNA
<213> ORGANISM: artificial
<220> FEATURE:
<223> OTHER INFORMATION: amplification primer

<400> SEQUENCE: 111
aggtgacact atagaatata cctcgcatgt gtcacaacg                                 39

<210> SEQ ID NO 112
<211> LENGTH: 38
<212> TYPE: DNA
<213> ORGANISM: artificial
<220> FEATURE:
<223> OTHER INFORMATION: amplification primer -continued

```
<400> SEQUENCE: 112
gtacgactca ctatagggac cggcatctgg ctgatttt                              38

<210> SEQ ID NO 113
<211> LENGTH: 18
<212> TYPE: DNA
<213> ORGANISM: artificial
<220> FEATURE:
<223> OTHER INFORMATION: amplification primer

<400> SEQUENCE: 113
aggtgacact atagaata                                                    18

<210> SEQ ID NO 114
<211> LENGTH: 19
<212> TYPE: DNA
<213> ORGANISM: artificial
<220> FEATURE:
<223> OTHER INFORMATION: amplification primer

<400> SEQUENCE: 114
gtacgactca ctataggga                                                   19
```

STRATEGIES FOR GENE EXPRESSION ANALYSIS

CROSS REFERENCE TO RELATED APPLICATIONS

This application is a continuation of U.S. application Ser. No. 10/622,010, filed Jul. 16, 2003, entitled "STRATEGIES FOR GENE EXPRESSION ANALYSIS" which claims priority to and benefit of U.S. Provisional Application No. 60/397,393, filed Jul. 19, 2002, the disclosure of which is incorporated herein in its entirety for all purposes.

COPYRIGHT NOTIFICATION

Pursuant to 37 C.F.R. 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

BACKGROUND OF THE INVENTION

There are numerous biotechnology applications in which the researcher is interested the changes in gene expression of a moderate set of genes, for many hundreds or thousands of biological samples. Over the last decade, gene expression analysis has proven to be an extremely valuable tool for monitoring the state of cells, and specific pathway responses to different stimulations and environments. This ability to both broadly survey cellular activities and to track differential and dynamic responses means that expression tools have been able to provide significant insight into cancer and other disease genetics. The current state of the art in gene expression is represented by two very different technologies, microarray analysis and real-time rtPCR. Each technology offers major targeted benefits, with microarrays enabling large-scale surveys of thousands of genes for small sets of samples, and real-time rtPCR providing high sensitivity, high accuracy measurements of small sets of genes for hundreds to thousands of samples. There is, however, a technological gap that is not fully served by either of these technologies.

Multiple experimental applications exist where there is an interest and a need to screen moderate sets of genes, e.g. 20 to 100 genes for hundreds to thousands of samples. For example, to fully capture the activities of functional pathways such as apoptosis or angiogenesis, it is necessary to track between 50 and 100 genes. In fact, linear and nonlinear statistical techniques have been successfully applied to the analysis of microarray data and it is clear that correlation and cluster analysis generally collapses the responses of thousands of genes to a much smaller set of representative genes and response types. For example, Thomas et. al. (2001) *Molecular Pharmacology* 60: 1189-1194, have used this approach to identify 12 key transcripts out of 1200 that can predictively track 5 major toxicological responses. Van't Veer et. al. (2002) *Nature* 415: 530-536, recently demonstrated that a set of 70 genes, out of 25,000 tested, could provide a prognostic signature for metastases in breast cancer patients, and that the expression profile outperformed other clinical parameters used to predict disease outcome.

Another major area of interest for a high throughput gene expression assay is compound library screening. The pharmaceutical drug discovery process has traditionally been dominated by biochemical and enzymatic studies of a designated pathway. Although this approach has been productive, it is very laborious and time-consuming, and is generally targeted to a single gene or defined pathway. Today, the predominant screening assay formats fall into two categories: gene specific and phenotypic. Gene-specific screens, such as protein binding assays and reporter gene assays, focus on capturing the effects of a given compound on a single gene or protein endpoint, while phenotypic screens typically capture gross cellular changes, such as apoptosis, cell proliferation, or ion flux. Both of these screening approaches have significant value, but they are not optimal for screening compounds with respect to their effects on a multiplicity of genes involved in a complex disease, such as cancer. Gene-specific screens are too focused and cannot observe multigenic responses to perturbations. Cell-based phenotypic screens are too broad and cannot be used to differentiate the multiple pathways that can be altered to produce a phenotypic response, nor can they effectively be used to optimize and direct compound development toward specific mechanisms of action. Molecular biology and the development of gene cloning have dramatically expanded the number of genes that are potential drug targets, and this process is accelerating rapidly as a result of the progress made, e.g., in sequencing the human genome. In addition to the growing set of available genes, techniques such as the synthesis of combinatorial chemical libraries have created daunting numbers of candidate drugs for screening. In order to capitalize on these available materials, methods are needed that are capable of extremely fast and inexpensive analysis of gene expression levels. The utilization of a screen that can look at a multiplicity of genes in parallel, e.g. 5-100, can be used to overcome the deficits of these other screening approaches.

Automated high-throughput, rtPCR is one efficient approach to gene expression analysis. This approach involves isolating RNA from cells, performing multiplexed rtPCR and then running out the samples on a capillary electrophoresis unit. For example, in the context of screening a compound or chemical library of 10,000 compounds in a cell-based assay, in which the relative expression levels for 20 genes are measured, the established process involves several steps including culturing the experimental cells, typically in microtiter-plate format, isolation of the RNA from these cells, selective amplification using rtPCR, in targeted sets of 10 to 20 genes per amplification reaction, and analysis of the amplification products using capillary electrophoresis.

This process is robust and incorporates an amplification scheme that couples the use of gene-specific and universal primers to lock in the relative gene ratios for all of the genes being amplified. The method also takes advantage of the newest generation of automated, high-resolution capillary electrophoresis instruments. However, these instruments are capable of analyzing only a moderate set of samples in a given run.

Nucleic acid microarrays are available, having the benefit of assaying for sample hybridization to a large number of probes in a highly parallel fashion. They can be used for quantitation of mRNA expression levels, and dramatically surpass the above mentioned techniques in terms of multiplexing capability. These arrays comprise short DNA probes, such as PCR products, oligonucleotides, or cDNA products fixed onto a solid surface, which can then be used in a hybridization reaction with a target sample, generally a whole cell extract (see, for example, U.S. Pat. Nos. 5,143,854 and 5,807, 522; Fodor et al. (1991) Science 251:767-773; and Schena et al. (1995) Science 270:467-470), cellular RNA sample, or cDNA sample corresponding to cellular RNAs. Microarrays can be used to measure the expression levels of several thousands of genes simultaneously, generating a gene expression profile of the entire genome of relatively simple organisms. Each reaction, however, is performed with a single biological sample against a very large number of gene probes. As a consequence, microarray technology does not facilitate high throughput analysis of very large numbers of unique samples against an array of known probes. While both microarrays and real-time rtPCR techniques can be pressed into service in these important experimental areas, the fact of the matter is that neither method can do this work cost efficiently and with limited amounts of sample. As demand for gene expression data increases, it is desirable to further reduce costs per expression data point while increasing throughput. However, the scientific focus for the process should remain the same, namely, the accurate analysis of moderate sets of genes (tens to hundreds) for many thousands of samples.

Described herein are strategies for screening compound libraries involving carrying the rtPCR approach to a new level of throughput while reducing cost per data point. The approach involves replacing capillary electrophoresis readouts with microarray-format readouts. The advantages of the method are multiple and include (1) the ability to run thousands of samples in high throughput, e.g. in hours of time versus weeks, (2) the possibility to work with very small amounts of RNA, e.g. sub-nanogram amounts, opening the door to multiplexed gene expression analysis of very small amounts of tissue (such as can obtained using laser capture microdissection), and (3) the potential to run at a very low cost per data point, e.g. 1 or a few pennies per gene. This conversion of readout format can be directly integrated into the current rtPCR process enabling a smooth transition to this higher throughput platform. This change in methodology also modifies the existing platform for further advances based on the parallelization of sample processing in the microarray format, modifications that can lead to increased economies in reagent usage, time and labor, while maintaining a focus on measuring the gene expression response for moderate sets of genes across numerous biological samples.

SUMMARY OF THE INVENTION

The present invention provides methods for screening compound libraries, e.g., to identify compounds with potential therapeutic utility. In the methods of the present invention, expression products derived from a plurality of biological samples or sources are simultaneously detected in a microarray format. Expressed RNA samples are obtained from a plurality of biological samples which have been exposed, e.g., contacted or treated with members of a compound library, such as a library of chemical compositions. Following collection of the expressed RNA samples, by isolating total cellular RNA, or a population of RNAs such as messenger RNAs (mRNAs), a population of nucleic acids (or a subset of RNA species, i.e., polynucleotide sequences) corresponding to each of the samples is arrayed to produce a nucleic acid array. Frequently, amplification products corresponding to the expressed nucleic acids are arrayed. Alternatively, RNA or cDNA corresponding to the expressed nucleic acids can be arrayed. Optionally, the nucleic acids undergo one or more purification step prior to arraying.

A plurality of defined sequence probes, e.g., probes each having a unique polynucleotide sequence, such as a set of genes, disease related targets, or the like, each of which is capable of giving rise to a different detectable signal is then hybridized simultaneously to the nucleic acid array. A defined sequence probe, in the context of the invention, can be, e.g., an oligonucleotide, a cDNA, an amplification product or a restriction fragment. In various embodiments, the defined sequence probes are capable of generating different signals produced by different fluorescent labels or fluorophores, chromophores, electrophores, radioactive nuclides, chemically reactive moieties, amplifiable signal elements and/or enzymes or ligands. Signals corresponding to hybridization of the defined sequence probes to the nucleic acid array are then detected, and, typically quantitated. Optionally, the signals are compared between probes or between samples.

Amplification of the expressed nucleic acids is typically performed prior to arraying the nucleic acids. Commonly, the amplification step involves one or more nucleic acid amplification, e.g., by a PCR, TMA, NASBA or RCA reaction. Optionally, the PCR is an rtPCR that couples reverse transcription and amplification of the expressed RNA samples. The amplification can be either a global amplification or a selective (e.g., target specific) amplification of one or more species in the expressed RNA sample(s). For example, amplification can be performed by multiplex PCR using a plurality of gene specific primers. Optionally, the multiplex PCR also includes a universal or semi-universal primer. In some embodiments, the gene specific primers also include a universal priming sequence (universal primer). A multiplex PCR in the context of the invention results in amplification of a plurality of nucleic acid species or products, typically between about 5 and about 100 different polynucleotide sequences, or between about 10 and about 50 polynucleotide sequences. Each expressed RNA sample can be amplified in two or more target specific amplification arrays, and, for example, spatially arrayed in two or more locations on a physical array. Optionally, a plurality of defined sequence probes each of which specifically hybridizes to the products of a different target specific amplification reaction is hybridized to the array. In some embodiments, amplification products are pooled for arraying.

Optionally, a post-hybridization amplification step can be performed to increase the signal to noise ratio and increase sensitivity of detection of the signal corresponding to hybridization of the defined sequence probes and the nucleic acid array. Amplification can be facilitated by the inclusion of an amplifiable signal element into the probe. In some embodiments, the amplifiable signal element is an oligonucleotide sequence that can be amplified, e.g., by branched DNA amplification (BDA), by rolling circle amplification (RCA), by using DNA dendrimer probes, or variations of these procedures. Alternatively, the signal can be amplified by an enzymatic or catalytic reaction that gives rise to a detectable product.

In various embodiments of the invention, expressed RNA samples for analysis are obtained from a variety of biological sources or samples which have been exposed to or treated with members of a library of compositions or agents of potential therapeutic value. A biological sample can be either prokaryotic or eukaryotic, and can be cells, such as primary cells or a cell line, e.g., an immortalized cell line. The choice of cell lines is typically determined by the nature of the organism or cell which is the target of the therapeutic agent sought in the screening endeavor. Alternatively, a biological sample can be a tissue or organ biopsy, or, in some cases, an organism, or collection of organisms. Prior to obtaining the expressed RNA sample form the biological sample, the biological sample is treated, contacted or exposed to one or more agent, compound or composition prior to sample collection. For example, subpopulations of a cell line can each be treated with a different member of a collection of compositions, e.g., a chemical or compound library.

As numerous samples can be analyzed simultaneously, favorable embodiments involve obtaining and analyzing expression data from a large number of biological samples, e.g., greater than about 100 samples, each of which has been treated with (or contacted with or exposed to) a member of a compound library. Usually, each biological sample is treated with a different member of the compound library. Typically, more than 500 samples are arrayed and analyzed. Commonly, in excess of 1000 samples are simultaneously arrayed and analyzed. Frequently, in excess of about 2000 samples are analyzed, and in certain embodiments, greater than about 10,000 biological samples are analyzed. Alternatively, the methods are directed toward simultaneous analysis of expression data from a small number of samples, e.g., from between 2 and about 20 samples, or a moderate number of samples, such as between about 20 and about 100 samples.

A variety of nucleic acid array formats can be employed in the context of the present invention. In some embodiments, the arrays are solid phase arrays, i.e., the nucleic acids are arrayed on one or more solid phase surface. In some embodiments, the nucleic acids corresponding to expressed RNA samples are arrayed on a two dimensional solid phase surface. In alternative embodiments, the nucleic acids are arrayed on a plurality of solid phase surfaces, such as beads, spheres, pins, or optical fibers.

Solid phase arrays surfaces can include a variety of materials, and in various embodiments of the invention, the array surface is composed, e.g., of glass, coated glass, silicon, porous silicon, nylon, ceramic or plastic.

An aspect of the invention relates to methods for determining relative gene expression for a plurality of expression products in two or more biological samples, e.g., a control sample and one or more biological samples which have been exposed to or contacted with a member of a compound library. These methods involve obtaining expressed RNA samples from a plurality of different biological samples and arraying sets of nucleic acids corresponding to the expressed RNA samples, or a subset of species in the expressed RNA samples. A plurality of defined sequence probes, each comprising a different polynucleotide sequence, and each of which is capable of generating a different detectable signal is then hybridized to the array, and a signal corresponding to the hybridization between the probes and the array is detected and quantitated. Hybridization signals are then compared between biological samples for a plurality of the defined sequence probes.

In the methods for screening a compound library to identify a compound with a physiological effect on a biological sample, the biological samples can include members of a population of experimental organisms, multiple subpopulations of a primary cell isolate or cell line, tissue samples (e.g., sub-samples of a tissue, samples of identical tissues, or samples of related tissues) or extracts made from tissue(s) or cells. A biological sample can be either prokaryotic or eukaryotic. A compound library can be a chemical or biochemical (or combined) composition library, such as a compound collection library, a combinatorial chemical library, a scaffold-focused chemical library, a target focused chemical library, an antibody library, a biological library, a natural product library, an antisense agent library, an iRNA library, a siRNA library, a ribozyme library, a peptide library, and a combinatorial nucleic acid oligomer library.

Typically an expressed RNA samples is also obtained from an untreated biological sample (or a zero time point sample, or other control sample). Nucleic acids corresponding to the expressed RNA samples are arrayed to produce a nucleic acid array, and a plurality of defined sequence probes each capable of giving rise to a different detectable signal is hybridized to the array. Signals corresponding to hybridization between the probes and the array are quantitated and differences in expression between treated and control hybridization signals are evaluated to identify compounds that exert a physiological effect on the biological sample, e.g., by exerting an effect on one or more biological targets.

Quantitated hybridization signals can differ either qualitatively or quantitatively from one or more control hybridization signals (e.g., an internal control hybridization signal), and can be either increased or decreased relative to a control hybridization signal. For example, one or more defined sequence probe corresponding to genes of interest as well as a control probe, such as a probe corresponding to a housekeeping gene, are hybridized to the array. The resulting hybridization signals are detected, quantitated and the relative expression between the gene(s) of interest and the control are determined. In the analysis of multiple duplicate arrays, consistency can be maintained by differing the gene specific probes between arrays while hybridizing the multiple arrays to the same control, e.g., housekeeping, gene. In some embodiments, differences between the hybridization signals are evaluated by performing at least one statistical analysis. For example, a quantitative difference can be at least one standard deviation, or two standard deviations from a reference or control hybridization signal.

The methods of the invention optionally involve recording data representative of one or more of the hybridization signals (e.g., indicative of an absolute or relative quantitation of a hybridization signal for the plurality of samples) in a database. Commonly, the database is in a computer or computer readable medium.

The invention also provides hybridization systems including an array of nucleic acids corresponding to a plurality of expressed RNA samples each of which is obtained from a different biological sample which have been contacted with members of a compound library, and a plurality of defined sequence probes each capable of generating a different detectable signal. The nucleic acid array can include any one or more of RNA, cDNA, or amplification products corresponding to expressed RNAs from biological samples. The plurality of defined sequence probes can be any set of probes having different polynucleotide sequences. In certain favorable embodiments, the probes include a set of genes, such as genes that are disease related targets.

The invention also includes integrated systems including the hybridization systems of the invention and components or modules for performing the methods of the invention, as well as kits incorporating components for the systems and methods of the invention.

DETAILED DESCRIPTION

Figure 1:
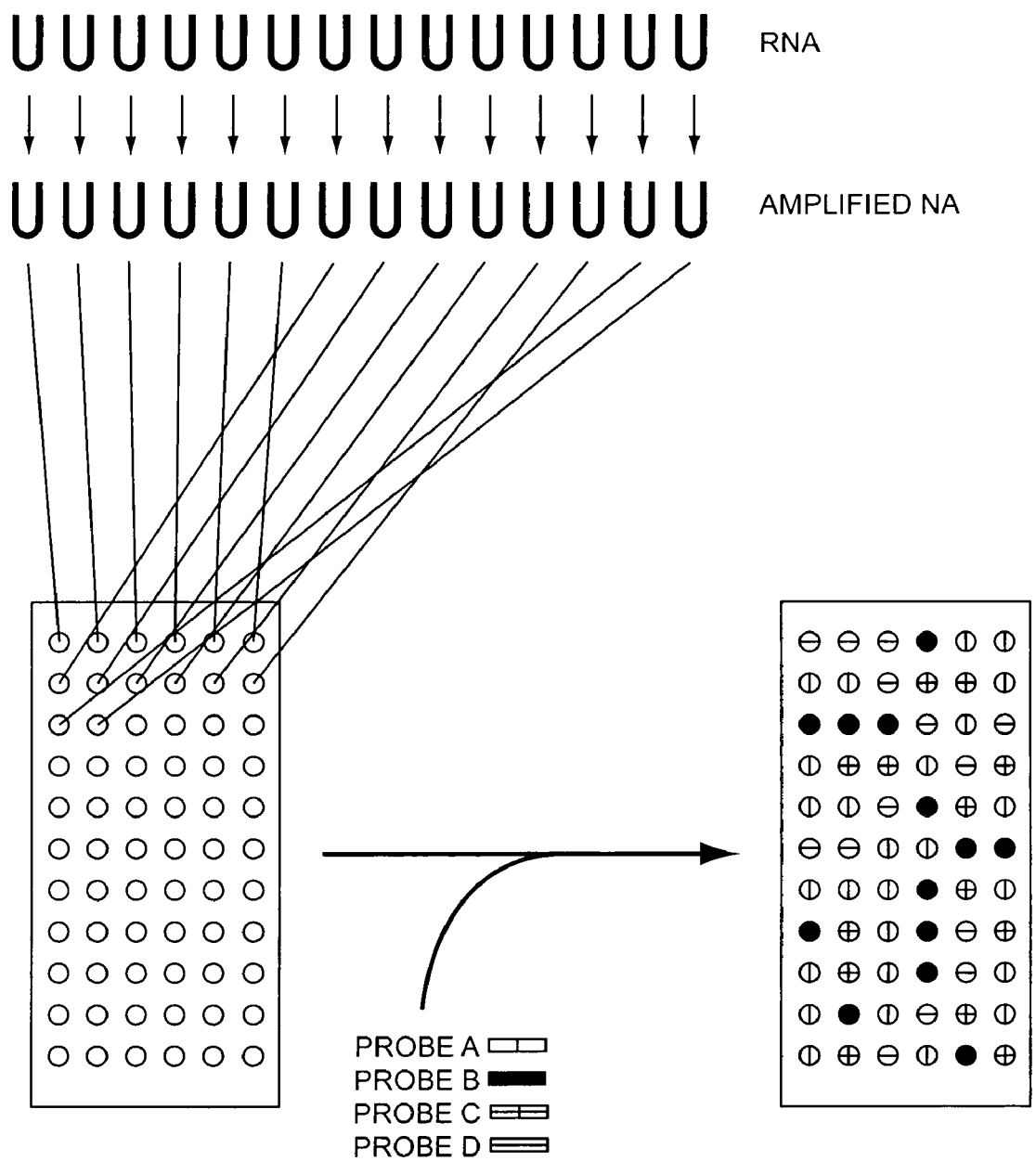
FIG. 1 schematically illustrates arraying of nucleic acids corresponding to expressed RNAs derived from multiple biological samples, and hybridizing with a plurality of differently labeled probes.

The present invention involves screening compound libraries for drug discovery by "flipping" the standard microarray paradigm. Microarray formats typically involve the spatial organization of numerous probe sequences on a solid phase surface, and application of a single labeled nucleic acid sample to the microarray. A signal corresponding to the hybridization between the labeled test sample and the probe array is then detected, most commonly using automated array detection devices. This technology permits the analysis of gene expression for numerous query sequences across a single biological sample. Multiple duplicate arrays are tested with multiple samples, or the same array is contacted sequentially with multiple nucleic acid samples to analyze multiple biological samples. In the context of drug discovery efforts, this permits a broad survey of a compound's effects on a biological system from which the RNA sample is derived. However, this approach is prohibitively expensive the purpose of evaluating the effects of numerous compounds.

In contrast, the present invention provides methods for analyzing gene expression in which nucleic acids corresponding to RNA samples derived from a number of biological samples, which have been exposed to (or contacted or treated with) members of a compound library are assembled into an array, and multiple gene specific probes are hybridized to these sample arrays. In other words, the samples are placed on the surface and the probes are in solution.

Standard microarrays differentiate between the genes being monitored by assigning a unique spatial placement to each of the gene specific probes on the microarray surface. The methods described herein for "flipping" the microarray, distinguish between different gene specific probes by differential labeling of the individual probes (e.g., by labeling different probes with fluorescent labels that can be uniquely identified by their absorption/emission properties). While this approach limits the number of probe sequences (e.g., genes) that can be analyzed in any single array reaction, it facilitates the use of the spatial arraying dimensions for the high level of multiplexing of samples (e.g., samples treated with members of a large compound library) in a single experiment. Automated, or semi-automated duplication procedures are employed to increase the number of sequences analyzed as desired, according to the number of compounds to be screened.

Gene expression profiles of biological samples exposed to members of a compound library are generated, allowing the practitioner to determine, in a gene specific manner, the effects of the individual members of the library on a physiological system or biological sample of interest. However, several other applications are also possible, as would be apparent to one skilled in the art from a reading of this disclosure. For example, the methods of the present invention can be used to investigate the profile and expression levels of one or more members of complex gene families, e.g., in response to treatment with compositions under evaluation as potential therapeutic agents, with respect to both therapeutic and toxicologic properties. As an illustration, cytochrome P450 isozymes form a complex set of related enzymes that are involved in detoxification of foreign substances in the liver (Ortiz de Montellano (1995) Cytochrome P450 Structure Mechanism and Biochemistry, Plenum Press, New York). The various isozymes in this family have been shown to be specific for different substrates. Design of target-specific probes that hybridize to variant regions in the genes provides an assay by which their relative levels of induction in response to drug treatments can be monitored. Other examples include monitoring expression levels of alleles with allele-specific probes, or monitoring mRNA processing with probes that specifically hybridize to a spliced or unspliced region, or to splice variants. One skilled in the art could envision other applications of the present invention that would provide a method to monitor genetic variations or expression mechanisms, e.g., relevant to responses to drug efficacy or toxicity.

DEFINITIONS

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise.

Unless defined otherwise, all technical and scientific terms used herein have the same meaning as commonly understood by one of ordinary skill in the art to which the invention pertains. Although any methods and materials similar or equivalent to those described herein can be used in the practice or testing of the present invention, the currently preferred materials and methods are described herein. In describing and claiming the present invention, the following terminology will be used in accordance with the definitions set out below.

"Expression products" are ribonucleic acid (RNA) or polypepetide products transcribed or translated, respectively, from a genome or other genetic element. Commonly, expression products are associated with genes having biological properties. Thus, the term "gene" refers to a nucleic acid sequence associated with a biological properties, e.g., encoding a gene product with physiologic properties. A gene optionally includes sequence information required for expression of the gene (e.g., promoters, enhancers, etc.).

The term "gene expression" refers to transcription of a gene into an RNA product, and optionally to translation into one or more polypeptide sequences. The term "transcription" refers to the process of copying a DNA sequence of a gene into an RNA product, generally conducted by a DNA-directed RNA polymerase using DNA as a template.

The term "nucleic acid" refers to a polymer of ribonucleic acids or deoxyribonucleic acids, including RNA, mRNA, rRNA, tRNA, small nuclear RNAs, cDNA, DNA, PNA, RNA/DNA copolymers, or analogues thereof. Nucleic acid may be obtained from a cellular extract, genomic or extragenomic DNA, viral RNA or DNA, or artificially/chemically synthesized molecules.

The term "RNA" refers to a polymer of ribonucleic acids, including RNA, mRNA, rRNA, tRNA, and small nuclear RNAs, as well as to RNAs that comprise ribonucleotide analogues to natural ribonucleic acid residues, such as 2-O-methylated residues.

The term "cDNA" refers to complementary or "copy" DNA. Generally cDNA is synthesized by a DNA polymerase using any type of RNA molecule (e.g., typically mRNA) as a template. Alternatively, the cDNA can be obtained by directed chemical syntheses.

The term "amplified product" or "amplified nucleic acid" refers to a nucleic acid generated by any method of nucleic acid amplification.

The term "complementary" refers to nucleic acid sequences capable of base-pairing according to the standard Watson-Crick complementary rules, or being capable of hybridizing to a particular nucleic acid segment under relatively stringent conditions. Nucleic acid polymers are optionally complementary across only portions of their entire sequences.

The term "hybridization" refers to duplex formation between two or more polynucleotides, e.g., to form a double-stranded nucleic acid. The ability of two regions of complementarity to hybridize and remain together depends of the length and continuity of the complementary regions, and the stringency of hybridization conditions.

A "defined sequence probe" is a nucleic acid probe having a single polynucleotide sequence.

The term "synthetic probe" is used to indicate that the probe is produced by one or more synthetic or artificial manipulations, e.g., restriction digestion, amplification, oligonucleotide synthesis, cDNA synthesis, and the like.

The term "label" refers to any detectable moiety. A label may be used to distinguish a particular nucleic acid from others that are unlabeled, or labeled differently, or the label may be used to enhance detection.

The term "primer" refers to any nucleic acid that is capable of hybridizing at its 3' end to a complementary nucleic acid molecule, and that provides a free 3' hydroxyl terminus which can be extended by a nucleic acid polymerase.

The term "template" refers to any nucleic acid polymer that can serve as a sequence that can be copied into a complementary sequence by the action of, for example, a polymerase enzyme.

The term "target," "target sequence," or "target gene sequence" refers to a specific nucleic acid sequence, the presence, absence or abundance of which is to be determined. In a preferred embodiment of the invention, it is a unique sequence within the mRNA of an expressed gene.

The term "target-specific primer" refers to a primer capable of hybridizing with its corresponding target sequence. Under appropriate conditions, the hybridized primer can prime the replication of the target sequence.

The term "semi-universal primer" refers to a primer that is capable of hybridizing with more than one, but not all, of the target-specific primers in a multiplexed reaction.

The term "universal primer" refers to a replication primer comprising a universal sequence.

The term "universal sequence" refers to a sequence contained in a plurality of primers, but preferably not in a complement to the original template nucleic acid (e.g., the target sequence), such that a primer composed entirely of universal sequence is not capable of hybridizing with the template.

The term "reference sequence" refers to a nucleic acid sequence serving as a target of amplification in a sample that provides a control for the assay. The reference may be internal (or endogenous) to the sample source, or it may be an externally added (or exogenous) to the sample. An external reference may be either RNA, added to the sample prior to reverse transcription, or DNA (e.g., cDNA), added prior to PCR amplification.

The term "multiplex reaction" refers to a plurality of reactions conducted simultaneously in a single reaction mixture, and includes, for example, multiplex amplification and multiplex hybridization reactions.

The term "multiplex amplification" refers to a plurality of amplification reactions conducted simultaneously in a single reaction mixture.

In the context of the present invention, the term "simultaneously" means that the reaction, e.g., a hybridization reaction, occurs at substantially the same time. For example, reagents to be hybridized, such as multiple defined sequence probes are contacted at the same time and/or in the same solution with target nucleic acids, e.g., an array of nucleic acids.

In the context of the present invention, an "amplifiable signal element" is a component of a probe that facilitates amplification of a signal following hybridization of the probe to a target sequence.

The term "gene expression data" refers to one or more sets of data that contain information regarding different aspects of gene expression. The data set optionally includes information regarding: the presence of target-transcripts in cell or cell-derived samples; the relative and absolute abundance levels of target transcripts; the ability of various treatments to induce expression of specific genes; and the ability of various treatments to change expression of specific genes to different levels.

The term "quantitating" means to assign a numerical value, e.g., to a hybridization signal. Typically, quantitating involves measuring the intensity of a signal and assigning a corresponding value on a linear or exponential numerical scale.

The term "relative abundance" or "relative gene expression levels" refers to the abundance of a given species relative to that of a second species. Optionally, the second species is a reference sequence.

The term "treatment" refers to the process of subjecting (i.e., treating) one or more cells, cell lines, tissues, or organisms to a condition, substance, or agent (or combinations thereof) that may cause the cell, cell line, tissue or organism to alter its gene expression profile. A treatment may include a range of chemical concentrations and exposure times, and replicate samples may be generated. The term "chemical treatment" refers to the process of exposing (or contacting) a cell, cell line, tissue or organism to (or with) a chemical or biochemical compound (or library of compounds) that has/have the potential to alter its gene expression profile.

The term "platform" refers to the instrumentation method used for sample preparation, amplification, product separation, product detection, or analysis of data obtained from samples.

The terms "microplate," "culture plate," and "multiwell plate" interchangeably refer to a surface having multiple chambers, receptacles or containers and generally used to perform a large number of discreet reactions simultaneously.

The term "high throughput format" refers to analyzing more than about 10 samples per hour, preferably about 50 or more samples per hour, more preferably about 100 or more samples per hour, most preferably about 250, about 500, about 1000 or more samples per hour.

The term "miniaturized format" refers to procedures or methods conducted at submicroliter volumes, including on both microfluidic and nanofluidic platforms.

Overview

A schematic outline of an exemplary method of the invention is illustrated in FIG. 1. Multiple RNA samples obtained from biological samples which have been treated with members of a library of compositions of interest in a screening effort aimed at identifying potential therapeutic agents. Usually such libraries are large collections of compounds or compositions, ranging from hundreds to many thousands of different compositions, e.g., from about 500 to many thousands of compounds. Typically, RNA samples arranged (or arrayed) in microtiter plates provide the templates for generating a series of nucleic acid (NA) products that are then arrayed in one or more microarray, for example, in the format of microarray slides. The nucleic acid products in the form of amplification products are commonly produced by rtPCR. For example, in a favorable embodiment the rtPCR performs a multiplexed targeted (e.g., target or gene specific) amplification reaction. Alternatively, RNA or cDNA products are arrayed. Typical microarray slides contain between a thousand and 20,000 nucleic acid "spots." Each nucleic acid sample is assigned a unique location on the microarray. Therefore, as many as 20,000 different nucleic acid, e.g., amplification product, samples (corresponding to expressed RNAs from as many as 20,000 unique biological samples, e.g., samples treated with 20,000 individual members of a composition library) can be arrayed and analyzed on a single microarray slide. In the example shown in FIG. 1, 4 different genes are analyzed using 4 different defined sequence oligonucleotide probes. The different probes are labeled with 4 different labels that can be uniquely detected and quantitated in the array reader.

Figure 2:
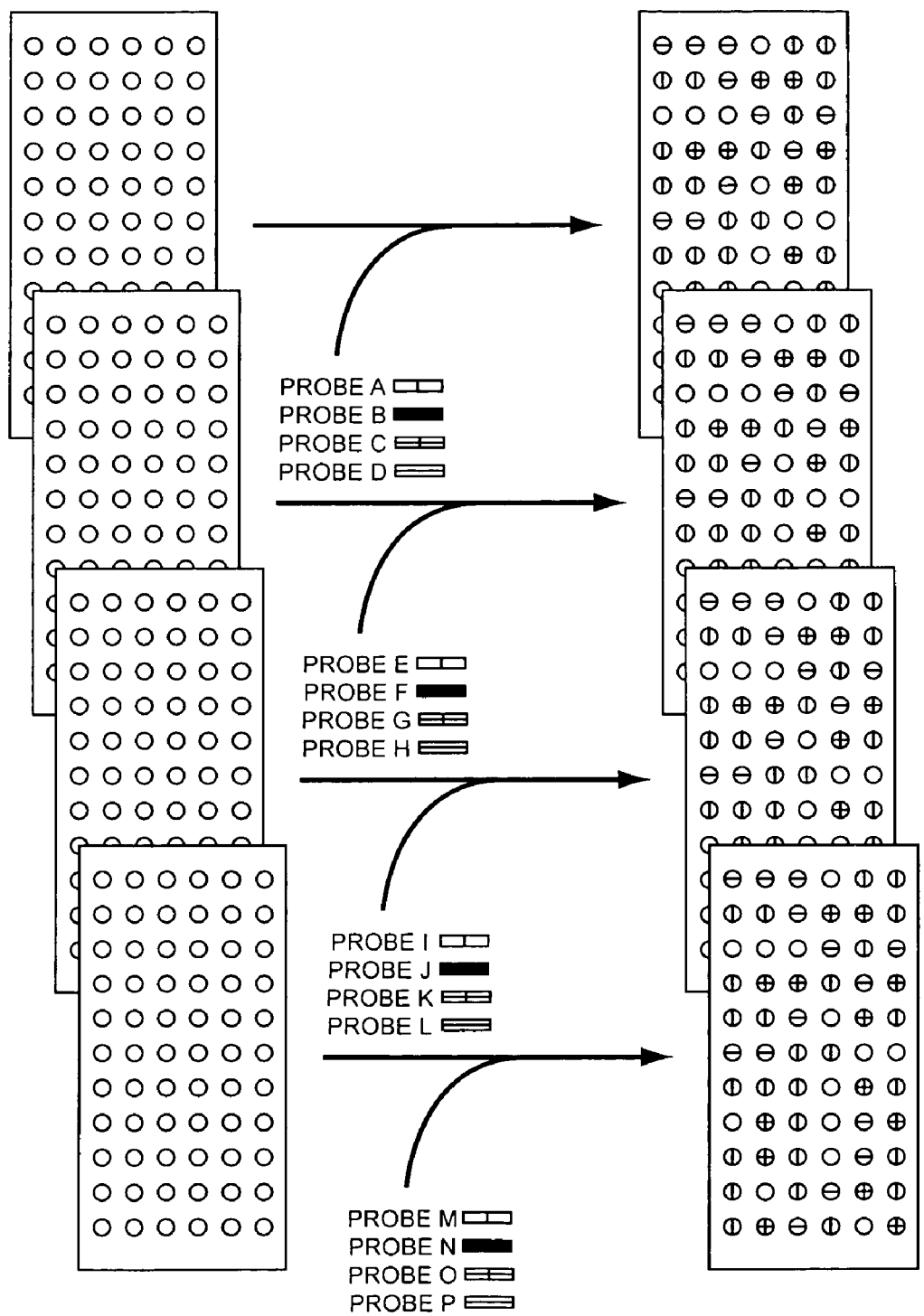
FIG. 2 schematically illustrates duplication of an array to increase probe diversity.

The ability to analyze 4 different genes for 20,000 samples on a given slide may seem limited in terms of gene depth. However, it is trivial to replicate a given slide using existing slide printing instruments to generate upwards of 100 or more slides per set of samples. This replication process is shown schematically in FIG. 2. The use of replicate microarrays makes it possible to analyze numerous different query sequences against the same RNA samples. The processes of printing, probing and scanning the microarray plates is a near parallel process, therefore, it takes nearly the same time and resources to analyze 20 (or 100) plates as it does a single plate.

Figure 3:
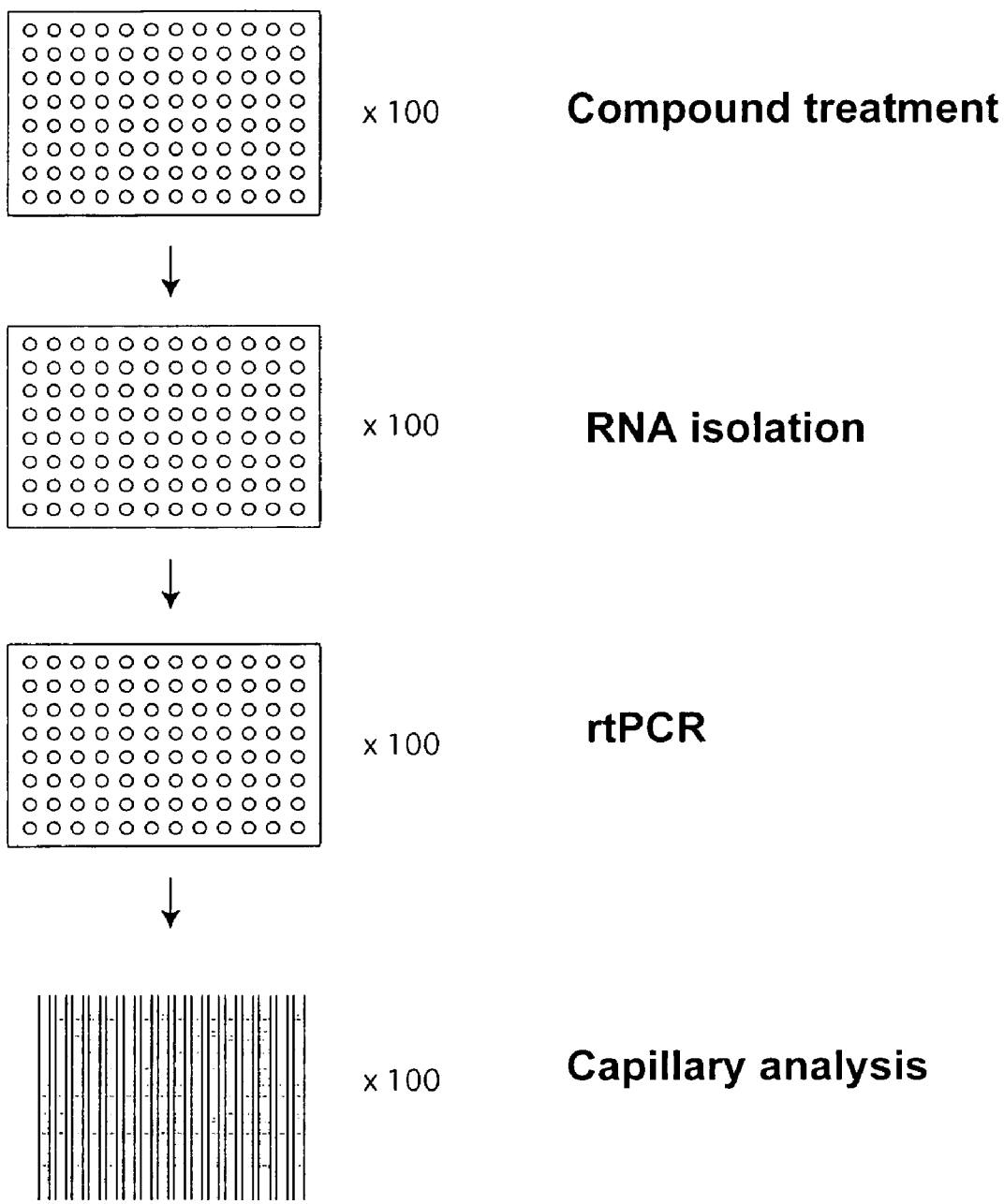
FIG. 3 schematically illustrates library screening using capillary electrophoresis technology.

For comparison, an established process utilizing capillary electrophoresis is shown schematically in FIG. 3. The capillary electrophoresis process is contrasted with the methods of the present invention in the context of screening a compound or chemical library of 10,000 compounds in a cell-based assay, in which the relative expression levels for 20 genes are measured providing 200,000 data points. The established capillary electrophoresis process involves several steps, including culturing of the experimental cells, typically in microtiter-plate format (i.e., 10,000 compounds in 100 plates), isolation of the RNA from these cells, selective amplification using rtPCR, in targeted sets of 10 to 20 genes per amplification reaction, and analysis of the amplification products using capillary electrophoresis.

This process is robust and incorporates an amplification scheme that couples the use of gene-specific and universal primers to lock in the relative gene ratios for all of the genes being amplified. The method also takes advantage of the newest generation of automated, high-resolution capillary electrophoresis instruments. But while these instruments are state of the art, they still only run a moderate set of samples, e.g., 2×16 samples for 20 genes, in a given run, necessitating approximately 300 runs and 30 minutes each. Thus, capillary analysis using current capabilities, e.g., on 1 ABI3100 analyzer, takes more than one week.

Figure 4:
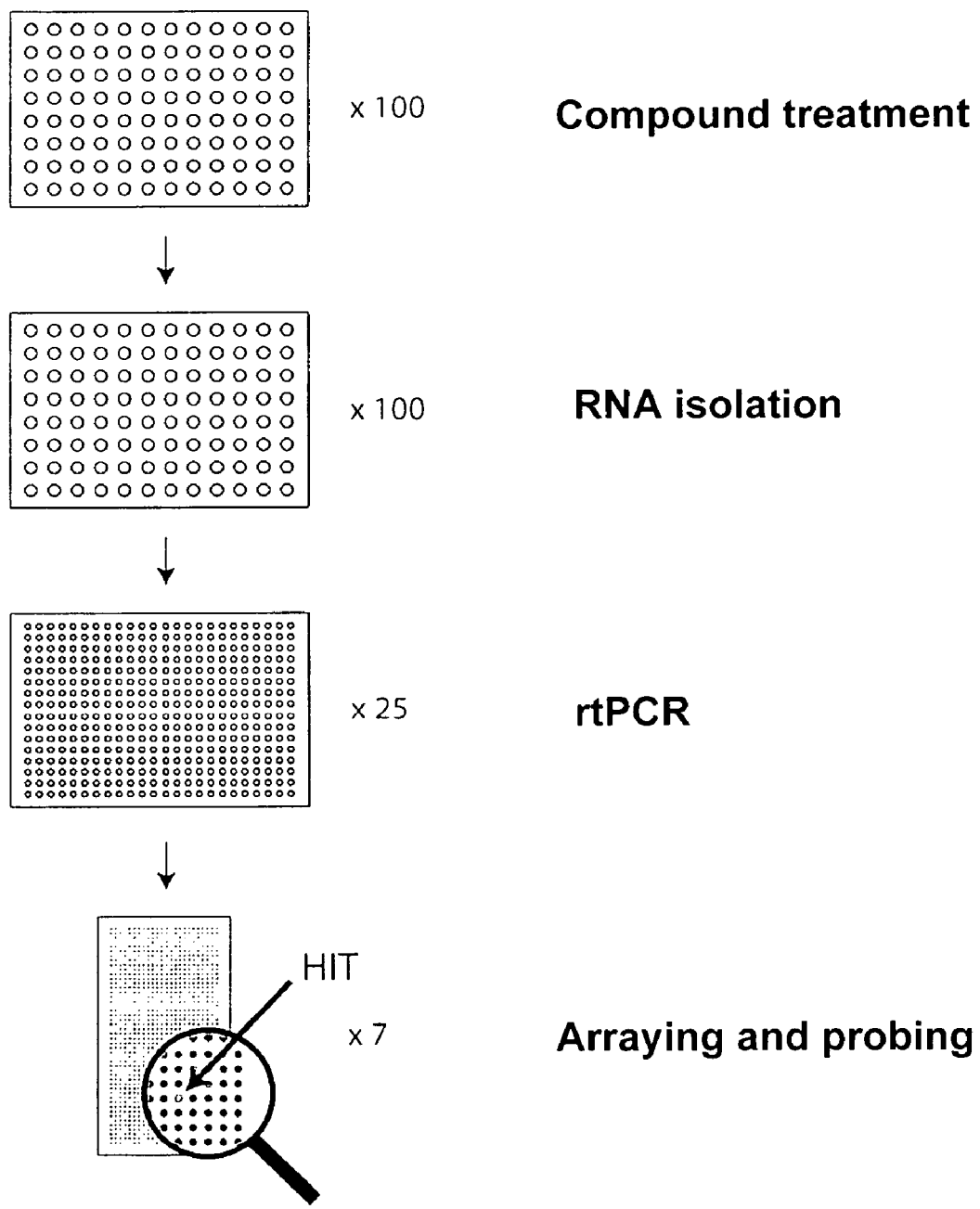
FIG. 4 schematically illustrates library screening by hybridizing a plurality of differently labeled probes to a nucleic acid microarray.

An exemplary method for screening a compound library according to the present invention is shown schematically in FIG. 4. The process resembles the existing capillary electrophoresis process in that it involves RNA isolation, and uses an rtPCR-based amplification scheme, in which amplification is performed in, e.g., 384 well plates. The process differs from the current methodology following amplification of the RNA sample, or alternative production of a nucleic acid sample corresponding to the RNA sample. Instead of using a capillary electrophoresis instrument to detect and quantitate the amplified products, the process involves spotting all of the amplified products onto microarray slides. Depending on the number of genes to be analyzed, the amplified products are deposited onto one or more slides. For example, if one wishes to analyze 20 genes coming from a single rtPCR reaction, one needs to deposit or "print" the amplified products down onto 7 microarray slides, wherein each array is used to analyze three genes plus a control or reference gene.

These modifications of existing procedures lead to a dramatic increase in throughput. For example, 10,000 samples can be run through the post PCR process in a single 24-hour period versus the one to two weeks necessary to run all of the samples on a single capillary electrophoresis instrument. In scenarios where the number of genes to be analyzed increases, this differential grows even larger. For example, the analysis of 100 genes would increase the time to completion of the analysis in the capillary format 5-fold to 5-10 weeks, while the time associated with running 35 microarrays remains a matter of a couple of days. The cost savings are also significant with the reagent costs associated with running microarrays being conservatively estimated to be less that half that of capillaries. Additionally, the present invention reduces the overall number of steps involved in performing multi-gene expression analysis on numerous biological samples.

Figure 5:
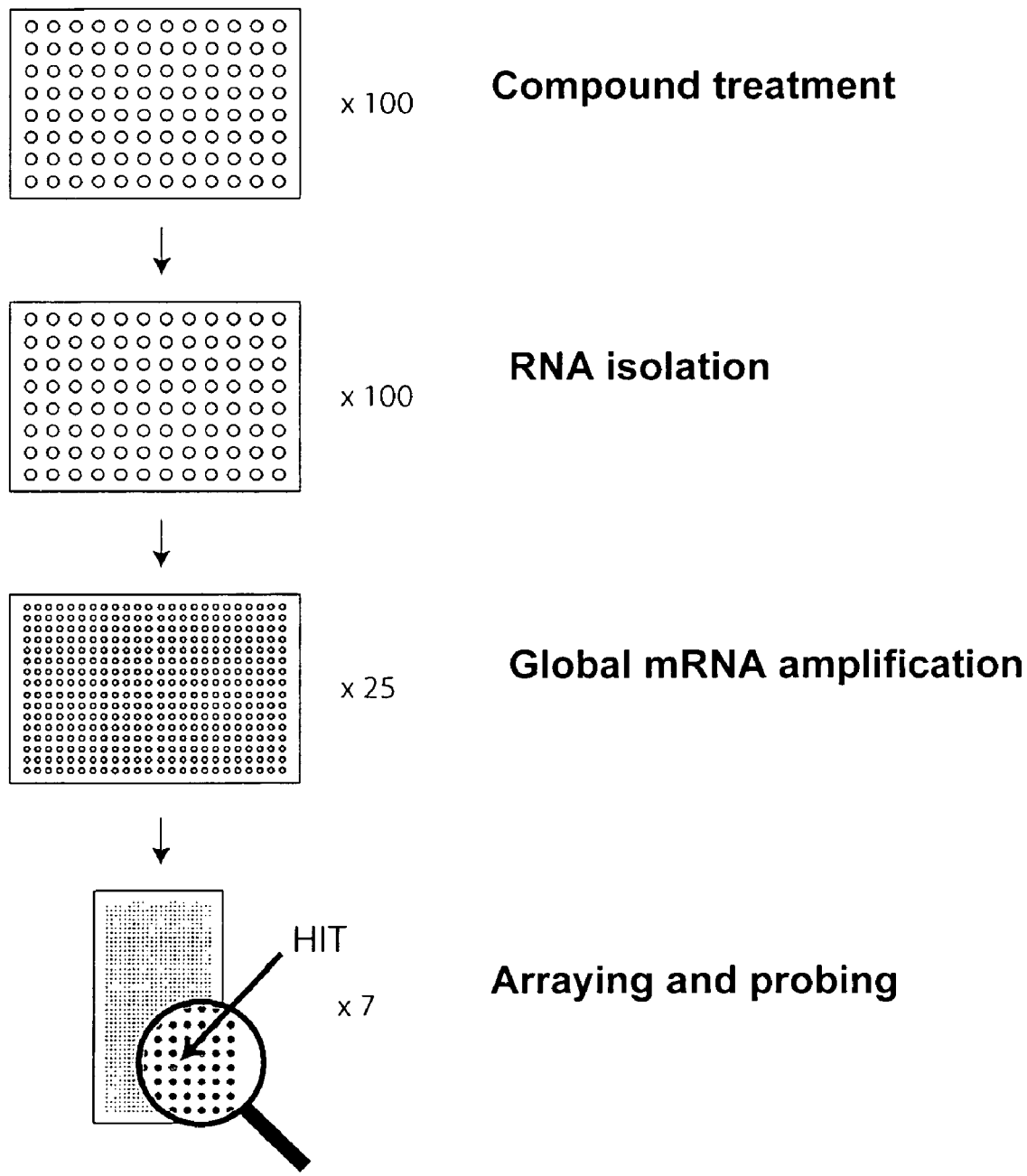
FIG. 5 schematically illustrates a global amplification approach for nucleic acid arrays.

The substitution of microarrays also offers several additional benefits. As illustrated in FIG. 5, because the transition to microarrays eliminates the need to size individual PCR products, a universal or global mRNA amplification scheme (e.g., as described by Kurn or Eberwine, infra, or by Rolling Circle Amplification) can be utilized. The advantage of using a global amplification scheme is most apparent in cases where one wishes to regularly analyze more than 20-30 genes, the practical limit for PCR, from a single sample.

Figure 6:
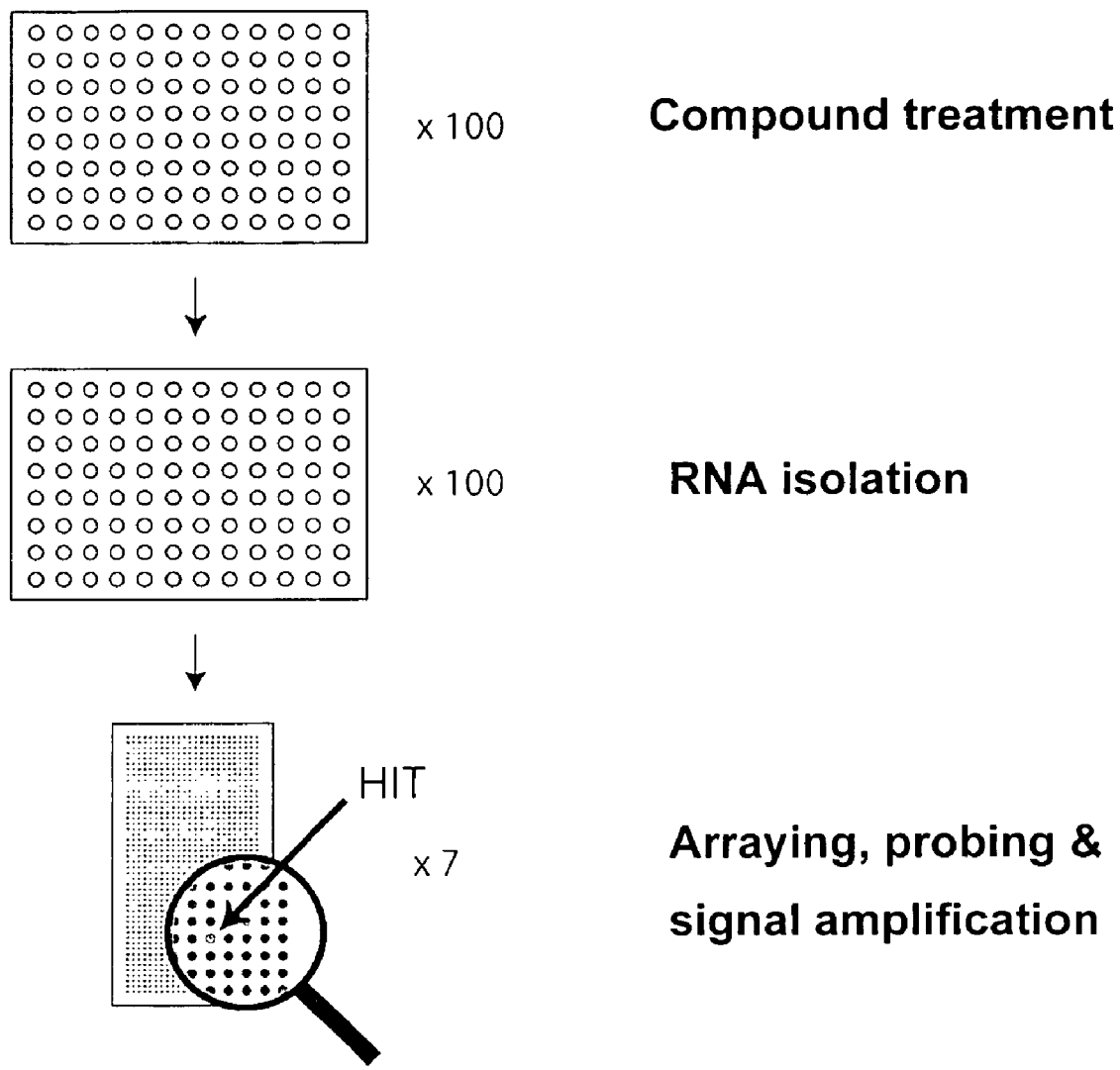
FIG. 6 schematically illustrates a protocol involving on chip signal amplification.

FIG. 6, illustrates an exemplary strategy in which post hybridization signal amplification is performed to increase sensitivity of analysis, e.g., with genes expressed at low levels. In an alternative embodiment post hybridization signal amplification replaces sample amplification, dramatically reducing reagent and labor costs associated with running 10,000 individual amplification reactions, e.g., PCR. In these embodiments, arraying, probing and signal amplification can be performed in less than 24 hours for 10,000 or more compounds.

One advantage of a signal amplification scheme is that amplification is performed late in the process after compression of the sample set from, e.g., 25 384-well microtiter-plates to 7 microarray slides. This compression in sample format converts the amplification from 10,000 individual reactions to just 7, reducing sample-to-sample variability in the data, since the treatment conditions between samples are more nearly identical.

Figure 7:
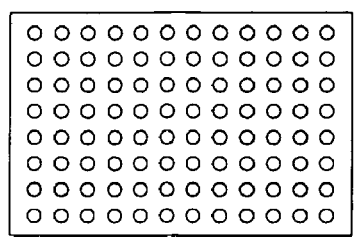
FIG. 7 schematically illustrates a procedure for isolating RNA on the array coupled with signal amplification.
Figure 7:
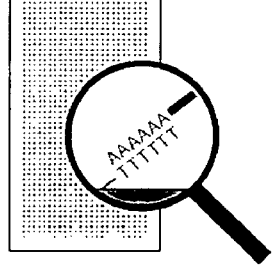
Figure 7:
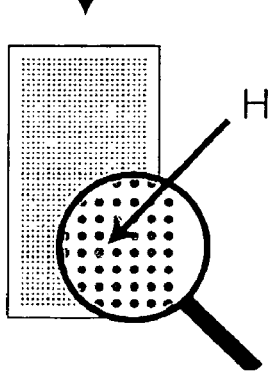

Alternatively or additionally, the RNA isolation process can be modified to reduce processing. The utilization of a microarray format makes it possible to create a miniaturized and highly simplified approach to mRNA capture and isolation, as shown in FIG. 7. Glass slides used to create microarrays are routinely coated with different compounds and chemical functionalities to alter the binding and adherence properties of the slide. Through the use of existing chemistries it is possible to coat glass slides with polythymidine (polyT). Crude cell lysates (or some fraction thereof, containing the mRNA) can be directly spotted onto the polyT-coated slides. The mRNA is annealed to the polyT, and the unbound material is washed away. Thus, the entire set of steps for processing, handling and detecting the RNA occurs on the microarray slide. This simplification of the process represents a dramatic reduction in sample handling steps and reagent usage and creates a gene expression analysis platform that is capable of very high throughputs and can be run at an extremely low cost per data point.

Screening Libraries of Compositions

The present invention provides methods for identifying compounds, e.g., chemicals, that have a physiological effect on one or more physiological processes in a biological system, such as a cell (e.g., a cell line in culture), tissue or organism. In one favorable embodiment, a chemical or compound library is screened according to the methods of the invention. One favorable application of the present invention is in the screening of large compound libraries for the purpose of identifying agents with potential therapeutic application, e.g., activity relevant to a physiologic, metabolic or genetic pathway related to preventing or treating a disease state or condition. Alternative embodiments include screening compound libraries for compounds for purposes other than identifying therapeutic agents, e.g., agents with effects on a biological system unrelated to a disease state. Typically, biological samples, such as samples of a cell line in culture, are exposed to, or treated, e.g., contacted, with a member of a chemical or compound library. Following exposure, an expressed RNA sample is recovered from each treated sample, and analyzed as described herein. Typically, a large number of expressed RNA samples derived from biological samples, for example, a large number of samples each corresponding to a population of the same cell line, each of which has been treated with a different member of the compound library, are spatially arrayed, e.g., on a glass microarray slide and hybridized to a plurality of probes of interest, e.g., corresponding to genes encoding components of a biochemical pathway of interest. Usually, anywhere from about 100 (or 200, or 500) to several thousand, e.g., about 10,000, about 20,000 different expressed RNA samples corresponding to samples (i.e., populations) of a cell line, each of which is exposed to one (or more) members of a library of compositions, is arrayed and analyzed according to the methods of the invention.

For example, a cell or cell line can be treated with or exposed to one or more characterized or uncharacterized chemical libraries (chemical compound libraries), chemical or biochemical constituents, e.g., pharmaceuticals, pollutants, DNA damaging agents, oxidative stress-inducing agents, pH-altering agents, membrane-disrupting agents, metabolic blocking agent; a chemical inhibitors, cell surface receptor ligands, antibodies, transcription, promoters/enhancers/inhibitors, translation promoters/enhancers/inhibitors, protein-stabilizing or destabilizing agents, various toxins, carcinogens or teratogens, proteins, lipids, or nucleic acids. The libraries include combinatorial chemical libraries, scaffold-focused chemical libraries, target focused chemical libraries, biological libraries, natural product libraries, antisense agent libraries, iRNA libraries, siRNA libraries, ribozyme libraries, peptide libraries and combinatorial nucleic acid oligomer libraries, etc. As will be appreciated by one skilled in the art, the number of classes of compounds and/or compound analogues that can be screened for a physiological effect on a biological sample is extensive, and includes, but is not limited to, the following groups of compounds: ACE inhibitors; anti-inflammatory agents; anti-asthmatic agents; antidiabetic agents; anti-infectives (including but not limited to antibacterials, antibiotics, antifungals, antihelminthics, antimalarials and antiviral agents); analgesics and analgesic combinations; apoptosis inducers or inhibitors; local and systemic anesthetics; cardiac and/or cardiovascular preparations (including angina and hypertension medications, anticoagulants, anti-arrhythmic agents, cardiotonics, cardiac depressants, calcium channel blockers and beta blockers, vasodilators, and vasoconstrictors); chemotherapies, including various antineoplastics; immunoreactive compounds, such as immunizing agents, immunomodulators, immunosuppressives; appetite suppressants, allergy medications, arthritis medications, antioxidants, herbal preparations and active component isolates; neurologically-active agents including Alzheimers and Parkinsons disease medications, migraine medications, adrenergic receptor agonists and antagonists, cholinergic receptor agonists and antagonists, anti-anxiety preparations, anxiolytics, anticonvulsants, antidepressants, anti-epileptics, antipsycotics, antispasmodics, psychostimulants, hypnotics, sedatives and tranquilizers, and the like.

In some applications, selection of the compounds used for treatment of the biological samples is made based on literature and knowledge of experts in the field of interest. In order to take full advantage of the comparative analysis approach to discerning mechanism of response for a drug or composition and identifying new compositions, it is useful to analyze a selection of compositions including, but not limited to, a range of therapeutics (either approved or currently in clinical trials), therapeutic candidates, research chemicals, libraries of synthetic compositions, natural or biological compounds, herbal compositions, and other chemicals that potentially interact with one or more target molecules or that appear to drive cells to a comparable phenotype(s).

A number of tools and techniques can be used to treat cells in the context of the present invention. These techniques include, but are not limited to, transient treatments with chemicals that broadly stimulate activity and/or generally perturb the environment within the cell. By "stimulation" is meant a perturbation in the equilibrium state of the biochemical and/or genetic pathways of the cell, and is not meant to be limited to an increase in concentration or biological activity. Examples of stimulatory agents, chemicals and treatments include, but are not limited to, oxidative stress, pH stress, pH altering agents, DNA damaging agents, membrane disrupters, metabolic blocking agents, and energy blockers. Additionally, cellular perturbation may be achieved by treatment with chemical inhibitors, cell surface receptor ligands, antibodies, oligonucleotides, ribozymes and/or vectors employing inducible, gene-specific knock in and knock down technologies. The identity and use of stimulatory agents, chemicals and treatments are known to one of skill in the art.

Examples of DNA damaging agents include, but are not limited to, intercalation agents such as ethidium bromide; alkylating agents such as methyl methanesulfonate; hydrogen peroxide; UV irradiation, and gamma irradiation. Examples of oxidative stress agents include, but are not limited to, hydrogen peroxide, superoxide radicals, hydroxyl free radicals, perhydroxyl radicals, peroxyl radicals, alkoxyl radicals, and the like. Examples of membrane disrupters include, but are not limited to, application of electric voltage potentials, Triton X-100, sodium dodecyl sulfate (SDS), and various detergents. Examples of metabolic blocking and/or energy blocking agents include, but are not limited to, azidothymidine (AZT), ion (e.g. $Ca^{++}$, $K^+$, $Na^+$) channel blockers, α and β adrenoreceptor blockers, histamine blockers, and the like. Examples of chemical inhibitors include, but are not limited to, receptor antagonists and inhibitory metabolites/catabolites (for example, mavelonate, which is a product of and in turn inhibits HMG-CoA reductase activity).

Examples of cell surface receptor ligands include, but are not limited to, various hormones (estrogen, testosterone, other steroids), growth factors, and G-protein-coupled receptor ligands. Examples of antibodies include, but are not limited to, antibodies directed against TNFα, TRAIL, or the HER2 growth factor receptor.

Examples of oligonucleotides that can be used to treat samples in present invention include, but are not limited to, ribozymes, anti-sense oligonucleotides, iRNA, siRNA, etc. For example, ribozymes are RNA molecules that have an enzymatic or catalytic activity against sequence-specific RNA molecules (see, for example, *Intracellular Ribozyme Applications Principles and Protocols*, J. Rossi and L. Couture, eds. (1999, Horizon Scientific Press, Norfolk, UK)). Ribozymes can be generated against any number of RNA sequences, as shown in the literature for a number of target mRNAs including calretinin, TNFα, HIV-1 integrase, and the human interleukins.

In one embodiment of the present invention, treating biological samples involves administering varying concentrations of the plurality of compounds to a plurality of biological samples (e.g., subpopulations of a cell line grown in culture), thereby generating a dose-response. The responses can be measured at either a single timepoint or over a plurality of timepoints. Optionally, at least one measurement is collected prior to treatment with the member composition. Commonly, this "zero time point" sample serves as a reference or control. Alternatively, or additionally, a separate but comparable biological sample (e.g., a subpopulation of the same cell line used for the treated samples) is left untreated or unexposed to any exogenous compound for purposes of a reference or control.

Biological Samples

Expressed RNA samples for use in the screening methods of the present invention are obtained from a number of biological sources. Biological samples can either prokaryotic or eukaryotic in origin. For example, expressed RNA samples can be obtained from such biological sources as animals, plants, yeast, fungi, bacteria and viruses which have been treated with one or more members of a compound library. Biological samples in the context of the present invention include vertebrates, such as mammals, e.g., mice, rats, hamsters, guinea pigs, rabbits, cats, dogs, primates, humans, and non-mammalian vertebrates, such as amphibians, e.g., frogs, toads, and fish, such as zebra fish, and other species of scientific interest, as well as non-vertebrate species such as nematodes and insects, e.g., *Drosophila*.

Most frequently the biological source or sample is a cell line grown in culture, i.e., an immortalized strain of a cell obtained from a multicellular organism. Cell lines useful in the methods of the invention includes cell lines derived from, for example, one or more different types of tissues or tumors, primary cell lines, cells which have been subjected to transient and/or stable genetic modification, and the like. Optionally, the cells are mammalian cells, for example murine, rodent, guinea pig, rabbit, canine, feline, primate or human cells. Alternatively, the cells can be of non-mammalian origin, derived, for example, from frogs, amphibians, or various fishes such as the zebra fish.

Cell lines which can be used in the methods of the present invention include, but are not limited to, those available from cell repositories such as the American Type Culture Collection (www.atcc.org), the World Data Center on Microorganisms (http://wdcm.nig.ac.jp), European Collection of Animal Cell Culture (www.ecacc.org) and the Japanese Cancer Research Resources Bank (http://cellbank.nihs.go.jp). These cell lines include, but are not limited to, the following cell lines: 293, 293Tet-Off, CHO-AA8 Tet-Off, MCF7, MCF7 Tet-Off, LNCap, T-5, BSC-1, BHK-21, Phinx-A, 3T3, HeLa, PC3, DU145, ZR 75-1, HS 578-T, DBT, Bos, CV1, L-2, RK13, HTTA, HepG2, BHK-Jurkat, Daudi, RAMOS, KG-1, K562, U937, HSB-2, HL-60, MDAHB231, C2C12, HTB-26, HTB-129, HPIC5, A-431, CRL-1573, 3T3L1, Cama-1, J774A.1, HeLa 229, PT-67, Cos7, OST7, HeLa-S, THP-1, and NXA. Additional cell lines can be obtained, for example, from cell line providers such as Clonetics Corporation (Walkersville, Md.; www.clonetics.com). Optionally, the expressed RNA samples are derived from cultured cells optimized for the analysis of a particular disease area of interest, e.g., cancer, inflammation, cardiovascular disease, infectious diseases, proliferative diseases, an immune system disorder (e.g., multiple sclerosis, diabetes, allergy), or a central nervous system disorder (e.g., alzheimer's disease, parkinson disease).

A variety of cell culture media for maintaining cells of interest in culture are described in *The Handbook of Microbiological Media*, Atlas and Parks (eds) (1993, CRC Press, Boca Raton, Fla.). References describing the techniques involved in bacterial and animal cell culture include Sambrook et al., *Molecular Cloning—A Laboratory Manual* (2nd Ed.), Vol. 1-3 (1989, Cold Spring Harbor Laboratory, Cold Spring Harbor, N.Y.); *Current Protocols in Molecular Biology*, F. M. Ausubel et al., eds., Current Protocols, (John Wiley & Sons, Inc., supplemented through 2002); Freshney, *Culture of Animal Cells, a Manual of Basic Technique*, third edition (1994, Wiley-Liss, New York) and the references cited therein; Humason, *Animal Tissue Techniques*, fourth edition (1979, W.H. Freeman and Company, New York); and Ricciardelli, et al. (1989) *In Vitro Cell Dev. Biol.* 25:1016-1024. Information regarding plant cell culture can be found in *Plant Cell and Tissue Culture in Liquid Systems*, by Payne et al. (1992, John Wiley & Sons, Inc. New York, N.Y.); *Plant Cell, Tissue and Organ Culture: Fundamental Methods* by Gamborg and Phillips, eds. (1995, Springer Lab Manual, Springer-Verlag, Berlin), and is also available in commercial literature such as the *Life Science Research Cell Culture Catalogue* (1998) from Sigma-Aldrich, Inc (St Louis, Mo.) (Sigma-LSRCCC) and the *Plant Culture Catalogue* and supplement (1997) also from Sigma-Aldrich, Inc (St Louis, Mo.) (Sigma-PCCS).

For example, either primary or immortalized (or other) cell lines are grown in a master flask, then trypsinized (if they are adherent) and transferred to a 96-well plate, seeding each well at a density of $10^4$ to $10^6$ cells/well. If the gene expression profile in response to a chemical treatment is sought, the chemical agent of choice is prepared in a range of concentrations (further details regarding treatment with, e.g., compound or chemical libraries, is provided hereinbelow). After a time of recovery and growth as appropriate to the cell line, cells are exposed to the chemical for a period of time that will not adversely impact the viability of the cells. Preferably, assays include a range of chemical concentrations and exposure times, and include replicate samples. After treatment, typically, the medium is removed and expressed RNA samples are prepared form the cells. Alternatively, other multiwell plate formats can be employed, such as 6, 12, 48, 384, 1536 wells, etc. Culture formats that do not use conventional flasks (e.g., roller bottles, plates, etc.), as well as microtiter formats, can also be used.

The choice of cell lines employed in the methods of the present invention will vary based upon a number of factors, such as the desired activity, the disease area of interest, and the number of relevant cell lines available. Additional considerations, e.g., for screening compound libraries for potential drug targets, include, but are not limited to, the representation of diverse cell types (for example, the use of diverse cancer cell types for screening of cancer inhibitory compounds), previous usage in the study of similar compounds, and sensitivity or resistance to drug treatment. Optionally, the methods are performed in a high throughput, multiwell format.

In some circumstances, cell lines with one or more modifications in a biochemical or genetic pathway are employed. The difference between a modified (daughter) cell line and a parental (e.g. wild type) cell line can arise, for example, from changes in the "functional activity" of at least one biological molecule, for example, a protein or a nucleic acid. A difference in the functional activity of a biological molecule refers to an alteration in an activity and/or a concentration of that molecule, and can include, but is not limited to, changes in transcriptional activity, translational activity, catalytic activity, binding or hybridization activity, stability, abundance, transportation, compartmentalization, secretion, or a combination thereof. The functional activity of a biological molecule can also be affected by changes in one or more chemical modifications of that molecule, including but not limited to adenylation, glycosylation, phosphorylation, acetylation, methylation, ubiquitination, and the like.

The alteration in activity or concentration of the at least one biological molecule can also result from treatment of the parental cell line. Furthermore, the alteration can be a temporary response to treatment, e.g., stimulation inhibition, or it can be a permanent change (e.g., a mutation or an irreversible structural modification). Temporary alterations can be produced by treatment with a variety of chemical stimulatory and inhibitory molecules, as well as by cell surface receptor ligands, antibodies, oligonucleotides, ribozymes and/or vectors employing inducible, gene-specific knock in and knock down technologies. Alternatively, cells can be treated with DNA damaging agents such as, intercalating agents such as ethidium bromide; alkylating agents such as ethylnitrosourea and methyl methanesulfonate; hydrogen peroxide; UV irradiation, and gamma irradiation. Examples of oxidative stress agents include, but are not limited to, hydrogen peroxide, superoxide radicals, hydroxyl free radicals, perhydroxyl radicals, peroxyl radicals, alkoxyl radicals, and the like. Examples of metabolic blocking and/or energy blocking agents include, but are not limited to, azidothymidine (AZT), ion (e.g. $Ca^{++}$, $K^+$, $Na^+$) channel blockers, $\alpha$ and $\beta$ adrenoreceptor blockers, histamine blockers, and the like. Examples of chemical inhibitors include, but are not limited to, receptor antagonists and inhibitory metabolites/catabolites (for example, mavelonate, which is a product of and in turn inhibits HMG-CoA reductase activity).

In some cases, it is optionally desirable to subject the cell line (or other biological sample) to one or more environmental stimuli that affect gene expression prior to treating with a compound library. For example, a cell line can optionally be exposed to an environmental condition, or change in an environmental condition that results in activation or suppression or one or more genetic or biochemical pathways. Exemplary environmental stimuli include changes in temperature, changes in pH, changes in oxygen tension, changes in carbon dioxide tension, changes in gas composition, changes in atmospheric pressure or exposure to light, e.g., visible, ultraviolet, or infrared radiation. Alternatively, environmental stimuli include agents which either directly or indirectly influence gene expression, including, e.g., solvents.

In some cases, expression of one or more genes in the biological sample (e.g., cells, tissue or organism) is artificially altered prior to treating the sample with members of a compound library. Typically, such an alteration is induced to enhance the utility of the biological sample as a model system in which to test for physiological effects induced by members of a compound library.

For example, procedures which alter the genome of the biological sample in a permanent manner, such as insertional mutagenesis, deletion of genomic DNA, targeted gene disruption, introduction of a genomic or episomal vector, and the like can be used to alter expression of one or more genes in a biological sample in a manner which increases its utility as a model for compound library screening. Similarly, procedures which alter expression by interacting with DNA or RNA, such as transcription blocking, antisense DNA or RNA, iRNA, ribozymes, DNA binding oligonucleotides and zinc finger proteins can be used to impact the expression of one or more genes in the biological sample prior to treating the sample with a member of a compound library.

Permanent genetic alteration can be produced by a variety of well known mutagenesis procedures, e.g., to generate mutant or variant cell lines suitable for library screening. A variety of mutagenesis protocols, such as viral-based mutational techniques, homologous recombination techniques, gene trap strategies, inaccurate replication strategies, and chemical mutagenesis, are available and described in the art. These procedures can be used separately and/or in combination to produce modified cell lines for use in the methods of the present invention. See, for example, Amsterdam et al. "A large-scale insertional mutagenesis screen in zebrafish" Genes Dev 1999 October 13:2713-2724; Carter (1986) "Site-directed mutagenesis" Biochem. J. 237:1-7; Crameri and Stemmer (1995) "Combinatorial multiple cassette mutagenesis creates all the permutations of mutant and wildtype cassettes" BioTechniques 18:194-195; Inamdar "Functional genomics the old-fashioned way: chemical mutagenesis in mice" Bioessays 2001 February 23:116-120; Ling et al. (1997) "Approaches to DNA mutagenesis: an overview" Anal Biochem. 254(2): 157-178; Napolitano et al. "All three SOS-inducible DNA polymerases (Pol II, Pol IV and Pol V) are involved in induced mutagenesis" EMBO J 2000 November 19:6259-6265; and Rathkolb et al. "Large-scale N-ethyl-N-nitrosourea mutagenesis of mice—from phenotypes to genes" Exp Physiol 2000 November 85:635-44. Furthermore, kits for mutagenesis and related techniques are also available from a number of commercial sources (see, for example, Stratagene (http://www.stratagene.com/vectors/index2.htm), Clontech (http://www.clontech.com/retroviral/index.shtml), and the Gateway cloning system from Invitrogen (http://www.invitrogen.com). General texts which describe molecular biological techniques useful in the generation of modified cell lines, including mutagenesis, include Berger and Kimmel; Sambrook et al., and Ausubel et al., all supra. Further details regarding the generation of modified cell lines can be found in, e.g., WO 02/08466 by Monforte, and WO 01/71023.

Alternatively, procedures for making targeted gene mutations can be employed to modify cell lines prior to treating with members of a compound library. For example, a gene can be prevented from expressing any protein (knockout) via a number of processes, including deletion of the gene or transcription promoting elements for the gene at the DNA level within the cell. Knockout modifications generally involve modification of the gene or genes within the genome (see, for example, Gonzalez (2001) "The use of gene knockout mice to unravel the mechanisms of toxicity and chemical carcinogenesis" Toxicol Lett 120:199-208); Knockouts can be either heterozygous (e.g. inactivating only one copy of the gene) or homozygous (inactivating both copies of the gene). One exemplary database of mouse knockouts can be found at http://research.bmn.com (the BioMedNet mouse knockout and mutation database).

Following, or in conjunction with mutagenesis procedures, cell lines with desired modifications are typically selected using one or more experimental techniques to identify and isolate cells which have been altered in the desired manner. For example, the selection process can include, but is not limited to: identifying cells that survive and/or continue to grow under different environments, stresses and/or stimulation; cells that have increased or decreased expression of a particular protein that can be used to sort or separate cells with the altered protein levels, (e.g. using flow cytometry to sort cells that are over expressing a particular cell surface receptor); and cells that have an altered physical phenotype that can be identified and selected, e.g. cells arrested in a particular cycle phase, cells that have altered ability to invade a barrier or translocate, cells that have a different shape, or have or have not differentiated into a different cell type). Numerous additional selection methods are known to one of skill in the art and can be employed to provide cell lines for use in the methods of the present invention.

Isolation of Expressed RNA Samples

Expressed RNA samples are isolated from biological samples using any of a number of well-known procedures. For example, biological samples are lysed in a guanidinium-based lysis buffer, optionally containing additional components to stabilize the RNA. In some embodiments of the present invention, the lysis buffer also contains purified RNAs as controls to monitor recovery and stability of RNA from cell cultures. Examples of such purified RNA templates include the Kanamycin Positive Control RNA from Promega (Madison, Wis.), and 7.5 kb Poly(A)-Tailed RNA from Life Technologies (Rockville, Md.). Lysates may be used immediately or stored frozen at, e.g., −80° C.

Optionally, total RNA is purified from cell lysates (or other types of samples) using silica-based isolation in an automation-compatible, 96-well format, such as the Rneasy® purification platform (Qiagen, Inc.; Valencia, Calif.). Alternatively, RNA is isolated using solid-phase oligo-dT capture using oligo-dT bound to microbeads or cellulose columns. This method has the added advantage of isolating mRNA from genomic DNA and total RNA, and allowing transfer of the mRNA-capture medium directly into the reverse transcriptase reaction. Other RNA isolation methods are contemplated, such as extraction with silica-coated beads or guanidinium. Further methods for RNA isolation and preparation can be devised by one skilled in the art.

Alternatively, the methods of the present invention are performed using crude cell lysates, eliminating the need to isolate RNA. RNAse inhibitors are optionally added to the crude samples. When using crude cellular lysates, it should be noted that genomic DNA can contribute one or more copies of a target sequence, e.g., a gene, depending on the sample. In situations in which the target sequence is derived from one or more highly expressed genes, the signal arising from genomic DNA may not be significant. But for genes expressed at very low levels, the background can be eliminated by treating the samples with DNAse, or by using primers that target splice junctions for subsequent priming of cDNA or amplification products. For example, one of the two target-specific primers could be designed to span a splice junction, thus excluding DNA as a template. As another example, the two target-specific primers are designed to flank a splice junction, generating larger PCR products for DNA or unspliced mRNA templates as compared to processed mRNA templates. One skilled in the art could design a variety of specialized priming applications that would facilitate use of crude extracts as samples for the purposes of this invention.

Nucleic Acids Corresponding to Expressed RNA Samples

In the methods of the present invention, nucleic acids corresponding to expressed RNA samples are logically or spatially arrayed, as described in further detail below. Although expressed RNA samples can be arrayed directly, e.g., on the surface of a glass microarray slide, it is generally desirable to employ DNA products corresponding to the expressed RNA sample to improve stability and ease of handling. In some instances, cDNA products reverse transcribed from the expressed RNA samples according to well established procedures, e.g., as described in Sambrook, Ausubel, etc. are arrayed. More typically, DNA products corresponding to expressed RNA samples are amplified prior to arraying to improve the sensitivity and dynamic range of the assay.

Expressed RNA samples can be reverse transcribed using non-specific primers, such as an anchored oligo-dT primer, or random sequence primers. An advantage of this approach is that the mRNA sample maintains an "unfractionated" quality because the sites of priming are non-specific, i.e., the products of this RT reaction will serve as template for any desired target in the subsequent PCR amplification. One benefit of this approach is that samples to be archived are stored in the form of DNA, which is more resistant to degradation than RNA. In certain methods (e.g., described by Chenchik in U.S. Pat. No. 5,962,271, and commercial available kits supplied by Clontech, Palo Alto, Calif.), reverse transcription of a full length mRNA is initiated using an oligo-dT primer. A cap switching oligonucleotide primer is annealed to the 5' cap of the mRNA which serves as a template for the nascent strand as it approaches the end of mRNA template. The cap switching oligonucleotide primer includes in addition to the sequence that permits it to bind to the cap, a polynucleotide sequence that serves as a primer annealing site in subsequent amplification reactions.

Alternatively, RNA is converted to cDNA using a target-specific primer complementary to the RNA for each gene target for which expression data is desired. Methods for reverse transcription also include, the use of thermostable DNA polymerases, as described in the art. As an exemplary embodiment, avian myeloblastosis virus reverse transcriptase (AMV-RT), or Maloney murine leukemia virus reverse transcriptase (MoMLV-RT) is used, although other enzymes are contemplated. An advantage of using target-specific primers in the RT reaction is that only the desired sequences are arrayed, or optionally, used, in subsequent amplification reactions.

Amplification of DNA products corresponding to expressed RNA samples can be accomplished using the polymerase chain reaction (PCR), which is described in detail in U.S. Pat. Nos. 4,683,195 (Mullis et al.), 4,683,202 (Mullis), and 4,800,159 (Mullis et al.), and in *PCR Protocols A Guide to Methods and Applications* (Innis et al., eds.) Academic Press Inc. San Diego, Calif. (1990), see also, Sambrook, Ausubel. PCR utilizes pairs of primers, having-sequences complimentary to opposite strands of target nucleic acids, and positioned such that the primers are converging. The primers are incubated with template DNA under conditions that permit selective hybridization. Primers can be provided in double-stranded or single-stranded form, although the single-stranded form is preferred. If the target gene(s) sequence is present in a sample, the primers will hybridize to form a nucleic-acid:primer complex. An excess of deoxynucleoside triphosphates is added, along with a thermostable DNA polymerase, e.g. Taq polymerase. If the target gene(s):primer complex has been formed, the polymerase will extend the primer along the target gene(s) sequence by adding nucleotides. After polymerization, the newly-synthesized strand of DNA is dissociated from its complimentary template strand by raising the temperature of the reaction mixture. When the temperature is subsequently lowered, new primers will bind to each of these two strands of DNA, and the process is repeated. Multiple cycles of raising and lowering the temperature are conducted, with a round of replication in each cycle, until a sufficient amount of amplification product is produced.

In one favorable variation of the Polymerase Chain Reaction, nucleic acids are amplified in a reaction that couples reverse transcription and PCR, "rtCR." rtPCR techniques use either gene specific primers to selectively amplify particular gene sequences, or the use of random or semi random primers for the amplification of the global population of mRNAs or some subset based on the presence of particular sequences or sequence motifs (see, e.g., U.S. Pat. No. 5,962,271). In all forms of operation, the technique provides for the ability to multiplex to very high levels.

Alternative methods for amplifying nucleic acids corresponding to expressed RNA samples include, e.g., transcription-based amplification systems (TAS), such as that first described by Kwoh et al. (Proc. Natl. Acad. Sci. (1989) 86(4): 1173-7), or isothermal transcription-based systems such as 3SR (Self-Sustained Sequence Replication; Guatelli et al. (1990) Proc. Natl. Acad. Sci. 87:1874-1878) or NASBA (nucleic acid sequence based amplification; Kievits et al. (1991) J Virol Methods. 35(3):273-86). In these methods, one or more mRNA target of interest is copied into cDNA by a reverse transcriptase. The primer(s) for cDNA synthesis includes the promoter sequence of a designated DNA-dependent RNA polymerase 5' to the primer's region of homology with the template. In some procedures a second complementary cDNA strand is synthesized using, e.g., a hairpin loop structure formed by the initially synthesized cDNA strand (see, e.g., Van Gelder et al. U.S. Pat. No. 5,545,522). Alternatively, a second strand is synthesized from a primer complementary to a primer sequence added by template switching to an oligonucleotide that anneals to the 5' cap structure of a full-length mRNA (SMART™ Amplification described in Chenchik et al. U.S. Pat. No. 5,962,271). The resulting cDNA products can then serve as templates for multiple rounds of transcription by the appropriate RNA polymerase. Transcription of the cDNA template rapidly amplifies the signal from the original target mRNA. The isothermal reactions bypass the need for denaturing cDNA strands from their RNA templates by including RNAse H to degrade RNA hybridized to DNA. Other methods using isothermal amplification, including, e.g., methods described in U.S. Pat. No. 6,251,639, are also favorably employed in the context of the present invention.

Alternatively, amplification is accomplished by used of the ligase chain reaction (LCR), disclosed in European Patent Application No. 320,308 (Backman and Wang), or by the ligase detection reaction (LDR), disclosed in U.S. Pat. No. 4,883,750 (Whiteley et al.). In LCR, two probe pairs are prepared, which are complimentary each other, and to adjacent sequences on both strands of the target. Each pair will bind to opposite strands of the target such that they are adjacent. Each of the two probe pairs can then be linked to form a single unit, using a thermostable ligase. By temperature cycling, as in PCR, bound ligated units dissociate from the target, then both molecules can serve as "target sequences" for ligation of excess probe pairs, providing for an exponential amplification. The LDR is very similar to LCR. In this variation, oligonucleotides complimentary to only one strand of the target are used, resulting in a linear amplification of ligation products, since only the original target DNA can serve as a hybridization template. It is used following a PCR amplification of the target in order to increase signal.

Additional suitable methods include, but are not limited to, strand displacement amplification (Walker et al. (1992) Nucleic Acids Res. 20:1691-1696), repair chain reaction (REF), cyclic probe reaction (REF), solid-phase amplification, including bridge amplification (Mehta and Singh (1999) BioTechniques 26(6): 1082-1086), rolling circle amplification (Kool, U.S. Pat. No. 5,714,320), rapid amplification of cDNA ends (Frohman (1988) Proc. Natl. Acad. Sci. 85: 8998-9002), the "invader assay" (Griffin et al. (1999) Proc. Natl. Acad. Sci. 96: 6301-6306), and methods for simultaneous amplification and detection as described in, e.g., U.S. Pat. Nos. 5,914,230 and 6,365,346.

Amplification of expressed RNA samples can be performed using random or semi-random primers to globally amplify a diverse population of expression products, or can be performed using target specific primers to amplify one or more selected expression products. Selective amplification of expression products using target specific primers can be performed in reactions that amplify a single product or that amplify a plurality of products, i.e., multiplex amplification reactions. When one or a small number of expression products is amplified in a single reaction, the products of multiple reactions can be combined or pooled for arraying, if desired. Similarly, a single expressed RNA sample (i.e., from a single biological sample) can be amplified in multiple target specific reactions which are then arrayed in more than one locations of an array. Both of these variations increase the number of probes which can be analyzed in a single physical array.

Multiplex Amplification Strategies

An embodiment of the methods of the present invention involves the use of various PCR multiplexing strategies that are made possible by the combined use of target-specific (e.g., gene specific) and universal primers. These procedures are variations on the RT-PCR assays involving the reverse transcription of a single or double stranded DNA template corresponding to one or more expressed RNA species, followed by amplification in a PCR. Additional details regarding multiplex PCR strategies are found in, e.g., WO 01/55454 by Loehrlein et al; and, U.S. Pat. No. 5,962,271 to Chenchik et al.

Multiplex amplification of a plurality target sequences typically involves combining the plurality of target sequences with a plurality of target-specific primers (i.e., primers complementary to at least one strand of a reverse transcribed cDNA target sequence) and one or more universal primers, to produce a plurality of amplification products. A multiplex set of target sequences optionally comprises between about two targets and about 100 targets. In one embodiment of the present invention, the multiplex reaction includes at least 5 target sequences, but preferably at least ten targets or at least fifteen targets. Multiplexes of much larger numbers (e.g., about 20, about 50, about 75 and greater) are also contemplated.

In one embodiment of the methods of the present invention, at least one of the amplification targets in the multiplex set is a transcript that is endogenous to the sample and has been independently shown to exhibit a fairly constant expression level (for example, a "housekeeping" gene, β-actin). The signal from this endogenous reference sequence provides a control for converting signals of other gene targets into relative expression levels. Optionally, a plurality of control mRNA targets/reference sequences that have relatively constant expression levels may be included in the multiplexed amplification to serve as controls for each other. Alternatively, a defined quantity of an exogenous purified RNA species is added to the multiplex reaction or to the cells, for example, with the lysis reagents. Almost any purified, intact RNA species can be used, e.g. the Kanamycin Positive Control RNA or the 7.5 kb Poly(A)-Tailed RNA mentioned previously. This exogenously-added amplification target provides a way to monitor the recovery and stability of RNA from cell cultures. It can also serve as an exogenous reference signal for converting the signals obtained from the sample mRNAs into relative expression levels. In still another embodiment, a defined quantity of a purified DNA species is added to the PCR to provide an exogenous reference target for converting the signals obtained from sample mRNA targets into relative expression levels.

In one embodiment of the present invention, once the targets that comprise a multiplex set are determined, primer pairs complementary to each target sequence are designed, including both target-specific and universal primers. This can be accomplished using any of several software products that design primer sequences, such as OLIGO (Molecular Biology Insights, Inc., CO), Gene Runner (Hastings Software Inc., NY), or Primer3 (The Whitehead Institute, MA). Target specific primers include at least two portions. The first portion includes a region complementary to a selected "universal sequence." The universal sequence is utilized to allow amplification of multiple targets (having divergent sequences) while using the same primer (e.g., the UP). The universal sequence is contained only in the primers, and preferably is not present in any nucleic acid (or complement thereof) provided by the sample being tested. A second portion of the TSPs, within the 3' region of the sequence, is complementary to and will hybridize with one of a plurality of designated target sequences. Although a single universal primer is described in the example provided above, multiple universal primers having different or unique sequences or labels can be employed in the methods of the present invention. If a single UP is used, the universal sequence will be the same within all TSPs. If a UP pair is to be used, the universal sequence will be different in the forward and reverse primers of the TSPs. The UP may also contain a detectable label on at least one of the primers, such as a fluorescent chromaphore. Both the target-specific and universal sequences are of sufficient length and sequence complexity to form stable and specific duplexes, allowing amplification and detection of the target gene. In early rounds of the amplification, replication is primed primarily by the TSPs. The first round will add the universal sequence to the 5' regions of the amplification products. The second cycle will generate sequence complementary to the universal sequence within the 3' region of the complementary strand, creating a template that can be amplified by the universal primers alone. Optionally, the reaction is designed to contain limiting amounts of each of the TSPs and a molar excess of the UP, such that the UP will generally prime replication once its complementary sequence has been established in the template. The molar excess of UP over a TSP can range from about 5:1 to about 100:1; optionally, the reaction utilizes approximately 10:1 molar excess of UP over the amount of each TSP. Because all of the TSPs contain the same universal sequence, the same universal primer will amplify all targets in the multiplex, eliminating the quantitative variation that results from amplification from different primers.

The templates are initially single-stranded mRNA molecules, but eventually are predominantly DNA amplification products that serve as template in subsequent cycles. Messenger RNA is converted to cDNA by the action of reverse transcriptase polymerization from the target-specific reverse primers, or from a random or degenerate primer that results in global reverse transcription of the constituents of an expressed RNA sample. If a single stranded cDNA template has been synthesized, the target-specific forward primers and the universal forward and reverse primers are added along with a thermostable polymerase to generate the second strand of cDNA, followed by PCR amplification. The UP can anneal to target DNA only after its complementary universal sequence is added to the opposite strand through replication across the 5' region of the TSP.

The length of complementary sequence between each primer and its binding partner (i.e. the target sequence or the universal sequence) should be sufficient to allow hybridization of the primer only to its target within a complex sample at the annealing temperature used for the PCR. A complementary sequence of, for example, about 15, 16, 17, 18, 19, 20, 21, 22, 23, 24, or 25 or more nucleotides is preferred for both the target-specific and universal regions of the primers. A particularly preferred length of each complementary region is about 20 bases, which will promote formation of stable and specific hybrids between the primer and target.

Optionally, primers are designed such that the annealing temperature of the universal sequence is higher/greater than that of the target-specific sequences. Method employing these primers further include increasing the annealing temperature of the reaction after the first few rounds of amplification. This increase in reaction temperature suppresses further amplification of sample nucleic acids by the TSPs, and drives amplification by the UP. Depending on the application envisioned, one skilled in the art can employ varying conditions of hybridization to achieve varying degrees of selectivity of primer towards the target sequence. For example, varying the stringency of hybridization or the position of primer hybridization can reveal divergence within gene families.

Optionally, each candidate primer is shown or proven to be compatible with the other primers used in a multiplex reaction. In a preferred embodiment, each target-specific primer pair produces a single amplification product of a predicted size from a sample minimally containing all of the targets of the multiplex, and more preferably from a crude RNA mixture. Preferably, amplification of each individual target by its corresponding primers is not inhibited by inclusion of any other primers in the multiplex. None of the primers, either individually or in combination, should produce spurious products. These issues are easily addressed by one of skill in the art without the need for excessive experimentation.

Oligonucleotide primers are typically prepared by the phosphoramidite approach. In this automated, solid-phase procedure, each nucleotide is individually added to the 5'-end of the growing oligonucleotide chain, which is in turn attached at the 3'-end to a solid support. The added nucleotides are in the form of trivalent 3'-phosphoramidites that are protected from polymerization by a dimethoxytrityl ("DMT") group at the 5'-position. After base induced phosphoramidite coupling, mild oxidation to give a pentavalent phosphotriester intermediate and DMT removal provides a new site for oligonucleotide elongation. These syntheses may be performed on, for example, a Perkin Elmer/Applied Biosystems Division DNA synthesizer. The oligonucleotide primers are then cleaved off the solid support, and the phosphodiester and exocyclic amino groups are deprotected with ammonium hydroxide.

Elimination of Variations in Primer Annealing Efficiency

Variations in primer length and sequence can have a large impact on the efficiency with which primers anneal to their target and prime replication. In a typical multiplexed reaction in which each product is amplified by a unique primer pair, the relative quantities of amplified products may be significantly altered from the relative quantities of targets due to difference in annealing efficiencies. Embodiments of the methods of the present invention that couple the use of target-specific primers and universal primers eliminates this bias, producing amplification products that accurately reflect relative mRNA levels.

Attenuation of Strong Signals

The set of targets included in a multiplex reaction generally all yield signal strengths within the dynamic range of the detection platform used in order for quantitation of gene expression to be accurate. In some embodiments, it may be desirable or necessary to include a very highly expressed gene in a multiplex assay. However, the highly-expressed gene can interfere with quantitation for other genes expressed at very low levels if its signal is not attenuated. The methods of the current invention provide ways for attenuating the signals of relatively abundant targets during the amplification reaction such that they can be included in a multiplexed set without impacting the accuracy of quantitation of that set.

Amplification primers are optionally used that block polymerase extension of the 3' end of the primer. One preferred embodiment is modification of the 3'-hydroxyl of the oligonucleotide primer by addition of a phosphate group. Another preferred embodiment is attachment of the terminal nucleotide via a 3'-3' linkage. One skilled in the art can conceive of other chemical structures or modifications that can be used for this purpose. The modified and the corresponding unmodified primer for the highly abundant target are mixed in a ratio empirically determined to reduce that target's signal, such that it falls within the dynamic range of other targets of the multiplex. Preferably, the reverse target-specific primer is modified, thereby attenuating signal by reduction of the amount of template created in the reverse transcriptase reaction.

Another embodiment for signal attenuation entails use of a target-specific primer that contains the target-specific sequence, but no universal primer sequence. This abbreviated primer (lacking the universal sequence) and the corresponding primer containing the universal sequence within the 5' region are mixed in a ratio empirically determined to reduce that target's signal, such that it then falls within the dynamic range of other targets of the multiplex system.

Purification of rtPCR Products

It is often desirable to "purify" the population of nucleic acids corresponding to expressed RNA samples (e.g., rtPCR products), prior to deposit on an array, due to presence of contaminants and salts. Numerous approaches to purifying nucleic acids, such as PCR products, exist with the two principle high throughput approaches being filtration in microtiter-plate format and magnetic bead capture and washing. For example, the Millipore Montage PCR96 DNA purification plates (and comparable 384-well version of this plate) are favorably employed in the context of the present invention. The protocol for use involves a simple one-step vacuum filtration and elution of the PCR products, and is compatible with automated systems, such as the Biomek Multimek system. Alternatively, magnetic bead capture and washing approaches can be adapted for an automated platform.

Array Format

Nucleic acids corresponding to expressed RNA samples, whether RNA, cDNA or amplification products are then spatially or logically arrayed. Numerous technological platforms for performing high throughput expression analysis using nucleic acid arrays are available. Common array formats include both liquid and solid phase arrays. For example, assays employing liquid phase arrays, e.g., for hybridization of nucleic acids, can be performed in multiwell, or microtiter, plates. Microtiter plates with 96, 384 or 1536 wells are widely available, and even higher numbers of wells, e.g, 3456 and 9600 can be used. In general, the choice of microtiter plates is determined by the methods and equipment, e.g., robotic handling and loading systems, used for sample preparation and analysis. Exemplary systems include, e.g., the ORCA™ system from Beckman-Coulter, Inc. (Fullerton, Calif.) and the Zymate systems from Zymark Corporation (Hopkinton, Mass.).

Alternatively, a variety of solid phase arrays can favorably be employed to determine expression patterns in the context of the present invention. Exemplary formats include membrane or filter arrays (e.g., nitrocellulose, nylon), pin arrays, and bead arrays (e.g., in a liquid "slurry"). Typically, nucleic acids corresponding to expressed RNA samples are immobilized, for example by direct or indirect cross-linking, to the solid support. Essentially any solid support capable of withstanding the reagents and conditions necessary for performing the particular expression assay can be utilized. For example, functionalized glass, silicon, silicon dioxide, modified silicon, any of a variety of polymers, such as (poly) tetrafluoroethylene, (poly)vinylidenedifluoride, polystyrene, polycarbonate, or combinations thereof can all serve as the substrate for a solid phase array. Coated forms of these materials, glass (e.g. polyamine, polyacrylamide, polythymidine or other functionalization leading to improved non-covalent or covalent binding. The substrate can be a single contiguous surface, e.g. a plate or multiple discrete surfaces, e.g. etched plates, filters, or optical fiber ends. Alternatively, the array can be composed of a series of beads that can be discretely identified via a number of either color coding schemes (e.g. Luminex) and flow cytometry or means to physically trap the beads on a surface (e.g. Illumina or Lynx). Techniques for the creation and use of these arrays are known to those skilled in the art.

In a preferred embodiment, the array is a "chip" or "slide" composed, e.g., of one of the above specified materials, such as a glass microarray slide. Most commonly, nucleic acid samples corresponding to expressed RNA samples are deposited, e.g., "spotted" onto the chip or slide to produce a spatial array in which each distinct nucleic acid population corresponding to a different expressed RNA sample (e.g., derived from a different biological sample) is assigned a unique location on the microarray surface. Application of nucleic samples to the substrate can be performed using automated devices, or manually, for example, using a multipin, e.g., 32 pin, tool, with an alignment device (e.g., Xenopore, that can deposit up to 768 6 nl spots onto a glass slide). Detailed discussion of methods for linking nucleic acids to a substrate, are found in, e.g., U.S. Pat. No. 5,837,832 "Arrays of Nucleic Acid Probes on Biological Chips" to Chee et al., issued Nov. 17, 1998; U.S. Pat. No. 6,087,112 "Arrays with Modified Oligonucleotide and Polynucleotide Compositions" to Dale, issued Jul. 11, 2000; U.S. Pat. No. 5,215,882 "Method of Immobilizing Nucleic Acid on a Solid Substrate for Use in Nucleic Acid Hybridization Assays" to Bahl et al., issued Jun. 1, 1993; U.S. Pat. No. 5,707,807 "Molecular Indexing for Expressed Gene Analysis" to Kato, issued Jan. 13, 1998; U.S. Pat. No. 5,807,522 "Methods for Fabricating Microarrays of Biological Samples" to Brown et al., issued Sep. 15, 1998; U.S. Pat. No. 5,958,342 "Jet Droplet Device" to Gamble et al., issued Sep. 28, 1999; U.S. Pat. No. 5,994,076 "Methods of Assaying Differential Expression" to Chenchik et al., issued Nov. 30, 1999; U.S. Pat. No. 6,004,755 "Quantitative Microarray Hybridization Assays" to Wang, issued Dec. 21, 1999; U.S. Pat. No. 6,048,695 "Chemically Modified Nucleic Acids and Methods for Coupling Nucleic Acids to Solid Support" to Bradley et al., issued Apr. 11, 2000; U.S. Pat. No. 6,060,240 "Methods for Measuring Relative Amounts of Nucleic Acids in a Complex Mixture and Retreival of Specific Sequences Therefrom" to Kamb et al., issued May 9, 2000; U.S. Pat. No. 6,090,556 "Method for Quantitatively Determining the Expression of a Gene" to Kato, issued Jul. 18, 2000; U.S. Pat. No. 6,040,138 "Expression Monitoring by Hybridization to High Density Oligonucleotide Arrays" to Lockhart et al., issued Mar. 21, 2000; NHGRI Microarray Project Protocols: www.nhgri.nih.gov/DIR/Microarray/protocols.html; MacGregor P, Microarray protocol: www.uhnres.utoronto.ca/services/microarray/download/protocols/procol_edward.pdf; and Hedge et. al. (2000) Biotechniques 29: 548-562.

As the number of probes to be hybridized (i.e., the number of genes or sequences to be analyzed) increases, it is often desirable to produce replicate or copies of the microarray. The following illustrates one exemplary automatable array copying format, e.g., for producing replicate microarrays incorporating copies of the nucleic acids corresponding to RNA expression products from biological samples. For example, arrays can be copied in an automated format to produce duplicate arrays, master arrays, amplified arrays and the like, e.g., where repeated hybridization and washing of defined sequence probes makes recovery or detection of nucleic acids from an original array problematic (e.g. where a process to be performed destroys the original nucleic acids or attenuates the signal). Copies can be made from master arrays, reaction mixture arrays or any duplicates thereof.

For example, nucleic acids (e.g., a plurality of expressed RNA samples from biological sources) can be dispensed into one or more master multiwell plates and, typically, amplified to produce a master array of amplified nucleic acids (e.g., by PCR) to produce an array of amplification products. The array copy system then transfers aliquots from the wells of the one or more master multiwell plates to one or more copy multiwell plates. Typically, a fluid handling system will deposit copied array members in destination locations, although non-fluid based member transport (e.g., transfer in a solid or gaseous phase) can also be performed.

Arraying techniques for producing both master and duplicate arrays from populations of nucleic acids can involve any of a variety of methods. For example, when forming solid phase arrays (e.g., as a copy of a liquid phase array, or as an original array), members of the population can by lyophilized or baked on a solid surface to form a solid phase array, or chemically coupled or printed (e.g., using ink-jet printing or chip-masking and photo-activated synthesis methods) to the solid surface.

Expression Profiling

The plurality of probes (e.g., set of genes or gene products) selected for analysis can be selected, for example, by scanning the literature or by performing empirical studies. In one embodiment, the probes are selected from among genes (or gene products) that are (a) expressed at detectable levels within the biological samples, and (b) are likely to change as a result of exposure to one or more member compositions. Two types of genes (or their respective gene products) are typically monitored during generation of the genetic response profile: genes that are empirical responders (i.e. marker genes) and genes that are known or suspected to be involved in the pathways or disease area of interest (i.e., disease related genes). Optionally, one or more genes known to be affected by at least one composition in the set of compounds or chemicals are monitored (e.g., a positive control).

Typically, a moderate to large number of genes (i.e., expressed RNAs) are selected for analysis, i.e., expression (or response) profiling. Such a set of genes commonly includes at least three polynucleotide sequences, more commonly between about 10 and about 20 sequences, often about 50 sequences, sometimes about 100, and occasionally as many as about 1000, or more individual polynucleotide sequences, e.g., corresponding to different or distinct genes. Nucleic acid sequences that can be monitored in the methods of the present invention include, but are not limited to, those listed with the National Center for Biotechnology Information (www.ncbi.nlm.nih.gov) in the GenBank® databases, and sequences provided by other public or commercially-available databases (for example, the NCBI EST sequence database, the EMBL Nucleotide Sequence Database; Incyte's (Palo Alto, Calif.) LifeSeq™ database, and Celera's (Rockville, Md.) "Discovery System"™ database). For example, nucleic acids that can be monitored (e.g., as part of the genetic response profile) according to the methods of the present invention include, nucleic acids encoding proteins including, but not limited to, signaling proteins, regulatory proteins, pathway specific proteins, receptor proteins, and other proteins involved in one or more biochemical pathways.

Analysis of Gene Expression Data

Patterns of gene expression in expressed RNA samples can be evaluated by either (or both) qualitative and quantitative measures. Certain of the above described techniques for evaluating gene expression (as RNA or protein products) yield data that are predominantly qualitative in nature. That is, the methods detect differences in expression that classify expression into distinct modes without providing significant information regarding quantitative aspects of expression. For example, a technique can be described as a qualitative technique if it detects the presence or absence of expression of a candidate gene, i.e., an on/off pattern of expression. Alternatively, a qualitative technique measures the presence (and/or absence) of different alleles, or variants, of a gene product.

In contrast, some methods provide data that characterizes expression in a quantitative manner. That is, the methods relate expression on a numerical scale, e.g, a scale of 0-5, a scale of 1-10, a scale of +-+++, from grade 1 to grade 5, a grade from a to z, or the like. It will be understood that the numerical, and symbolic examples provided are arbitrary, and that any graduated scale (or any symbolic representation of a graduated scale) can be employed in the context of the present invention to describe quantitative differences in gene expression. Typically, such methods yield information corresponding to a relative increase or decrease in expression.

Any method that yields either quantitative or qualitative expression data is suitable for evaluating signals corresponding to hybridization between a defined sequence probe, e.g., corresponding to a gene, such as a disease related gene) and an arrayed nucleic acid sample. In some embodiments, it is useful to quantitate the level of expression of a gene relative to other expression products, and/or relative to a control sequence. One convenient and broadly applicable method of determining relative expression and hybridization levels between expression products on an array, as well as between physical arrays, is to compare the expression of one or more genes of interest to the expression of a control gene, such as a housekeeping gene (e.g., HSP 70, β-actin, etc.) One or more defined sequence probes specific for the genes of interest are hybridized along with a probe specific for the selected housekeeping gene. Hybridization to each of the probes is detected and quantitated. Then the hybridization signal corresponding to the genes of interest is compared to that for the housekeeping gene. Expression can then be expressed relative to that of the housekeeping gene which is expected to be approximately constant between within and between samples.

In order to ascertain whether the observed expression data, e.g., a change in expression profiles in response to one or more treatments of a biological sample, are significant, and not just a product of experimental noise or population heterogeneity, an estimate of a probability distribution can be constructed for each genetic and phenotypic endpoint in each biological sample. Construction of the estimated population distribution involves running multiple independent experiments for each treatment, e.g. all experiments are run in duplicate, triplicate, quadruplicate or the like.

Analysis of the data involves the use of a number of statistical tools to evaluate the measured expression as extrapolated from the hybridization signal, e.g., responses and changes resulting from one or more treatment of a biological sample, based on type of change, direction of change, shape of the curve in the change, timing of the change and amplitude of change.

Multivariate statistics, such as principal components analysis (PCA), factor analysis, cluster analysis, n-dimensional analysis, difference analysis, multidimensional scaling, discriminant analysis, and correspondence analysis, can be employed to simultaneously examine multiple variables for one or more patterns of relationships (for a general review, see Chatfield and Collins, *Introduction to Multivariate Analysis*, published 1980 by Chapman and Hall, New York; and Höskuldsson Agnar, *Predictions Methods in Science and Technology*, published 1996 by John Wiley and Sons, New York). Multivariate data analyses are used for a variety of applications involving these multiple factors, including quality control, process optimization, and formulation determinations. The analyses can be used to determine whether there are any trends in the data collected, whether the properties or responses measured are related to one another, and which properties are most relevant in a given context (for example, a disease state). Software for statistical analysis is commonly available, e.g., from Partek Inc. (St. Peters, Mo.; see www-.partek.com).

One common method of multivariate analysis is principal component analysis (PCA, also known as a Karhunen-Loève expansion or Eigen-XY analysis). PCA can be used to transform a large number of (possibly) correlated variables into a smaller number of uncorrelated variables, termed "principal components." Multivariate analyses such as PCA are known to one of skill in the art, and can be found, for example, in Roweis and Saul (2000) *Science* 290:2323-2326 and Tenenbaum et al. (2000) *Science* 290:2319-2322. Several methods of constructing and analyzing dataspace, e.g., including multivariate analysis are available. See, e.g., Hinchliffe (1996) *Modeling Molecular Structures* John Wiley and Sons, NY, N.Y.; Gibas and Jambeck (2001) *Bioinformatics Computer Skills* O'Reilly, Sebastopol, Calif.; Pevzner (2000) *Computational Molecular Biology and Algorithmic Approach*, The MIT Press, Cambridge Mass.; Durbin et al. (1998) *Biological Sequence Analysis Probabilistic Models of Proteins and Nucleic Acids*, Cambridge University Press, Cambridge, UK; Rashidi and Buehler (2000) *Bioinformatic Basics: Applications in Biological Science and Medicine*, CRC Press LLC, Boca Raton, Fla.; and Mount (2001) *Bioinformatics: Sequence and Genome Analysis*, Cold Spring Harbor Press, New York.

The expression data from multiple biological samples can be grouped, or clustered, using multivariate statistics. Clusters for each different stimulation (treating) and observation (detecting) experiment are compared and a secondary set of correlations/noncorrelations are made. Based on these different sets of correlations, a network map can be created wherein the relative relationships of the different genetic elements can be established as well as how they may act in concert. In addition, the data can be visualized using graphical representations. Thus, the temporal changes exhibited by the different biochemical and genetic elements within a genetically-related group of cells lines can be transformed into information reflecting the functioning of the cells within a given environment.

For example in the context of screening a compound, e.g., chemical, library, compounds that evoke a similar genetic response are likely to share one or more mechanisms of action. Through analysis of a set of compounds and/or chemical analogues, pathway specific inhibitors and comparable pharmacophores, the mechanistic differences and commonalities can be elucidated. A difference analysis provides the means to identify one or more elements responsible for the desired activity or phenotypic response. In addition, the dose response data coupled with the difference analysis enables the creation of a mechanism of action (MOA) model. Libraries of compositions can be screened for their ability to evoke a genetic response profile similar to that targeted for the desired activity. Furthermore, compositions can be tested against the MOA model to assess if they stimulate similar mechanisms of response.

Different experimental outcomes are compared by the similarity of the pattern of expression profiles generated. This similarity is revealed using, for example, clustering analysis. A number of clustering algorithms are commonly used for this type of study (see J A Hartigan (1975) *Clustering Algorithms*, Wiley, NY). The comparisons between profiles can be performed at the level of individual genes, clusters of genes known to be involved in specific pathways or mechanisms, individual cell lines, or for the entire experimental data set. For example, for each experimental pair, e.g. two different composition treatment sets, a distance metric can be defined as $D=1-\rho$, where $\rho$ is the correlation coefficient between the expression profiles. The value of D indicates the level of similarity between two experimental pairs. In this manner, a matrix can be created wherein chemicals producing similar profiles closely cluster, i.e. D is small, and those with divergent profiles will have large D values. This type of analysis can reveal, for example, similarities in the mechanism of response of various chemicals. Furthermore, analysis among similar cell types and between different cell types is used to determine what cell, tissue, organ or tumor types may be more or less vulnerable when exposed to a given chemical.

Nucleic Acid Hybridization

Following production of an array of nucleic acid corresponding to expressed RNA products, expression is evaluated for a set of probes. Each of the probes in a set is composed of a unique defined sequence of polynucleotides. Different members of a probe set can be either related or unrelated polynucleotide sequences, and commonly correspond to polynucleotide sequences associated with disease related genes or targets. Frequently, the defined sequence probes are synthetic oligonucleotides, although alternative synthetic probes are also suitable, e.g., cDNA probes, restriction fragments, amplification products, and the like. Hybridization of the plurality of defined sequence probes occurs in a single reaction mixture (hybridization mixture). Differential detection of the different probes is made possible by the inclusion of a different label or signal generating moiety. For example, different defined sequence probes to be analyzed simultaneously in a single hybridization reaction can include different fluorescent labels which can be distinguished on the basis of their emission spectra. Alternatively, each defined sequence probe can incorporate an amplifiable signal element, e.g., an oligonucleotide sequence which can be amplified in a subsequent amplification reaction incorporating a fluorescent or other detectable moiety.

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes*, part I, chapter 2, "Overview of principles of hybridization and the strategy of nucleic acid probe assays," (Elsevier, N.Y.), as well as in Ausubel, supra. Hames and Higgins (1995) *Gene Probes* 1, IRL Press at Oxford University Press, Oxford, England (Hames and Higgins 1) and Hames and Higgins (1995) *Gene Probes* 2, IRL Press at Oxford University Press, Oxford, England (Hames and Higgins 2) provide details on the synthesis, labeling, detection and quantification of DNA and RNA, including oligonucleotides.

"Stringent hybridization wash conditions" in the context of nucleic acid hybridization experiments, such as Southern and northern hybridizations, are sequence dependent, and are different under different environmental parameters. An extensive guide to the hybridization of nucleic acids is found in Tijssen (1993), supra, and in Hames and Higgins 1 and Hames and Higgins 2, supra.

For purposes of the present invention, generally, "highly stringent" hybridization and wash conditions are selected to be about 5° C. or less lower than the thermal melting point ($T_m$) for the specific sequence at a defined ionic strength and pH (as noted below, highly stringent conditions can also be referred to in comparative terms). The $T_m$ is the temperature (under defined ionic strength and pH) at which 50% of the test sequence hybridizes to a perfectly matched primer. Very stringent conditions are selected to be equal to the $T_m$ for a particular primer.

The $T_m$ is the temperature of the nucleic acid duplexes indicates the temperature at which the duplex is 50% denatured under the given conditions and its represents a direct measure of the stability of the nucleic acid hybrid. Thus, the $T_m$ corresponds to the temperature corresponding to the midpoint in transition from helix to random coil; it depends on length, nucleotide composition, and ionic strength for long stretches of nucleotides.

After hybridization, unhybridized nucleic acid material can be removed by a series of washes, the stringency of which can be adjusted depending upon the desired results. Low stringency washing conditions (e.g., using higher salt and lower temperature) increase sensitivity, but can product non-specific hybridization signals and high background signals. Higher stringency conditions (e.g., using lower salt and higher temperature that is closer to the hybridization temperature) lowers the background signal, typically with only the specific signal remaining. See, Rapley, R. and Walker, J. M. eds., *Molecular Biomethods Handbook* (Humana Press, Inc. 1998) (hereinafter "Rapley and Walker"), which is incorporated herein by reference in its entirety for all purposes.

Thus, one measure of stringent hybridization is the ability of the probe to hybridize to one or more of the target nucleic acids (or complementary polynucleotide sequences thereof) under highly stringent conditions. Stringent hybridization and wash conditions can easily be determined empirically for any test nucleic acid.

For example, in determining highly stringent hybridization and wash conditions, the hybridization and wash conditions are gradually increased (e.g., by increasing temperature, decreasing salt concentration, increasing detergent concentration and/or increasing the concentration of organic solvents, such as formalin, in the hybridization or wash), until a selected set of criteria are met. For example, the hybridization and wash conditions are gradually increased until a target nucleic acid, and complementary polynucleotide sequences thereof, binds to a perfectly matched complementary nucleic acid.

A target nucleic acid is said to specifically hybridize to a probe (or primer) nucleic acid when it hybridizes at least ½ as well to the probe as to a perfectly matched complementary target, i.e., with a signal to noise ratio at least ½ as high as hybridization of the probe to the target under conditions in which the perfectly matched probe binds to the perfectly matched complementary target with a signal to noise ratio that is at least about 2.5×-10×, typically 5×-10× as high as that observed for hybridization to any of the unmatched target nucleic acids.

Labels

In the methods of the present invention, multiple probes, each of defined sequence, and each of which is capable of giving rise to a different detectable signal, are hybridized simultaneously, i.e., in a single reaction, to a nucleic acid array. In one favorable embodiment, the probes are each labeled with a different fluorescent chromaphore. A fluorescent label may be covalently attached, noncovalently intercalated, or may be an energy transfer label. Other useful labels include mass labels, which are incorporated into amplification products and released after the reaction for detection, chemiluminescent labels, electrochemical and infrared labels, isotopic derivatives, nanocrystals, or any of various enzyme-linked or substrate-linked labels detected by the appropriate enzymatic reaction.

One preferred embodiment of the methods of the present invention includes the use and detection of one or more fluorescent labels. Generally, fluorescent molecules each display a distinct emission spectrum, thereby allowing one to employ a plurality of fluorescent labels in a single mixed probe reaction, and then separate the mixed data into its component signals by spectral deconvolution. Exemplary fluorescent labels for use in the methods of the present invention include a single dye covalently attached to the molecule being detected, a single dye noncovalently intercalated into product DNA, or an energy-transfer fluorescent label. Numerous suitable combinations of fluorescent labels are known in the art, and available from commercial sources (e.g., Molecular Probes, Eugene Oreg.; Sigma, St. Louis, Mo.).

For example, fluorescent moieties, including Alexa Fluor 350, Alexa Fluor 405, Alexa Fluor 430, Alexa Fluor 488, Alexa Fluor 532, Alexa Fluor 532, Alexa Fluor 546, Alexa Fluor 555, Alexa Fluor 568, Alexa Fluor 594, Alexa Fluor 647, Alexa Fluor 660, Alexa Fluor 680, AMCA, BODIPY 630/650, BODIPY 650/665, BODIPY-FL, BODIPY-R6G, BODIPY-TMR, BODIPY-TRX, carboxyfluorescein, Cascade Blue, Cy3, Cy5, Cy5.5, 6-FAM, Fluorescein, HEX, 6-JOE, Lissamine rhodamine B, Oregon Green 488, Oregon Green 500, Oregon Green 514, Pacific Blue, REG, Rhodamine Green, Rhodamine Red, ROX, SpectrumAqua, TAMRA, TET, Tetramethylrhodamine, and Texas Red, are generally known in the art and routinely used for identification of discreet nucleic acid species, such as in sequencing reactions. One of skill in the art, can easily select dyes having different emission spectra, enabling detection of differently labeled probes hybridized to the same nucleic acid array. One suitable combination compatible with many common lasers and filters includes, e.g., Fluorescein, Texas Red, Cy3, and Cy5, or a combination of, e.g., Alex Fluor dyes according to the manufacturer's instructions (Molecular Probes, Eugene, Oreg.).

The signal strength obtained from fluorescent dyes can be enhanced through use of related compounds called energy transfer (ET) fluorescent dyes. After absorbing light, ET dyes have emission spectra that allow them to serve as "donors" to a secondary "acceptor" dye that will absorb the emitted light and emit a lower energy fluorescent signal. Use of these coupled-dye systems can significantly amplify fluorescent signal. Examples of ET dyes include the ABI PRISM BigDye terminators, recently commercialized by Perkin-Elmer Corporation (Foster City, Calif.) for applications in nucleic acid analysis. These chromaphores incorporate the donor and acceptor dyes into a single molecule and an energy transfer linker couples a donor fluorescein to a dichlororhodamine acceptor dye, and the complex is attached to a DNA replication primer. Alternatively, signals corresponding to hybridization of a probe to a nucleic acid can be amplified using anti-dye antibodies, or enzyme mediated amplification strategies, such as tyramide signal amplification and enzyme labeled fluorescence (ELF) technologies (Molecular Probes, Eugene, Oreg.: additional details can be found in the Molecular Probes handbook and in product literature).

Enzyme-linked reactions theoretically yield an infinite signal, due to amplification of the signal by enzymatic activity. In this embodiment, an enzyme is linked to a secondary group that has a strong binding affinity to the molecule of interest. Following hybridization of an enzyme linked probe to the nucleic acid array, hybridization is detected by a chemical reaction catalyzed by the associated enzyme. Various coupling strategies are possible utilizing well-characterized interactions generally known in the art, such as those between biotin and avidin, an antibody and antigen, or a sugar and lectin. Various types of enzymes can be employed, generating colorimetric, fluorescent, chemiluminescent, phosphorescent, or other types of signals. Following hybridization to an enzyme-linked probe, a chemical reaction is conducted, detecting bound enzyme by monitoring the reaction product. The secondary affinity group may also be coupled to an enzymatic substrate, which is detected by incubation with unbound enzyme. One of skill in the art can conceive of many possible variations on enzyme linked labeling methods.

Alternatively, technologies such as the use of nanocrystals as a fluorescent DNA label (Alivisatos, et al. (1996) Nature 382:609-11) can be employed in the methods of the present invention. Another method, described by Mazumder, et al. (Nucleic Acids Res. (1998) 26:1996-2000), describes hybridization of a labeled oligonucleotide probe to its target without physical separation from unhybridized probe. In this method, the probe is labeled with a chemiluminescent molecule that in the unbound form is destroyed by sodium sulfite treatment, but is protected in probes that have hybridized to target sequence.

Other embodiments of labeling include mass labels, which are incorporated into amplification products and released after the reaction for detection; chemiluminescent, electrochemical, and infrared labels; radioactive isotopes; and any of various enzyme-linked or substrate-linked labels detectable by the appropriate enzymatic reaction. Many other useful labels are known in the art, and one skilled in the art can envision additional strategies for labeling amplification products of the present invention.

Alternatively, the defined sequence probe can include an amplifiable signal element, for example a polynucleotide sequence which can serve as the template in a subsequent amplification reaction, such as a rolling circle amplification (RCA); ramification amplifaction (RAM), branched DNA amplification (BDA); hybridization signal amplification method (HSAM); and 3DNA dendrimer probes (Genisphere, Hatfield, Pa.). Additional methods for amplifying a signal include those described in, e.g., U.S. Pat. Nos. 6,251,639 and 5,545,522. The use of defined sequence probes incorporating amplifiable signal elements is particularly favored when the array comprises RNA or cDNA corresponding to expressed nucleic acids.

Detection Methods

Following hybridization of the defined sequence probes to the nucleic acid array, hybridization between the probes and the nucleic acids of the array is detected and/or detected, and optionally quantitated. Some embodiments of the methods of the present invention enable direct detection of products. Other embodiments detect reaction products via a label associated with one or more of the probes.

A variety of commercially available detectors, including, e.g., optical and fluorescent detectors, optical and fluorescent microscopes, plate readers, CCD arrays, phosphorimagers, scintillation counters, phototubes, photodiodes, and the like, and software is available for digitizing, storing and analyzing a digitized video or digitized optical or other assay results, e.g., using PC (Intel x86 or pentium chip-compatible DOS™, OS2™ WINDOWS™, WINDOWS NT™ or WINDOWS95™ based machines), MACITOSH™, or UNIX based (e.g., SUN™ work station) computers.

One described approach for quantifying fluorescence is to use a photomultiplier tube detector combined with a laser light scanner. Fluorescence imaging can also be performed using a charge-coupled device camera combined, e.g., with a UV light or xenon arc source. Fluorescent dyes with bimodal excitation spectra may be broadly implemented on a wide range of analytical imaging devices, permitting their widespread application to analysis of expression data (e.g., signals corresponding to hybridization between labeled probes and arrayed nucleic acids corresponding to expression products) in semiautomated analysis environments.

For example, the Perkin Elmer ScanArray Express microarray scanner, is capable of monitoring up to 5 dyes simultaneously, and is favorable employed in the methods of the present invention.

Systems for Gene Expression Analysis

The present invention also provides an integrated system for evaluating gene expression. The integrated system typically includes a logical or spatial array, e.g., a microarry organized on a glass slide, incorporating nucleic acid samples corresponding to a plurality of expressed RNA products derived from multiple biological sources or samples, e.g., cell lines, tissues, organ biopsies, organisms, etc. Optionally, the integrated system can include various components for preparation and collection of such biological samples, e.g., providing such functions as cell culture, most commonly in multiwell plates e.g., 96, 384, 768 or 1536 well plates (available from various suppliers such as VWR Scientific Products, West Chester, Pa.). Components and systems for automating the entire process, e.g., sample and reagent pipetting, liquid dispensing, timed incubations, and final readings of the microplate in detector(s) are commercially available, and can be employed in the context of the systems of the present invention (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These configurable systems provide high throughput and rapid start up as well as a high degree of flexibility and customization. Similarly, arrays and array readers are available, e.g., from Affymetrix, PE Biosystems, and others.

The manufacturers of such systems provide detailed protocols the various high throughput. Thus, for example, Zymark Corp. provides technical bulletins describing screening systems for detecting the modulation of gene transcription, ligand binding, and the like.

For example, the system favorably includes a module for RNA isolation. Two commercially available useful in the context of the present invention include platforms marketed by, Qiagen and GenoVision. Qiagen protocols using the 96-well RNeasy product and vacuum filtration can be performed using, e.g., a BioMek Multimek 96-tip pipetting system. This product and protocol isolates total RNA. Alternatively, the GenoVision GenoM-48 and GenoM-96 systems that are capable of isolating mRNA using polyT-conjugated magnetic beads for 48 or 96 samples at a time can be employed for RNA isolation from biological samples. Unlike the Qiagen process that requires user intervention to swap plates, the GenoVision process is fully automated.

The system typically includes an amplification module for producing a plurality of amplification products from a pool of expressed RNA products (e.g., expressed RNA products obtained from a biological sample); a detection module for detecting one or more members of the plurality of amplification products and generating a set of gene expression data; and an analyzing module for organizing and/or analyzing the data points in the data set. Any or all of these modules can comprise high throughput technologies and/or systems.

For example, the amplification module of the system of the present invention produces a plurality of amplification products from an expressed RNA sample. Optionally, the amplification module includes at least one pair of universal primers and at least one pair of target-specific primers for use in the amplification process, as described above. Furthermore, the amplification module can include components to perform one or more of the following reactions: a polymerase chain reaction (e.g., an rtPCR, a multiplex PCR, etc.), a transcription-based amplification, a self-sustained sequence replication, a nucleic acid sequence based amplification, a ligase chain reaction, a ligase detection reaction, a strand displacement amplification, a repair chain reaction, a cyclic probe reaction, a rapid amplification of cDNA ends, an invader assay, a bridge amplification, a rolling circle amplification, solution phase and/or solid phase amplifications, and the like.

The system also includes a hybridization module for contacting a plurality of differently labeled defined sequence probes with the nucleic acid microarray. The hybridization module commonly includes an incubation chamber or coverslip for maintaining conditions suitable for hybridization in solution of the plurality of probes with the nucleic acids disposed on the microarray. Optionally, the hybridization module accommodates additional reagents and reactions for amplifying the hybridization signal. Alternatively, a separate module is included for purposes of amplifying the hybridization signal.

The detection module detects the presence, absence, or quantity of hybridization between the plurality of probes and the microarray. Additionally, the detection module generates a set of gene expression data, generally in the form of a plurality of data points. Most commonly, the data points are recorded in a database. Typically, the data points are recorded in a computer readable medium, i.e., to generate a computer based database.

The third component of the system of the present invention, the analyzing module, is in operational communication with the detection module. The analyzing module of the system includes, e.g., a computer or computer-readable medium having one or more one or more logical instructions for analyzing the plurality of data points generated by the detection system. The analyzing system optionally comprises multiple logical instructions; for example, the logical instructions can include one or more instructions which organize the plurality of data points into a database and one or more instructions which analyze the plurality of data points. The instructions can include software for performing one or more statistical analyses on the plurality of data points. Additionally (or alternatively), the instructions can include or be embodied in software for generating a graphical representation of the plurality of data points. For example, Silicon Genetics' GeneSpring software is one suitable software program for use in the context of the present invention.

The computer employed in the analyzing module of the present invention can be, e.g., a PC (Intel x86 or Pentium chip-compatible DOS™, OS2™ WINDOWS™ WINDOWS NT™, WINDOWS95™, WINDOWS98™, or WINDOWS ME™), a LINUX based machine, a MACINTOSH™, Power PC, or a UNIX based machine (e.g., SUN™ work station) or other commercially common computer which is known to one of skill. Software for computational analysis is available, or can easily be constructed by one of skill using a standard programming language such as VisualBasic, Fortran, Basic, C, C++, Java, or the like. Standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or Paradox™) can also be used in the analyzing system of the present invention.

The computer optionally includes a monitor that is often a cathode ray tube ("CRT") display, a flat panel display (e.g., active matrix liquid crystal display, liquid crystal display), or others. Computer circuitry is often placed in a box that includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user.

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation.

The software can also include output elements for displaying and/or further analyzing raw data, massaged data, or proposed results from one or more computational processes involved in the analysis of the gene expression data set.

Kits

In an additional aspect, the present invention provides kits embodying the methods, compositions, and systems for analysis of gene expression as described herein. For example, a kit of the present invention can include one or more microarray slides (or alternative microarray format) onto which a plurality of different nucleic acid samples, each corresponding to an expressed RNA sample obtained from biological samples, e.g., samples treated with members of a compound library, have been deposited. The kit can also include a plurality of labeled probes. Alternatively, the kit can include a plurality of polunucleotide sequences suitable as probes and a selection of labels suitable for customizing the included polynucleotide sequences, or other polynucleotide sequences at the discretion of the practitioner. Commonly, at least one included polynucleotide sequence corresponds to a control sequence, e.g., β-actin, a "housekeeping" gene, or the like. Exemplary labels include, but are not limited to, a fluorophore, a dye, a radiolabel, an enzyme tag, etc., that is linked to a nucleic acid primer itself.

In one embodiment, kits that are suitable for amplifying nucleic acid corresponding to the expressed RNA samples are provided. Such a kit includes reagents and primers suitable for use in any of the amplification methods described above. Alternatively, or additionally, the kit are suitable for amplifying a signal corresponding to hybridization between a probe and a target nucleic acid sample (e.g., deposited on a microarray).

In addition, one or more materials and/or reagents required for preparing a biological sample for gene expression analysis are optionally included in the kit. Furthermore, optionally included in the kits are one or more enzymes suitable for amplifying nucleic acids, including various polymerases (RT, Taq, etc.), one or more deoxynucleotides, and buffers to provide the necessary reaction mixture for amplification.

Typically, the kits are employed for analyzing gene expression patterns using mRNA as the starting template. The mRNA template may be presented as either total cellular RNA or isolated mRNA; both types of sample yield comparable results. In other embodiments, the methods and kits described in the present invention allow quantitation of other products of gene expression, including tRNA, rRNA, or other transcription products.

Optionally, the kits of the present invention further include software to expedite the generation, analysis and/or storage of data, and to facilitate access to databases. The software includes logical instructions, instructions sets, or suitable computer programs that can be used in the collection, storage and/or analysis of the data. Comparative and relational analysis of the data is possible using the software provided.

The kits optionally comprise distinct containers for each individual reagent and/or enzyme component. Each component will generally be suitable as aliquoted in its respective container. The container of the kits optionally includes at least one vial, ampule, or test tube. Flasks, bottles and other container mechanisms into which the reagents can be placed and/or aliquoted are also possible. The individual containers of the kit are preferably maintained in close confinement for commercial sale. Suitable larger containers may include injection or blow-molded plastic containers into which the desired vials are retained. Instructions, such as written directions or videotaped demonstrations detailing the use of the kits of the present invention, are optionally provided with the kit.

In a further aspect, the present invention provides for the use of any composition or kit herein, for the practice of any method or assay herein, and/or for the use of any apparatus or kit to practice any assay or method herein.

EXAMPLES

The following examples are offered to illustrate, but not to limit the claimed invention. It is understood that the following examples and embodiments described herein are for illustrative purposes only and that various modifications or changes in light thereof will be suggested to persons skilled in the art and are to be included within the spirit and purview of this application and scope of the appended claims.

Example 1

Outline of Analysis

A set of RNA samples (e.g., mRNA samples), each of which is derived from a biological sample, e.g. cells exposed to members of a compound library, is either selectively or globally amplified, optionally by $\geq 3$ logs, to generate cDNA (optionally amplified RNA) populations biased toward a subset of the total RNA population, the entire mRNA population or the entire RNA population. cDNA populations for a plurality of biological samples are spotted onto arrays, preferably optical arrays, e.g. glass slides. Arrays are then probed using a plurality of defined sequence probes (e.g., gene specific nucleic acid probes linked to a label). The label is optionally covalently attached to the probes and optionally a fluorescent tag. Other labels and labeling techniques know in the art may be used. Each of the probes is capable of giving rise to a different detectable signal, e.g., is linked to a different fluorescent label. Following hybridization, the arrays are washed to remove unhybridized probe and a signal corresponding to hybridization between the bound probe and the nucleic acid samples on the microarray are detected.

In an embodiment of this method, the number of biological samples to be analyzed (and optionally, compared for gene expression) exceeds 96 biological samples. Commonly, greater than 960 or more samples are processed and analyzed on a single microarray. Still in further embodiments greater than 9,600 samples are analyzed and compared on one or more microarrays.

Example 2

Amplification of RNA

Typically, it is desirable to increase the amount of nucleic acid via amplification of the RNA population, to provide nucleic acids for spotting in microarrays. While it is envisioned that there will be improvements over time in the sensitivity of microarray detection and analysis, it is generally preferable with current detection strategies and instrumentation to amplify a population of nucleic acids corresponding to one or more species in an expressed RNA sample.

Numerous methods are known in the art for the amplification of nucleic acids in general and RNA specifically. Examples of amplification techniques include PCR, NASBA, TMA, RCA, as well as alternative amplification methods, e.g., as described in Puskas et al. (2002) *Biotechniques* 32:1330-1334; Eberwine (1996) *Biotechniques* 20: 584-591; Van Gelder et al. (1990) *Proc Natl Acad Sci USA* 87:1663-1667; and in U.S. Pat. Nos. 6,251,639, 6, 5,962,271 and 5,545,522. The majority of these methods can be used for either global amplification of nucleic acids, e.g. using random priming and/or poly T priming, or specific amplification using gene or gene family targeted priming.

Global Amplification

Numerous methods have been described for global amplification of an mRNA population. These techniques include various permutations of oligonucleotide polyT primed reverse transcriptions followed by various polymerization schemes using random or semi-random primers (i.e., random or degenerate oligomer primers) to amplify the cDNA population in toto. Methods may use DNA polymerases or a combination of DNA and RNA polymerases.

The primary advantage of global amplification is that the samples, once placed in the array, can be probed for virtually any gene. And multiple arrays can be generated simply by replication to scale up the process for as many genes as is desired. The global amplification approach simplifies the processes associated with preparing samples for arraying since only one protocol and set of reagents is required. In addition, only one purification/desalting processes is required per original RNA sample. All of these elements can lead to a lower overall cost for running the process.

Global amplification has some disadvantages as well. These disadvantages relate to the fact that there is less of each amplified gene within a given sample. The reduced quantity of a given gene may reduce the sensitivity of the assay for that gene relative to some of the more targeted amplification techniques. The presence of an abundance of other genes and their associated nucleic acids also means that there is a higher potential for cross reactivity during the probe hybridization, requiring a more careful selection and analysis of probes during the experimental design phase. Thus for genes expected to be highly expressed, global amplification is often preferable, whereas, in the case of target sequences expressed at lower levels, a greater demand for sensitivity can make selective amplification protocols preferable.

Selective Amplification

Virtually all of the amplification techniques that can be applied to amplifying mRNA may be used to selectively amplify a subpopulation of genes within a given RNA sample. These methods can be as selective as targeting amplification to only a few genes, e.g. the use of rtPCR and a minimal set of gene specific primers, or to a fairly large partition of sequences, e.g. the use of a random set of indexed primers as is common with differential display techniques.

The use of selective amplification has a number of advantages as compared to global amplification. One advantage is the enhancement of the quantities of the specific genes being amplified versus the whole RNA population. This enhancement leads to greater concentrations of the genes to be measured and potentially improved sensitivities and specificities in probe hybridization.

A second advantage of selective amplification is that it can increase the level of multiplexing at the probing level. For example, probing using fluorescently labeled oligonucleotide probes limits the total number of probes that be detected in parallel to the total number of fluorescent chromophores that can be uniquely detected and quantitated by the fluorescence detection system, e.g. commonly no more than 4-5 different chromophores per experiment. Globally amplified RNA products containing copies of all expressed genes can only be probed for a maximum of 4-5 genes at a time, per physical array, meaning that if one wishes to probe for 16-20 different genes, one would need to spot the RNAs onto a minimum of 4 different arrays and probe them independently.

Selective amplification allows for the differential amplification of genes in different samples. Amplification methods that select and amplify certain subsets or subpopulations can be used to partition the RNA into multiple groupings or pools. These groupings provide samples with reduced sequence complexity that offers advantages in probing accurately and selectively for particular sequences. In addition the different partitioned groups can be arrayed on the same surface since there will be limited cross interaction of gene specific probes to the different subpopulations.

For example, genes A-D can be amplified in one reaction, while E-H, I-L, and M-P are amplified in separate reactions. The products of these amplifications can all be spotted on a single array, with each amplification occupying a different spot in the array, and then the array can be probed using probes for all 16 genes simultaneously, wherein probes for genes A, E, I and M all use the first fluorescent chromophore, B, F, J, and N and second chromophore, C, G, K, and O and third chromophore, and so on.

Example 3

On-Chip Signal Amplification

Sensitivity under currently available detection platforms can also be increased using signal amplification following the on-chip hybridization step. There are numerous schemes known in the art for signal amplification. In the case of signal amplification on a microarray, the amplified signal remains localized spatially within the array. Example amplification schemes that can be used include rolling circle amplification (RCA), Ramification Amplification Method (RAM branched DNA amplification (BDA), Hybridization Signal Amplification Method (HSAM), 3DNA dendrimer probes, various fluorescence enhancing schemes, and a number of enzyme-linked signal amplification schemes including various chemi-luminescence, fluorescence and colorimetric approaches. Virtually all of these schemes have been demonstrated to work in the microarray format and provide anywhere from one to five logs of signal amplification. In this invention, it is preferred to use a signal amplification scheme that provides three logs or greater amplification.

Example 4

Screening of a Compound Library

Screening of a compound library is schematically described in FIG. 4. The process involves several principle steps, all of which allow the samples to be handled in parallel in microtiter plate or microarray format. Following the acquisition and lysis of cells, the steps involved are (1) RNA isolation, (2) multiplexed rtPCR, (3) DNA isolation, (4) spotting of the PCR products on the array, and (5) gene-specific probing and detection.

Universal-Primer-Based rtPCR

A population of nucleic acids corresponding to the expressed RNA sample obtained from the cells is generated using a multiplexed rtPCR process. rtPCR using a targeted amplification strategy is performed both for the large gain in sensitivity and because it reduces the complexity of the sample to be analyzed on the array. The use of targeted amplification of a small set of gene versus one of the global RNA amplification methods, such as has been described by Puskas et. al. (2002) *Biotechniques*, 32:6; 1330-1340; and Van Gelder et. al. (1990) PNAS 87:5; 1663-1667, ensures the maximum level of discrimination, limiting cross hybridization to one or more amplified homologous or partially homologous genes.

PCR and rtPCR can be used to amplify a multiplex of targets using very small amounts of material. This utility has been taken advantage of for a variety of applications including genotyping and gene expression. In many cases, especially gene expression, it is desirable to quantitate the relative expression levels for the different nucleic acid targets. However, standard multiplex rtPCR is not typically quantitative. Significant biases can be introduced during the exponential amplification that lead to varied and nonreproducible data. These biases result from primer-primer interactions, primer-product cross-reactions, and from concentration and sequence-dependent variations in amplification efficiency, most notably seen in the latter part or plateau phase of thermal cycling. To overcome these deficiencies the present invention provides a modified rtPCR process that converts PCR to a two-primer process using universal primers.

Figure 8A:
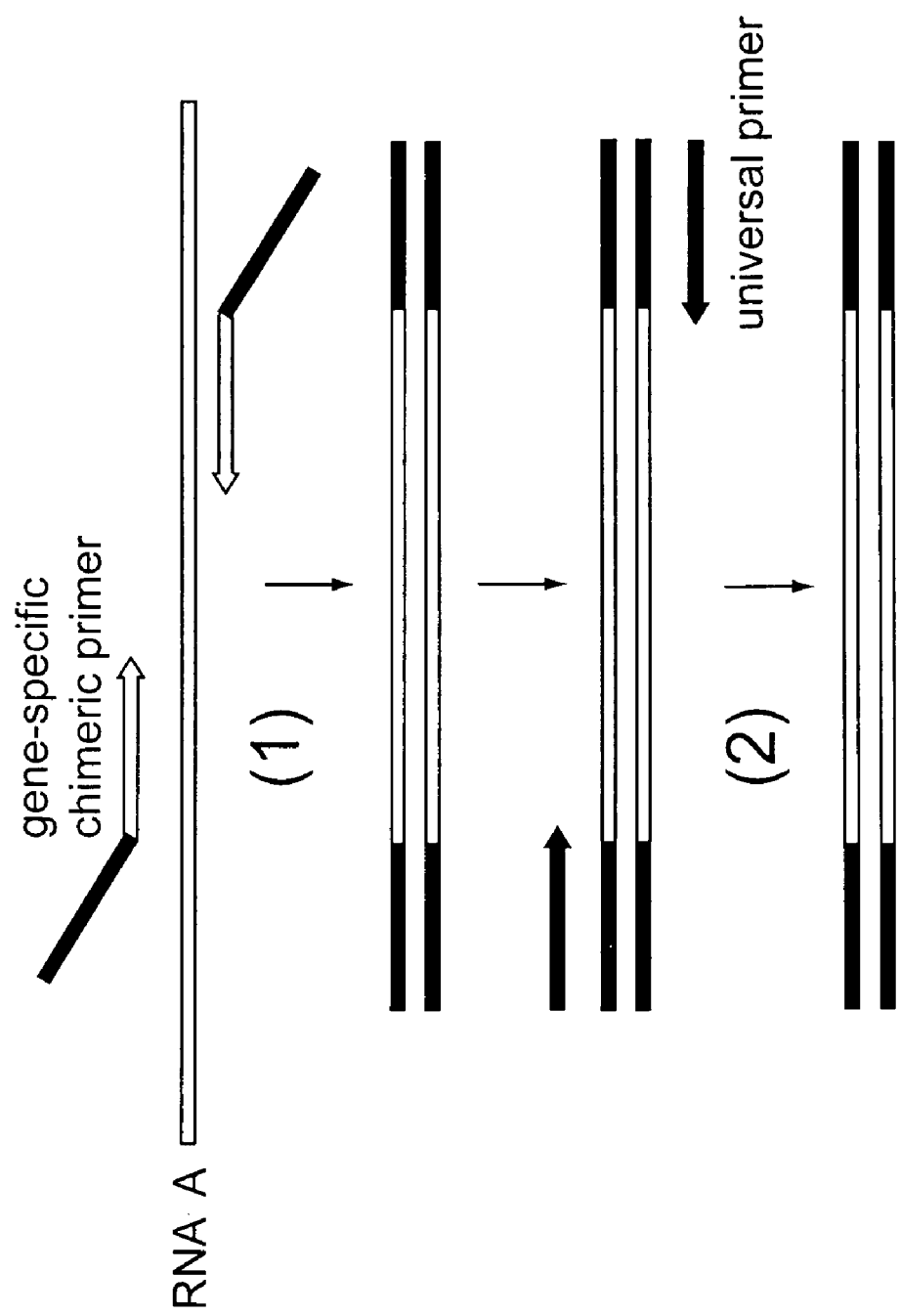
FIGS. 8A and B illustrate a selective amplification protocol and amplification of products in a multiplex amplification reaction, respectively.

The modified rtPCR process uses a combined gene-specific, universal priming strategy that overcomes the primary deficiencies of rtPCR without compromising the detection sensitivity that is gained by using the process. The strategy is outlined in FIGS. 8A & B. Key to the process is the conversion of the multiplex amplification process from one involving tens of primers to one using only two primers. The reaction initializes using gene-specific primers that are capable of specifically detecting each target mRNA. In the first stage (1), chimeric primers comprising both a gene-specific sequence and, on their 5' ends, a consensus or universal sequence, are employed. During the first few cycles of amplification the specific gene targets are amplified by these chimeric primers, creating products that are tailed with the universal primer sequence.

Figure 8B:
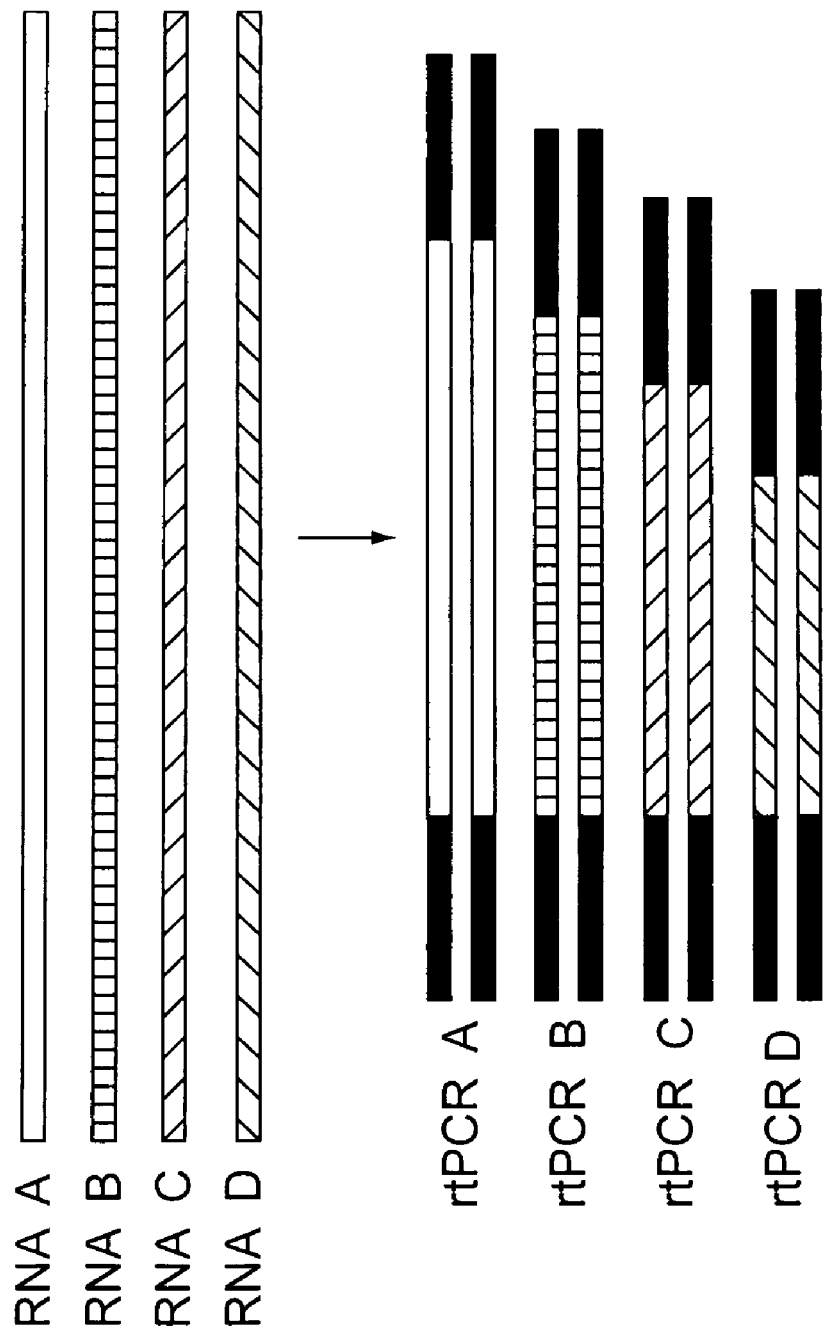

The reactions all carry a pair of universal primers present at significantly higher concentrations, e.g. a universal:chimeric gene-specific primer ratio of 50:1 (1 µM universal:0.02 µM gene specific). Therefore, as PCR progresses the amplification is quickly taken over (2) by the pair of universal primers. This transition from the use of many primers to only two effectively collapses the level of reaction complexity and locks in the relative concentrations of the different gene targets. In the universal primer amplification reaction (shown in FIG. 8B) all the products are effectively the same chemical species and are not differentially amplified. Thus, the relative gene ratios can be maintained even as the reaction pushes into the plateau phase.

The rtPCR process has been validated for nearly five hundred genes, and more than 70 different multiplexes have been built. A variety of different samples have been analyzed including measuring expression response for 13 genes in a screen of a 20,000 compound library, 10×-pooled, measuring responses of ~400 genes to a set of 20 compounds that trigger apoptosis, time course studies tracking the responses for 450 genes to cell treatments by the natural ligands FasL, TRAIL and TNF-alpha, and a single 20-plex to analyze two dozen rat tissue samples.

Timecourse and CVs

Figure 9:
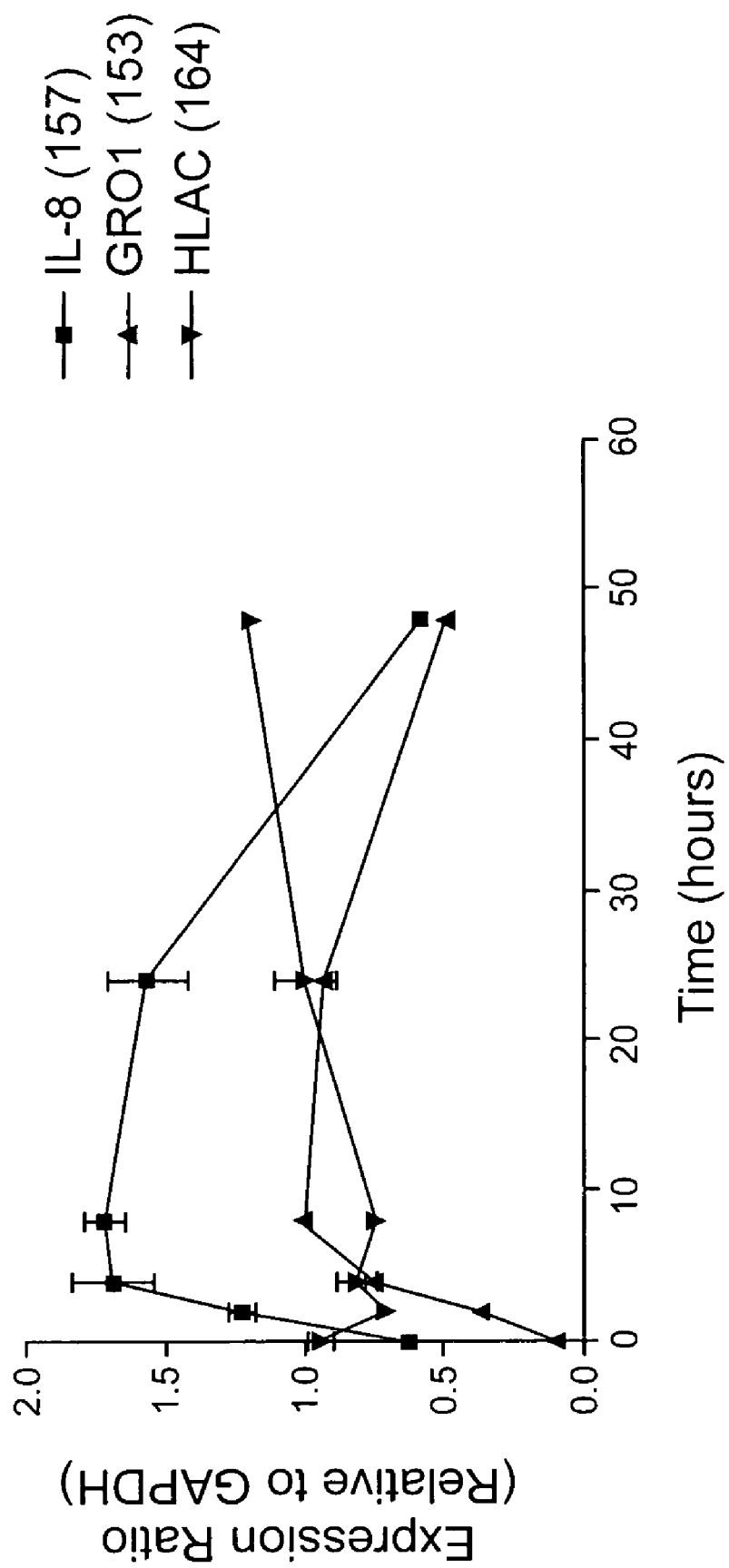
FIG. 9 graphically displays expression profiles for a plurality of genes, of cells treated with a chemical compound (emitine).

FIG. 9 shows is a plot of 3 genes out of a 15-plex from a time course treatment of $5 \times 10^4$ HepG2 cells treated with 25 µM emitine, a protein synthesis inhibitor. Cells were treated in triplicate and timepoints were collected at T=0, 2, 4, 8, 24, 48, and 120 hours. RNA was isolated using Qiagen's RNeasy kit for 96 well plates and the concentration was monitored using a Ribogreen Assay (Molecular Probes). The concentration of RNA from each sample was normalized to 5 ng/µl. rtPCR was carried out using 25 ng of RNA from each sample and the products were analyzed using an ABI 3100 Genetic Analyzer. Gene expression is expressed as a ratio to that of GAPDH. The multiplex included the following list of genes.

| | |
|---|---|
| GRO 1 | melanoma growth stimulating activity, alpha, oncogene |
| IL-8 | interleukin 8 |
| HLA-C | *homo sapiens* major histocompatibility complex C |
| Caspase 3 | apoptosis-related cysteine protease (transcript variant alpha, mRNA) |
| Bak | human bak protein |
| PLAU | plasminogen activator, urokinase |
| IL6ST | interleukin 6 signal transducer (gp130 oncostatin M receptor) |
| Fas | fas ligand |
| Caspase 4 | apoptosis related cysteine protease |
| Serpine 1 | Serine proteinase inhibitor, clade E, number 1 |
| IL-1 | Interleukin receptor, type 2 |
| GAPDH | Glyceraldahyde phoshate dehydrogenase |
| IFNAR2 | Interferon alpha, beta, & omega receptor 2 |
| Caspase 1 | apoptosis-related cysteine protease (IL-1, beta, convertase) |
| Cyclo A | cyclophyllin A |

Examplary data from the multiplex is shown in FIG. 9, with clear trends of induction for Il-8 and GRO1. CV's for all genes and data points within the experiment ranged from a few percent to 20%.

Linearity and Dynamic Range

Figure 10:
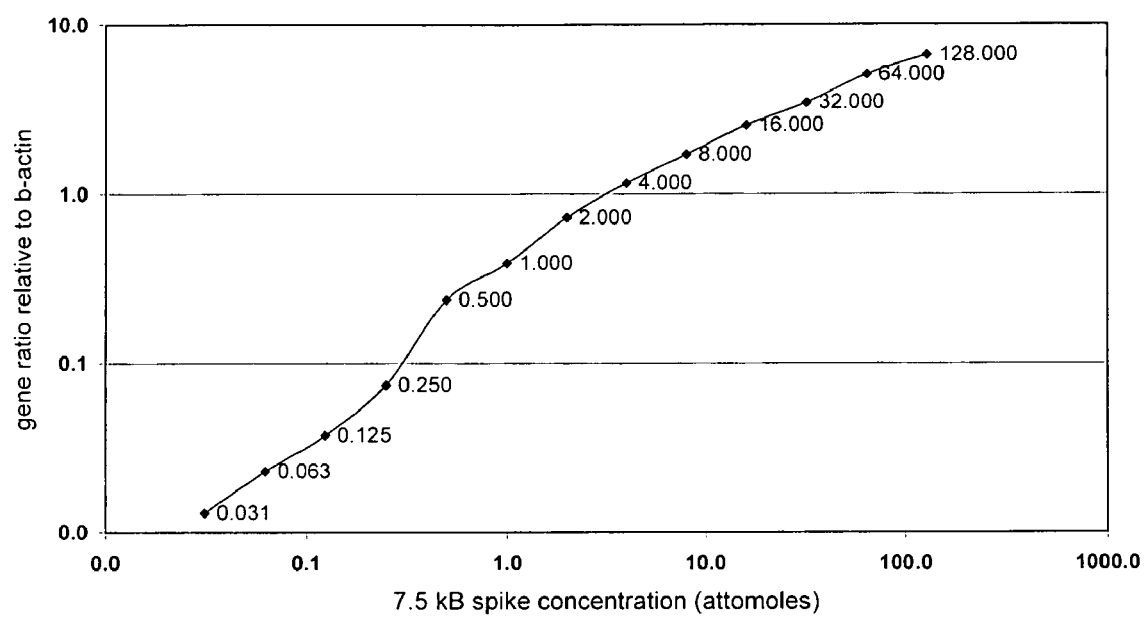
FIG. 10 graphically displays the linearity and dynamic range of a amplification reaction relative to β-actin.

The universal-primer-based rtPCR approach shows a wide dynamic range and linear dose-response. To assess the dynamic range of RNA detection by the assay, a commercially available purified 7.5 kb RNA (Gibco), also used as an external control, was spiked into 20 ng of total RNA from cultured PC-3 cells in the range of 0.004 to 125 attomoles. The quantities of specific PCR product, relative to β-actin, were determined. The dose-response was linear over this range of over 3 orders of magnitude (FIG. 10). It should be noted that this wide dynamic range, is actually the range of the measured gene expression ratio relative to β-actin (attenuated) as indicated on the Y axis. This range permits measurements of fold change differences in gene expression of multiple comparative samples of many orders of magnitude. Additionally, it allows the simultaneous measurement of high and low copy number transcripts.

This experiment also demonstrated that the minimum detectable level of spiked 7.5 kb RNA that could be distinguished from zero was 31 zeptomoles, or $1.9 \times 10^4$ molecules, indicated on the X axis. Thus the assay can detect on the order of one transcript copy per cell using $10^4$ cells. Furthermore, it is expected that utilization of a microarray format readout will provide an additional sensitivity increase that can be used to reduce the required RNA per reaction by at least 2 logs, down into the sub-nanogram levels. Such a sensitivity increase makes it possible to run multiple multiplex reactions using only a few nanograms of RNA, and enables researchers to measure expression values for hundreds of genes using very small tissue samples such as those that can be acquired and selected using laser capture microdissection.

Other Benefits of Universal-Primer-Based rtPCR

By limiting the concentration of gene-specific primers and using universal primers for the bulk of the amplification process we gain the added benefit of relaxing the constraints associated with the design of successful gene-specific primers. With the concentrations of the gene-specific primers kept low (0.02 µM) their participation in cross-reactions and mis-reactions is limited, leading to a higher probability of success in amplification with a significantly reduced likelihood for creating artifacts.

Another major advantage of the technology is that the format is highly flexible in terms of the numbers of genes versus numbers of samples used in a study. For example, performance of 5,000 multiplex rtPCR reactions with 20 genes per reaction generates ~100,000 data points. These 5,000 reactions can be used to measure 20 genes for 5,000 samples, 100 genes for 1,000 samples, 200 genes for 500 samples, or 1,000 genes for 100 samples. Note that, as will be described in the research plan, it is very straightforward to spot all 5,000 reactions onto a single microarray slide for analysis.

Flipping the Microarray Paradigm

The analysis process involves flipping the current microarray paradigm, wherein the rtPCR products derived from the RNA samples are assembled into an array, and the gene-specific oligonucleotide probes are hybridized to these arrays, as opposed to the probes being placed on the surface and the samples in solution.

Standard microarrays differentiate the many genes being monitored using specific spatial placement of gene-specific probes on the microarray surface. The methods of the present invention use gene specific-probes that are differentiated by the use of two to five different labels, e.g., fluorescent labels that can be uniquely identified by their absorption/emission properties. While this approach does limit the number of genes that can be probed within any single multiplexed rtPCR sample (an issue that is resolved simply by making multiple replicates of an array) it leaves free the use of the spatial arraying dimensions to parallelize the analysis of samples at a level of 1 to 2 orders of magnitude higher than can be attained using microtiter plate formats.

The process is shown schematically in FIG. 1, wherein a large set of RNA samples, commonly arrayed in microtiter plates, provide the source to generate a series of rtPCR reactions that are then arrayed on one or more microarray slides. Typical microarray slides can contain anywhere from a couple thousand to 20,000 "spots" where samples are uniquely placed. Therefore, as many as 20,000 different amplified samples can be placed and probed on a single slide. In the example shown in FIG. 1, the slide is probed using 4 different oligonucleotide probes that target 4 different genes. The different probes carry 4 different fluorescent labels that can be uniquely detected and quantitated in the array reader.

The ability to analyze 4 different genes for 20,000 samples on a given slide may seem limited in terms of gene depth. However, as stated above, it is trivial to replicate a given slide using existing slide printing instruments to generate upwards of 100 or more slides per set of samples. This replication process is shown schematically in FIG. 2, and clearly shows how through the use of replicates many more genes can be analyzed from these same RNA samples. The processes of printing, probing and scanning the microarray plates is a near parallel process, therefore, it takes roughly the same time and resources to analyze 20 plates as it does 1 (hours difference not days).

The methods of the present invention offer many advantages over commonly used dot blot methods. These advantages include a 3-4 log increase in sensitivity leading to the use of much smaller quantities of RNA, multiplexing in probing and detection that increases throughput and enables internal sample measurement of gene to control RNA ratios, and greatly improved levels of probe discrimination through the use of rtPCR to reduce sample complexity. The process adds complexity in terms of the number of sample handling steps, but the use of current automated liquid handling, e.g., pipetting, tools limits opportunities for sample mixups and pipetting variability while minimizing reagent usage.

Internal Reference Control+Number of Dyes

In the example described above, the gene expression values are relative expression values. Specifically, each rtPCR multiplex includes the amplification of one or more "control" or "reference" genes. Example reference genes include the usual suspects of β-actin, GAPDH, cyclophyllin and others. The consequence is that one of the oligonucleotide probes used to monitor each microarray needs to be used for a reference or control gene. Therefore, if one is using 2 dyes per probing then one can only measure one gene plus the reference. Using 5 dyes one can monitor 4 genes plus the reference. The number of dyes that can be used will need to be tested empirically, but we will utilize a state-of-the-art array scanner, such as the Perkin Elmer ScanArray Express, that can monitor up to 5 dyes simultaneously. The number of dyes used directly correlates to the number of microarray plate replicates that need to be made. For example, an rtPCR multiplex of 20 genes will need to be replicated onto 20 plates if only 2 dyes are used for analysis (1 gene per array+reference), or on to 5 plates if 5 dyes are used (4 genes per array+reference).

Arraying Strategies

So far we have discussed only one arraying strategy for this technology, namely where a single multiplex of ~20 genes is used to amplify 10,000 samples to fill up the array. There are, however, other schemes in which multiple multiplexes can be spotted onto the same array. Because each rtPCR only amplifies a targeted set of genes, experiments can be designed where multiple multiplexes are used to amplify 100 genes for example. In the 100 gene scenario, 5 different multiplexes of 20 genes are independently spotted onto the microarray surface. In a 10,000 spot array, 5 different multiplexes can be spotted for 2,000 different biological samples. For each multiplex 4 gene-specific oligonucleotide probes (plus a reference) are created with a different dye conjugated to each. The probes for each of the 5 different multiplexes can then be pooled and simultaneously hybridized to the microarray. Because each probe will only hybridize to a single gene in a single multiplex (unless otherwise desired such as in the case of a standard reference gene), and the different spot addresses are tracked for multiplex identity, the different fluorescence signals can be directly correlated to an individual gene. Of course, the typical concerns about homologies and cross hybridization need to be considered during the experimental design phase.

In either the single or multiple multiplex case, the number of array replicates needed is directly related to the size of the largest multiplex used and the number of fluorescent dyes that can be simultaneously detected.

Example 5

Exemplary Protocol

The following provides an exemplary procedure for the amplification and array hybridization in the context of screening compound libraries according to the methods of the invention.

Amplification of RNA Using Multiplex Universal Primer Driven PCR

Total RNA was obtained from cultured cells using an RNA isolation kit (Qiagen Rneasy). 20 ng of isolated RNA was then used first in a reverse transcription reaction and the PCR. Thirty-one genes were targeted for amplification with the primers given in Table 1, according to the following conditions.

| Reverse Transcription | |
|---|---|
| Gene Specific Reverse Primer | @ 0.05 μM |
| Tris-HCl | 10 mM |
| pH | 8.3 |
| KCl | 50 mM |
| MgCl | 2.5 mM |
| dNTPs | 1 mM |
| DTT | 0.01 M |
| Rnase Inhibitor | 0.1 U |
| MMLV Reverse Transcriptase | 1.0 U |
| Volume | 20 μl |
| Thermal Cycler Conditions | |
| 48° C. | 1 minute |
| 37° C. | 5 minutes |
| 42° C. | 60 minutes |
| 95° C. | 5 minutes |
| 4° C. | end |
| Polymerase Chain Reaction | |
| cDNA | 10 μl* |
| Gene Specific Forward Primer | @ 0.02 μM |

-continued

| | |
|---|---|
| Tris-HCl | 10 mM |
| pH | 8.3 |
| KCl | 50 mM |
| MgCl | 7 mM |
| dNTPs | 0.3 mM |
| Universal Forward Primer | 1 μM |
| Universal Reverse Primer | 1 μM |
| Taq Polymerase | 2.5 U |
| Volume | 20 μl |
| Thermal Cycler Conditions | |
| 95° C. | 10 minutes |
| 94° C. | 30 seconds |
| 55° C. | 30 seconds |
| 68° C. | 60 seconds |
| repeat steps 2-4 35 cycles | |
| 4° C. | end |

*of 20 μl reverse transcription reaction

TABLE 1

Multiplex Amplification Primers

| Name | Access # | Size | Forward Primer | Reverse Primer |
|---|---|---|---|---|
| Multiplex 1 | | | | |
| AP2B1 | NM_001282 | 100 | AGGTGACACTATAGAATATTTCCCCTCCAAACTCCTTT (SEQ ID NO: 1) | GTACGACTCACTATAGGGAAAGATCACCGTTCCCAACTG (SEQ ID NO: 2) |
| FLJ11190 | NM_018354 | 107 | AGGTGACACTATAGAATATTTCCTGGTGAGTGGGATTC (SEQ ID NO: 3) | GTACGACTCACTATAGGGATCTCCAGTCGTTCCATCTCC (SEQ ID NO: 4) |
| MP1 | NM_014889 | 125 | AGGTGACACTATAGAATAGACCCAGATCATGCCAGTCT (SEQ ID NO: 5) | GTACGACTCACTATAGGGAAAAATCCCATTGTGGCTGAG (SEQ ID NO: 6) |
| ESTs(#2) | AI918032 | 131 | AGGTGACACTATAGAATAGTTCCTATCCTCCTGTGGCA (SEQ ID NO: 7) | GTACGACTCACTATAGGGAACAAATCGGTAACCAGCAGC (SEQ ID NO: 8) |
| CENPA | NM_001809 | 137 | AGGTGACACTATAGAATATTCATCTCTTTGAGGACGCC (SEQ ID NO: 9) | GTACGACTCACTATAGGGAAGAAACACTGGGTGCAGGAG (SEQ ID NO: 10) |
| TGFB3 | NM_003239 | 143 | AGGTGACACTATAGAATAGGTTGGATTTGCTCATTGCT (SEQ ID NO: 11) | GTACGACTCACTATAGGGATTGCCCTTAATCCCAGACAG (SEQ ID NO: 12) |
| CCNE2 | NM_004702 | 150 | AGGTGACACTATAGAATACCGAAGAGCACTGAAAAACC (SEQ ID NO: 13) | GTACGACTCACTATAGGGAGAATTGGCTAGGGCAATCAA (SEQ ID NO: 14) |
| SM-20 | W90004 | 156 | AGGTGACACTATAGAATAGTCCTGCTTGGTGACAAGTT (SEQ ID NO: 15) | GTACGACTCACTATAGGGATGCTTGCCAGACAGGTCTTA (SEQ ID NO: 16) |
| WISP1 | NM_003882 | 163 | AGGTGACACTATAGAATATTCCTGTTGATGGGAAAAGC (SEQ ID NO: 17) | GTACGACTCACTATAGGGACAAGCAGGACAAGGGAGAAG (SEQ ID NO: 18) |
| GSTM3 | NM_000849 | 174 | AGGTGACACTATAGAATATTTCATCCTGTCCGTAAGGG (SEQ ID NO: 19) | GTACGACTCACTATAGGGATAGGGAAATGCCAGTATCGC (SEQ ID NO: 20) |
| BBC3 | U82987 | 180 | AGGTGACACTATAGAATATGAAGAGCAAATGAGCCAAA (SEQ ID NO: 21) | GTACGACTCACTATAGGGAACAGGATTCACAGTCTGGGC (SEQ ID NO: 22) |
| KIAA1442 | AB037863 | 186 | AGGTGACACTATAGAATACAGCTCAGGGAGAAGTGACC (SEQ ID NO: 23) | GTACGACTCACTATAGGGAGCAGGTCTCAAAGGAAGTGG (SEQ ID NO: 24) |
| ESTs(#4) | AA528243 | 193 | AGGTGACACTATAGAATACAGAGGAGCTTGTACCCACC (SEQ ID NO: 25) | GTACGACTCACTATAGGGACACTTCTGCATCACGGAAGA (SEQ ID NO: 26) |
| ALDH4 | NM_003748 | 200 | AGGTGACACTATAGAATATCTCTGCAGTGATTGATGCC (SEQ ID NO: 27) | GTACGACTCACTATAGGGAAGACAGTACAGGCCCGAAGA (SEQ ID NO: 28) |
| CEGP1 | NM_020974 | 206 | AGGTGACACTATAGAATATCTGCTATAGGGTTGGTGGG (SEQ ID NO: 29) | GTACGACTCACTATAGGGACAGCAGTGAGAAGCTGATGC (SEQ ID NO: 30) |

TABLE 1-continued

Multiplex Amplification Primers

| Name | Access # | Size | Forward Primer | Reverse Primer |
|---|---|---|---|---|
| PECI | NM_006117 | 212 | AGGTGACACTATAGAATAGTCCGAGTTCTCTGCAGGTC (SEQ ID NO: 31) | GTACGACTCACTATAGGGAAAATACACCTGGTTTGGGCA (SEQ ID NO: 32) |
| ESM1 | NM_007036 | 218 | AGGTGACACTATAGAATAGGAGAAACTTGCTACCGCAC (SEQ ID NO: 33) | GTACGACTCACTATAGGGAAGGGGAATTTCAGGCATTT (SEQ ID NO: 34) |
| FLJ11354 | AI583960 | 230 | AGGTGACACTATAGAATATTTTTCCCTGTGTTCTTGGG (SEQ ID NO: 35) | GTACGACTCACTATAGGGAAAGGAGGTGCAACCACACAT (SEQ ID NO: 36) |
| CFFM4 | AF201951 | 236 | AGGTGACACTATAGAATACCAACAGAAACCACCGTTCT (SEQ ID NO: 37) | GTACGACTCACTATAGGGAGAGGTCAAGCTGCTCAGGTC (SEQ ID NO: 38) |
| NMU | NM_006681 | 246 | AGGTGACACTATAGAATACCAAAGCCTCAGGAACAAGA (SEQ ID NO: 39) | GTACGACTCACTATAGGGATGCTGACCTTCTTCCATTCC (SEQ ID NO: 40) |
| HAS 250839 | NM_018401 | 255 | AGGTGACACTATAGAATAGGGCTGTCCATGTCATCTCT (SEQ ID NO: 41) | GTACGACTCACTATAGGGACCAGGGTCACAGTAGGGAGA (SEQ ID NO: 42) |
| ESTs(#3) | AI694320 | 261 | AGGTGACACTATAGAATATCTTGCCCCTGATATCACAA (SEQ ID NO: 43) | GTACGACTCACTATAGGGAACCTCTTGTGCATTCTGCAA (SEQ ID NO: 44) |
| FGF18 | NM_003862 | 267 | AGGTGACACTATAGAATAGCCCTGATGTCGGCTAAGTA (SEQ ID NO: 45) | GTACGACTCACTATAGGGATGCAGTTTTCTGGGAGTGTG (SEQ ID NO: 46) |
| ESTs(#5) | AA834945 | 273 | AGGTGACACTATAGAATAATGGATGAAACAGCTGAGCA (SEQ ID NO: 47) | GTACGACTCACTATAGGGAGCGCTCTACGCAAAGTGAAT (SEQ ID NO: 48) |
| PRC1 | NM_003981 | 118 | AGGTGACACTATAGAATATGTGGGAACAGGAACATTCA (SEQ ID NO: 49) | GTACGACTCACTATAGGGATGTCTTTCCTGCTTGGCTCT (SEQ ID NO: 50) |
| FLT1 | NM_002019 | 168 | AGGTGACACTATAGAATATTCTACATTTGAGGGCCCAG (SEQ ID NO: 51) | GTACGACTCACTATAGGGACAAAACATGCCACGAATGAG (SEQ ID NO: 52) |
| IGFBP5 | L27560 | 112 | AGGTGACACTATAGAATAGCAATCTAAGCAGGGGTCTG (SEQ ID NO: 53) | GTACGACTCACTATAGGGACAGCACTTAGATTCGGAGCC (SEQ ID NO: 54) |
| AKAP2 | NM_007203 | 298 | AGGTGACACTATAGAATATAACATGGAGGAGACCAGGC (SEQ ID NO: 55) | GTACGACTCACTATAGGGACCCTGGAGCAGTTTTGTAGC (SEQ ID NO: 56) |
| Multi-plex 2 | | | | |
| FLJ22719 | AI283268 | 100 | AGGTGACACTATAGAATAGGGAATCGGAAGGGTTCATA (SEQ ID NO: 57) | GTACGACTCACTATAGGGAGGAGGGACCAACCTTGAAAT (SEQ ID NO: 58) |
| KIAA 0175 | NM_014791 | 106 | AGGTGACACTATAGAATACTGTCAGAAGAGGAGACCCG (SEQ ID NO: 59) | GTACGACTCACTATAGGGAGCAAATTTTCTGGCTTGAGG (SEQ ID NO: 60) |
| RFC4 | NM_002916 | 112 | AGGTGACACTATAGAATATCAGTACTAAACCCCCGCTG (SEQ ID NO: 61) | GTACGACTCACTATAGGGATTTGGGCGATATTTTTCCAC (SEQ ID NO: 62) |
| LOC 57110 | NM_020386 | 121 | AGGTGACACTATAGAATAGAAGTGTTCCGTCCTGGCTA (SEQ ID NO: 63) | GTACGACTCACTATAGGGATGCTGAATACAGACTTGGCG (SEQ ID NO: 64) |
| TMEFF1 | AI741117 | 130 | AGGTGACACTATAGAATAGGGGGTTTATGAGCCACATT (SEQ ID NO: 65) | GTACGACTCACTATAGGGATTTAGGGAACCTCCGTGAGA (SEQ ID NO: 66) |
| FLJ22477 | AI817737 | 136 | AGGTGACACTATAGAATATGGGTGTGGATTCTGTTCTG (SEQ ID NO: 67) | GTACGACTCACTATAGGGATGGGGTTTGAAGTTGGAATC (SEQ ID NO: 68) |
| OXCT | NM_000436 | 144 | AGGTGACACTATAGAATATGCAAAGGGAAATGCACATA (SEQ ID NO: 69) | GTACGACTCACTATAGGGACCTTCCCAGAGCTCAATCAG (SEQ ID NO: 70) |
| MMP9 | NM_004994 | 154 | AGGTGACACTATAGAATACGAACTTTGACAGCGACAAG (SEQ ID NO: 71) | GTACGACTCACTATAGGGACCCTCAGTGAAGCGGTACAT (SEQ ID NO: 72) |
| UCH37 | NM_015984 | 160 | AGGTGACACTATAGAATACGCAAAGAAAGCTCAGGAAA (SEQ ID NO: 73) | GTACGACTCACTATAGGGAAGACAAGACAGGCTGGCACT (SEQ ID NO: 74) |
| SERF1A | AF073519 | 168 | AGGTGACACTATAGAATATCTCCATCTCCTGACCTCGT (SEQ ID NO: 75) | GTACGACTCACTATAGGGACTTGGTCTCCCAAAGTGCTC (SEQ ID NO: 76) |
| MCM6 | NM_005915 | 177 | AGGTGACACTATAGAATAGGTGGAGCAGTTCCTGTGTT (SEQ ID NO: 77) | GTACGACTCACTATAGGGATTCACATTGCACTGGAAAGC (SEQ ID NO: 78) |

TABLE 1-continued

Multiplex Amplification Primers

| Name | Access # | Size | Forward Primer | Reverse Primer |
|---|---|---|---|---|
| SLC2A3 | NM_006931 | 183 | AGGTGACACTATAGAATAACCGGCTTCCTCATTACCTT (SEQ ID NO: 79) | GTACGACTCACTATAGGGAGACATTGGTGGTGGTCTCCT (SEQ ID NO: 80) |
| ORC6L | NM_014321 | 194 | AGGTGACACTATAGAATATCCAGGCCACTTTTCACTTC (SEQ ID NO: 81) | GTACGACTCACTATAGGGACTCTTCCGTGGTGGAGTAGC (SEQ ID NO: 82) |
| DCK | NM_000788 | 201 | AGGTGACACTATAGAATAGTGGTTCCTGAACCTGTTGC (SEQ ID NO: 83) | GTACGACTCACTATAGGGAGAGCTTGCCATTCAGAGAGG (SEQ ID NO: 84) |
| PK428 | NM_003607 | 207 | AGGTGACACTATAGAATAGAAGGGAGAGGAAGGGAGTG (SEQ ID NO: 85) | GTACGACTCACTATAGGGATCAAAGGACACAACGAGCAG (SEQ ID NO: 86) |
| COL4A2 | X05610 | 215 | AGGTGACACTATAGAATAGGACGAGATCAAGCCCTACA (SEQ ID NO: 87) | GTACGACTCACTATAGGGACGCGGAAGTCCTCTAGACAG (SEQ ID NO: 88) |
| HEC | NM_006101 | 221 | AGGTGACACTATAGAATATGGATCCCGGAATAGTCAAC (SEQ ID NO: 89) | GTACGACTCACTATAGGGAGGCACAGGAAGCCATAAAGA (SEQ ID NO: 90) |
| L2DTL | NM_016448 | 227 | AGGTGACACTATAGAATATTTTGGGACGTAAAAGCTGG (SEQ ID NO: 91) | GTACGACTCACTATAGGGATTTGAAGGGGTTTGCTTGTC (SEQ ID NO: 92) |
| FLJ12443 | AF052162 | 233 | AGGTGACACTATAGAATACTTCCTGCAGAGAGAGGAGC (SEQ ID NO: 93) | GTACGACTCACTATAGGGAACACCAAAATACCCCATCCA (SEQ ID NO: 94) |
| RAB6B | NM_016577 | 242 | AGGTGACACTATAGAATAATGTACTTGGAGGACCGCAC (SEQ ID NO: 95) | GTACGACTCACTATAGGGATGCCTCTTATCAGCCAGGTC (SEQ ID NO: 96) |
| ESTs (#7) | AI992158 | 248 | AGGTGACACTATAGAATAAACATTGAATGGCACAGCAA (SEQ ID NO: 97) | GTACGACTCACTATAGGGAAACCAGGCACAAGGTTCAAG (SEQ ID NO: 98) |
| DKFZP-564D0462 | AL080079 | 256 | AGGTGACACTATAGAATAATTCTGGCAAAGCCAATCTG (SEQ ID NO: 99) | GTACGACTCACTATAGGGAGATGGTGTTGCAGGATGTTG (SEQ ID NO: 100) |
| FLJ13997 | AI377418 | 262 | AGGTGACACTATAGAATAATCAGCATTTCCAACCACAA (SEQ ID NO: 101) | GTACGACTCACTATAGGGAGTCTCGCTAATAACCCCAGC (SEQ ID NO: 102) |
| ECT2 | AI738508 | 268 | AGGTGACACTATAGAATATTGTACAATACAACGGGCGA (SEQ ID NO: 103) | GTACGACTCACTATAGGGATTGGTTCAAGAAGCTGGAAAA (SEQ ID NO: 104) |
| ESTs (#8) | AI224578 | 274 | AGGTGACACTATAGAATAGGACACATGGAACAAACCAA (SEQ ID NO: 105) | GTACGACTCACTATAGGGAAATGTTTCTCCTGGTTGGGA (SEQ ID NO: 106) |
| ESTs (#6) | AW024884 | 149 | AGGTGACACTATAGAATACTGACATGCTCACGCTCTG (SEQ ID NO: 107) | GTACGACTCACTATAGGGACCCCATACCTTGATGGAGAA (SEQ ID NO: 108) |
| IGFBP5 | NM_000599 | 299 | AGGTGACACTATAGAATAGGGTGAACAATTTTGTGGCT (SEQ ID NO: 109) | GTACGACTCACTATAGGGACGAGAGTGCAGGGATAAAGG (SEQ ID NO: 110) |
| GMPS | NM_003875 | 189 | AGGTGACACTATAGAATATACCTCGCATGTGTCACAACG (SEQ ID NO: 111) | GTACGACTCACTATAGGGACCGGCATCTGGCTGATTTT (SEQ ID NO: 112) |
| Universal Primer | | | AGGTGACACTATAGAATA (SEQ ID NO: 113) | GTACGACTCACTATAGGGA (SEQ ID NO: 114) |

Note:
The target specific primers for each gene sequence can be deduced from the above given sequences by deleting the universal primer sequences, SEQ ID NO: 113 and SEQ ID NO: 114, from the 5' end of each forward and reverse sequence, respectively. Thus, for example the target specific primer (and the target specific portion of the chimeric primer) of SEQ ID NO: 1 is TTTCCCCTCCAAACTCCTTT.

Microarray Spotting of PCR Products

Figure 11:
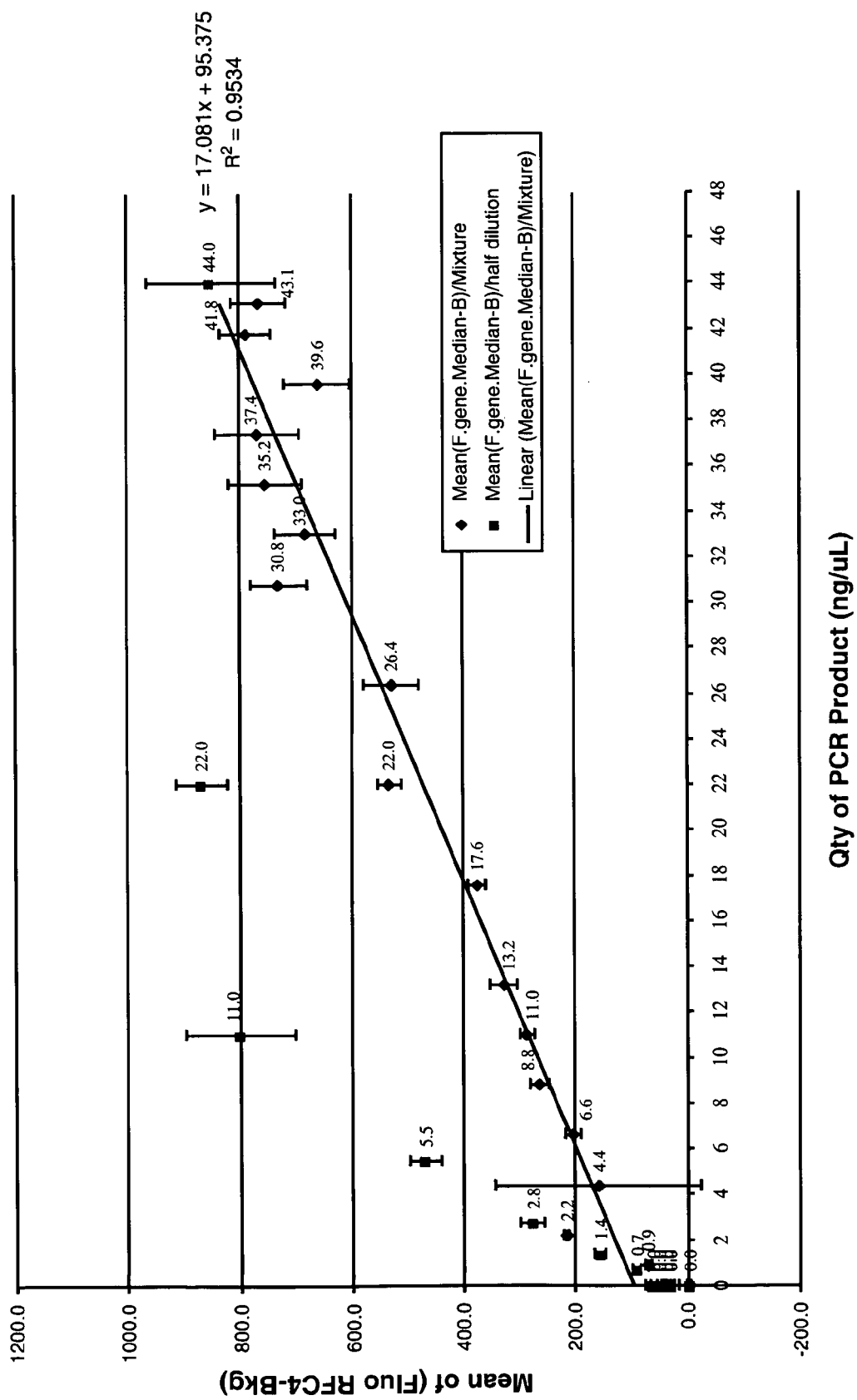
FIG. 11 illustrates data collected from an exemplary microarray experiment. Intensity of fluoresecence indicates quantitative hybridization of a labeled probe with increasing concentrations of multiplexed PCR amplification product including the target.

PCR products were purified using Promega Wizard PCR purification kits and protocols. The PCR products were then diluted and mixed with DMSO to a final concentration of 50% DMSO. As shown in FIG. 11, rtPCR reactions were performed independently using multiplexes 1 and 2 on an RNA sample. The two PCR reactions were purified and then mixed together in different ratios ranging from 99:1 to 1:99 wherein the total amount of PCR product had a final concentration of 44 ng/μl. The PCR/DMSO mix was then spotted onto aminosilane coated slides (Sigma) in 12 replicates and baked at 85° C. for 1 hour to immobilize the DNA. The spotted slides were prehybridized with 5×SSC buffer containing 0.1% SDS and 1% BSA at 42° C. for 45 minutes. The slide was then washed twice with water and once with isopropanol then dried.

Probe Hybridization

Fluorescently labeled oligonucleotide probe, e.g. end labeled with Cy3 or Cy5, was prepared at a concentration of 1 μM in 1× hybridization buffer (4×SSC, 0.02% Tween20, 1 Unit/ml poly dA, and 1 μg/μl yeast tRNA). In the example illustrated in FIG. 11, an oligonucleotide probe for the gene RFC4 (Cy5) present only in multiplex 2 was incubated at 95° C. for 3 minutes and 4° C. for 30 seconds. 35 μl of probe was added to the prepared microarray slides, covered with a microscope glass coverslip and incubated in a humidified chamber at 42° C. for 1 hour. Following hybridization, the coverslip was removed and the slides were washed first with a low stringency buffer containing 1×SSC and 0.2% SDS at 42° C., then twice with a high stringency buffer containing 0.1×SSC and 0.2% SDS at 22° C., and finally twice with 0.1×SSC at 22° C. The slides were then dried and scanned.

Slide Scanning

Scanning was performed using an Axon Instruments Gene-Pix microarray scanner using the standard protocols recommended by the manufacturer. Data was then imported into Axon Acuity software for analysis. As shown in FIG. 11, the amount of fluorescence signal increases as the quantity of multiplex 2 in the sample increases from 0 to 44 ng/μl.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A hybridization system comprising:
    (a) an array comprising at least 500 nucleic acid samples that each comprise a plurality of different nucleic acids, wherein each nucleic acid sample is deposited at a single unique location on the array, wherein each nucleic acid sample is produced from a biological sample that has been contacted with at least one member of a compound library prior to producing the nucleic acid sample, and wherein the plurality of different nucleic acids in each nucleic acid sample comprises subsequences of at least two different genes in the biological sample; and,
    (b) a plurality of solution-based, defined sequence probes wherein each comprises a subsequence of a different gene in the biological sample, and wherein each probe is capable of generating a different detectable signal.

2. The hybridization system of claim 1, wherein the at least 500 nucleic acid samples are selected from:
    (i) total cellular RNA or a subset thereof derived from the biological sample;
    (ii) mRNA isolated from the biological sample;
    (iii) cDNA produced from (i) or (ii); and
    (iv) nucleic acids amplified from (i), (ii), or (iii).

3. The hybridization system of claim 1 wherein the plurality of defined sequence probes comprises a set of genes comprising disease-related targets.

4. The hybridization system of claim 1, wherein the array comprises a two-dimensional solid-phase surface.

5. The hybridization system of claim 1, wherein the array comprises a plurality of solid-phase surfaces.

6. The hybridization system of claim 5, wherein the plurality of solid-phase surfaces are selected from the group consisting of: beads, spheres, and optical fibers.

7. The hybridization system of claim 6, wherein the array comprises a solid-phase surface comprising a material selected from the group consisting of: glass, coated glass, silicon, porous silicon, nylon, ceramic, and plastic.

* * * * *